United States Patent
Lieberman et al.

(10) Patent No.: US 11,147,828 B2
(45) Date of Patent: Oct. 19, 2021

(54) LET-7 MICRORNA AND MIMETICS THEREOF AS THERAPEUTICS FOR CANCER

(71) Applicant: CHILDREN'S MEDICAL CENTER CORPORATION, Boston, MA (US)

(72) Inventors: Judy Lieberman, Brookline, MA (US); Erwei Song, Guangzhou (CN); Fengyan Yu, Guangzhou (CN); Xiaoqu Hu, Guangzhou (CN)

(73) Assignee: Children's Medical Center Corporation, Boston, MA (US)

( * ) Notice: Subject to any disclaimer, the term of this patent is extended or adjusted under 35 U.S.C. 154(b) by 155 days.

(21) Appl. No.: 16/212,416

(22) Filed: Dec. 6, 2018

(65) Prior Publication Data

US 2019/0224228 A1 Jul. 25, 2019

Related U.S. Application Data

(63) Continuation of application No. 14/283,992, filed on May 21, 2014, now abandoned, which is a continuation of application No. 12/525,020, filed as application No. PCT/US2008/052654 on Jan. 31, 2008, now abandoned.

(60) Provisional application No. 60/898,610, filed on Jan. 31, 2007.

(51) Int. Cl.

| | |
|---|---|
| *C12N 15/11* | (2006.01) |
| *A61K 31/7105* | (2006.01) |
| *A61K 47/68* | (2017.01) |
| *A61K 31/7088* | (2006.01) |
| *C12N 15/113* | (2010.01) |
| *A61K 45/06* | (2006.01) |

(52) U.S. Cl.
CPC ...... *A61K 31/7105* (2013.01); *A61K 31/7088* (2013.01); *A61K 45/06* (2013.01); *A61K 47/6807* (2017.08); *C12N 15/113* (2013.01); *C12N 2310/11* (2013.01); *C12N 2310/111* (2013.01); *C12N 2310/141* (2013.01)

(58) Field of Classification Search
CPC .. C12N 15/113; C12N 2310/141; A61P 35/00
See application file for complete search history.

(56) References Cited

U.S. PATENT DOCUMENTS

| | | |
|---|---|---|
| 7,674,617 B2 | 3/2010 | Kim et al. |
| 2006/0189557 A1 | 8/2006 | Slack et al. |
| 2009/0163430 A1 | 6/2009 | Johnson et al. |

FOREIGN PATENT DOCUMENTS

| | | |
|---|---|---|
| AU | 2007333109 A1 | 6/2008 |
| WO | 1995022618 A1 | 8/1995 |
| WO | 2003/029459 A2 | 4/2003 |
| WO | 2006/028967 A2 | 9/2006 |

OTHER PUBLICATIONS

Vinogradov et al., "Cancer stem cells and drug resistance: the potential of nanomedicine", Nanomedicine 7(4) 597-615 (2012).
Wu et al., "Identification of novel prostate-specific antigen-binding peptides modulating its enzyme activity", Eur. J. Biochem 267:6212-6220 (2000).
Soifer et al., "MicroRNAs in disease and potential therapeutic applications" Molecular Therapy 15 12: 2070-2079 (2007).
Velasco-Velazquez et al., "Breast cancer stem cells" Int J Biochem Cell Biol 44(4) 573-577 (2012).
Zhang, B. et al., "microRNAs as oncogenes and tumor suppressors." Developmental Biology 302:1-12, 2007.
Lee, Y. S. and Dutta, A., "MicroRNAs: Small but potent oncogenes or tumor suppressors." Current Opinion in Investigational Drugs 7(5):560-564, 2006.
Takamizawa, J. et al., "Reduced Expression of the let-7 MicroRNAs in Human Lung Cancers in Association with Shortened Postoperative Survival." Cancer Research 64:3753-3756, 2004.
Akao, Y. et al., "let-7 MicroRNA Functions as a Potential Growth Suppressor in Human Colon Cancer Cells." Biol. Pharm. Bull. 29(5):903-906, 2006.
Johnson, S. M. et al., "RAS Is Regulated by the let-7 MicroRNA Family." Cell 120:635-647, 2005.
Abbott, A. L. et al., "The let-7 MicroRNA family members mir-48, mir-84, and mir-241 function together to regulate developmental timing in Caenorhabditis elegans" Dev Cell 9, 403-414 (2005).
Al-Hajj, M. et al. "Prospective identification of tumorigenic breast cancer cells" Proc Natl Acad Sci U S A 100, 3983-3988 (2003).
Banerjee, D. et al. "Control of developmental timing by small temporal RNAs: a paradigm for RNA-mediated regulation of gene expression" BioEssays 24, 119-129 (2002).
Bos, J. L. "ras oncogenes in human cancer: a review" Cancer Res 49, 4682-4689 (1989).
Calin, G. A. et al. "Human microRNA genes are frequently located at fragile sites and genomic regions involved in cancers" Proc Natl Acad Sci U S A 101, 2999-3004 (2004).
Chen, C. Z. "MicroRNAs as oncogenes and tumor suppressors" N Engl J Med 353, 1768-1771 (2005).

(Continued)

*Primary Examiner* — Ekaterina Poliakova-Georgantas
(74) *Attorney, Agent, or Firm* — Nixon Peabody LLP

(57) ABSTRACT

The present invention relates to methods to treat or prevent cancers in a subject, in particular the present invention relates to a method of treating and/or preventing cancer comprising targeting cancer stem cells by administering miRNAs which have reduced expression or are lacking in the cancer stem cells. in some embodiments, the miRNAs that are reduced or lacking in cancer stem cells are let-7 miRNAs. In alternative embodiments, the present invention relates to a method of treating and/or preventing cancer comprising targeting cancer stem cells by administering miRNAs which have increased expression levels in the cancer stem cells. Another aspect of the present invention relates to methods to enrich for a cancer stem cell population. Another aspect of the present invention relates to methods to identify miRNAs which contribute to the self-renewal capacity of cancer stem cells.

12 Claims, 28 Drawing Sheets

Specification includes a Sequence Listing.

(56) References Cited

OTHER PUBLICATIONS

Croce, C. M. et al. "miRNAs, cancer, and stem cell division" Cell 122, 6-7 (2005).
Dalerba, P. et al. "Cancer Stem Cells: Models and Concepts" Annu Rev Med, 267-284 (2007).
Dean, M. et al. "Tumour stem cells and drug resistance" Nat Rev Cancer 5, 275-284 (2005).
Dick, J. E. "Acute myeloid leukemia stem cells" Ann N Y Acad Sci 1044, 1-5 (2005).
Dontu, G. et al. "In vitro propagation and transcriptional profiling of human mammary stem/progenitor cells" Genes Dev 17, 1253-1270 (2003).
Dontu, G. et al. "Role of Notch signaling in cell-fate determination of human mammary stem/progenitor cells" Breast Cancer Res 6, R605-R615 (2004).
Downward, J. "Targeting RAS signalling pathways in cancer therapy" Nat Rev Cancer 3, 11-22 (2003).
Eramo, A. et al. "Chemotherapy resistance of glioblastoma stem cells" Cell Death Differ 13, 1238-1241 (2006).
Galli, R. et al. "Isolation and characterization of tumorigenic, stem-like neural precursors from human glioblastoma" Cancer Res 64, 7011-7021 (2004).
Großhans, H. et al. "The temporal patterning microRNA let-7 regulates several transcription factors at the larval to adult transition in C. elegans" Dev Cell 8, 321-330 (2005).
Hanahan, D. et al. "The hallmarks of cancer" Cell 100, 57-70 (2000).
Hatfield, S. D. et al. "Stem cell division is regulated by the microRNA pathway" Nature 435, 974-978 (2005).
Iorio, M. V. et al. "MicroRNA gene expression deregulation in human breast cancer" Cancer Res 65, 7065-7070 (2005).
Jordan, C. T. et al. "Mechanisms controlling pathogenesis and survival of leukemic stem cells" Oncogene 23, 7178-7187 (2004).
Jordan, C. T. et al. "Cancer stem cells" N Engl J Med 355, 1253-1261 (2006).
Kawasaki, H. et al. "siRNAs generated by recombinant human Dicer induce specific and significant but target site-independent gene silencing in human cells" Nucleic Acids Res 31, 981-987. (2003).
Lee, S. K. et al. "Lentiviral delivery of short hairpin RNAs protects CD4 T cells from multiple clades and primary isolates of HIV" Blood 106, 818-26 (2005).
Liu, G. et al. "Analysis of gene expression and chemoresistance of CD133+ cancer stem cells in glioblastoma" Mol Cancer 5, 67 (2006).
Lu, J. et al. "MicroRNA expression profiles classify human cancers" Nature 435, 834-838 (2005).
Muller, A. et al. "Involvement of chemokine receptors in breast cancer metastasis" Nature 410, 50-56 (2001).
Murdie, P. "MicroRNA signature predicts prognosis and progression of chronic lymphocytic leukemia" Nat Clin Pract Oncol 3, 67 (2006).
O'Brien C, A. et al. "A human colon cancer cell capable of initiating tumour growth in immunodeficient mice" Nature 106-110 (2007).
Patrawala, L. et al. "Highly purified CD44+ prostate cancer cells from xenograft human tumors are enriched in tumorigenic and metastatic progenitor cells" Oncogene 25, 1696-1708 (2006).
Polyak, K. et al. "Roots and stems: stem cells in cancer" Nat Med 12, 296-300 (2005).
Ponti, D. et al. "Isolation and in vitro propagation of tumorigenic breast cancer cells with stem/progenitor cell properties" Cancer Res 65, 5506-5511 (2005).
Reinhart, B.J. et al. "The 21-nucleotide let-7 RNA regulates developmental timing in Caenorhabditis elegans" Nature 403, 901-906 (2000).
Shcherbata, H. R. et al. "The MicroRNA pathway plays a regulatory role in stem cell division" Cell Cycle 5, 172-175 (2006).
Sheridan, C. et al. "CD44+/CD24− breast cancer cells exhibit enhanced invasive properties: an early step necessary for metastasis" Breast Cancer Res 8, R59 (2006).
Singh, S. K. et al. "Identification of human brain tumour initiating cells" Nature 432, 396-401 (2004).
Song, E. et al. "Antibody mediated in vivo delivery of small interfering RNAs via cell-surface receptors" Nat Biotechnol 23, 709-717 (2005).
Soutschek, J. et al. "Therapeutic silencing of an endogenous gene by systemic administration of modified siRNAs" Nature 432, 173-178 (2004).
Tang, F. et al. "MicroRNA expression profiling of single whole embryonic stem cells" Nucleic Acids Res 34, e9 (2006).
Townson, J. L. et al. "Dormancy of solitary metastatic cells" Cell Cycle 5, 1744-1750 (2006).
Vander Borght, S. et al. "Breast cancer resistance protein (BCRP/ABCG2) is expressed by progenitor cells/reactive ductules and hepatocytes and its expression pattern is influenced by disease etiology and species type: possible functional consequences" J Histochem Cytochem 54, 1051-1059 (2006).
Vescovi, A. L. et al. "Brain tumour stem cells" Nat Rev Cancer 6, 425-436 (2006).
Wang, J. C. et al. "Cancer stem cells: lessons from leukemia" Trends Cell Biol 15, 494-501 (2005).
Wicha, M. S. "Cancer stem cells and metastasis: lethal seeds" Clin Cancer Res 12, 5606-5607 (2006).
Yanaihara, N. et al. "Unique microRNA molecular profiles in lung cancer diagnosis and prognosis" Cancer Cell 9, 189-198 (2006).
Youn, B. S. et al. "Scale-up of breast cancer stem cell aggregate cultures to suspension bioreactors" Biotechnol Prog 22, 801-810 (2006).

FIG. 7A hsa-let-7a MIMAT0000062 UGAGGUAGUAGGUUGUAUAGUU (SEQ ID NO:1)
hsa-let-7b MIMAT0000063 UGAGGUAGUAGGUUGUGUGGUU (SEQ ID NO:2)
hsa-let-7c MIMAT0000064 UGAGGUAGUAGGUUGUAUGGUU (SEQ ID NO:3)
hsa-let-7d MIMAT0000065 AGAGGUAGUAGGUUGCAUAGU (SEQ ID NO:4)
hsa-let-7e MIMAT0000066 UGAGGUAGGAGGUUGUAUAGU (SEQ ID NO:5)
hsa-let-7f MIMAT0000067 UGAGGUAGUAGAUUGUAUAGUU (SEQ ID NO:6)

FIG. 7B hsa-let-7a-1 MI0000060 pre-miRNA:
UGGGAUGAGGUAGUAGGUUGUAUAGUUUUAGGGUCACACCCACCACUGGGAGAUAACUAU
ACAAUCUACUGUCUUUCCUA (SEQ ID NO:7)

FIG. 7C

HOMO SAPIENS let-7a-1 STEM-LOOP (SEQ ID NO:8):

```
     u   gu    aguagguugauaguu       uuaggucacac
uggga gag                      u                c
||||| |||  |||||||||||||||||||      |||||||||||  c
auccu uuc    ucaucuaacauaucaa       uagagguucacc a
     -   ug
```

FIG. 7D

THE OLIGONUCLEOTIDES (let-7 TARGET SEQUENCE- 5'-AACTATACAACCTACTACCTCA-3' UNDERLINED
(SEQ ID NO:9) INSERTED INTO THE REPORTER VECTOR:
5'-AATGCACTAGT AACTATACAACCTACTACCTCAGCTCAGCAAGCTTAATGC (SEQ ID NO:10)
5'-GCATTAAGCTTGCTGAGCTGAGGTAGTAGGTTGTATAGTTACTAGTGCATT (SEQ ID NO:11)

LET-7 MICRORNA AND MIMETICS THEREOF AS THERAPEUTICS FOR CANCER

CROSS REFERENCE TO RELATED APPLICATIONS

This Application is a Conitnuation of U.S. patent application Ser. No. 14/283,992 filed on May 21, 2014, which is a Continuation of U.S. patent application Ser. No. 12/525,020, filed on Aug. 26, 2010, which is a 371 National Phase Entry Application of International Application PCT/US2008/052654 filed Jan. 31, 2008, which designated the U.S., and claims benefit under 35 U.S.C. § 119(e) of U.S. Provisional Application Ser. No. 60/898,610 filed Jan. 31, 2007, the contents of which is incorporated herein in its entirety by reference.

The Sequence Listing associated with this application is provided in text format in lieu of a paper copy, and is hereby incorporated by reference into the specification. The name of the text file containing the Sequence Listing is 2018-12-06_Sequence_Listing_701039-059233C2.txt. The text file is 3,964 bytes and is being submitted electronically via EFS-Web, concurrent with the filing of the specification.

GOVERNMENT SUPPORT

This invention was made with government support to ES under Contract No. 30525022 awarded by the National Science Foundation of China, Contract No. 2005CB724605 awarded by the 973 Program Project from Ministry of Science and Technology of China.

BACKGROUND OF THE INVENTION

Accumulating evidence suggests that many cancers are maintained in a hierarchical organization of rare, slowly dividing tumor-initiating cells, rapidly dividing amplifying cells (precursor cells) and differentiated tumor cells[1,2]. Tumor-initiating (also termed cancer stem) cells have been identified in hematologic[3-5], brain[6-8], breast[9,10], prostate[11] and colon cancers[12]. Stem cells, which are self-renewing and can differentiate into heterogeneous cell populations, are highly tumorigenic[1,2]. Tumor-initiating cells are thought not only to be the source of the tumor, but can also to be responsible for tumor progression[13], metastasis[14,15], resistance to cancer therapy and subsequent tumor recurrence[16,17].

Although there is a growing consensus that cancer stem cells are important in generating tumors and for resistance to therapy and metastasis, a major obstacle to their study is getting enough cells because of their very low frequency in tumors[9,10,12,37]. Therefore, there is much need in the art for an efficient method for enriching for these cancer stem cells.

In some organisms, miRNAs are known to play a role in maintaining stemness of embryonic stem (ES) cells, because ES cells deficient in miRNA processing genes cannot be maintained[20]. Previous studies have shown an overall reduction in miRNA expression in embryonic or tissue stem cells[21] and changes in specific miRNAs have been associated with self-renewal and differentiation of ES cells[20,22]. Moreover, miRNA expression profiling has been shown to be useful for characterizing the stage, subtype and prognosis of some cancers[18,23,24]

Based on the importance of cancers stem cells believed to be not only to be the source of the tumor, but also to be responsible for tumor progression[13], metastasis[14,15], resistance to cancer therapy and subsequent tumor recurrence[16,17], a method for reliably determining if a subject has a cancer stem cell is needed in the art. In addition, a method for reducing the occurrence of cancer stem cells and a method of treating cancer stem cells in patients are also highly desirable.

SUMMARY OF THE INVENTION

The present invention relates to methods to treat or prevent cancers in a subject, in particular the present invention relates to a method of treating and/or preventing cancer comprising targeting cancer stem cells by administering miRNAs which have reduced expression or are lacking in the cancer stem cells. In some embodiments, the miRNAs that are reduced or lacking in cancer stem cells are let-7 miRNAs. Conversely, in alternative embodiments, the present invention relates to a method of treating and/or preventing cancer comprising targeting cancer stem cells by administering agents which inhibit the expression of miRNAs, which have increased expression levels in the cancer stem cells. Another aspect of the present invention relates to methods to enrich for a cancer stem cell population. Another aspect of the present invention relates to methods to identify miRNAs which contribute to the self-renewal capacity of cancer stem cells.

One aspect of the present invention relates to a method of treating or preventing a cancer in a subject which comprises administering to the subject a pharmaceutical composition comprising an effective amount of at least one let-7 miRNA, or an agent that increases the expression of a let-7 miRNA, wherein the let-7 miRNA binds to and inhibits an RNA transcript comprising a let-7 target sequence which is expressed in a cancer stem cell. In some embodiments, the let-7 target sequence comprises SEQ ID NO:9 or a homologue thereof. For example, the let-7 target sequence that is a homologue of SEQ ID NO:9 can comprise SEQ ID NO: 10 or SEQ ID NO:11.

In some embodiments, the method comprises administering a pharmaceutical composition comprising let-7 miRNA, where let-7 miRNA is encoded by a let-7-encoding nucleic acid construct. As a non-limiting example, the let-7 miRNA can be a member of the let-7 family of miRNAs, such as, but not limited to let-7a, let-7b, let-7c, let-7d, let-7e and let-7f and homologues thereof that are effective in gene silencing. In some embodiments, the let-7 is let-7a or let-7a1.

In some embodiments, a let-7 miRNA can be a pri-miRNA, pre-miRNA, mature miRNA or a fragment or variant thereof effective in gene silencing. In some embodiments, the let-7 miRNA comprises SEQ ID NO:1 or a fragment or homologue thereof effective in gene silencing. In alternative embodiments, let-7 miRNA homologues can be used, for example the let-7 miRNA from the let-7 miRNA family including, but not limited to, let-7 miRNA comprising SEQ ID NOS:2-6 or a fragment or homologue thereof effective in gene silencing. In some embodiments, a let-7 miRNA useful in the methods disclosed herein is a pre-miRNA of SEQ ID NO:7 or a fragment or homologue thereof effective in gene silencing. In some embodiments, a let-7 miRNA is a let-7a-1 stem-loop. In alternative embodiments, the let-7 miRNA is let-7a-1 of SEQ ID NO:8 or a fragment or homologue thereof effective in gene silencing. In other embodiments, the let-7 miRNA is an RNA interference-inducing (RNAi) molecule including, but not limited to, a siRNA, dsRNA, stRNA, shRNA and gene silencing variants thereof. In alternative embodiments the let-7 miRNA is an agent which binds and inhibits an RNA transcript comprising a let-7 target sequence. Examples of such agents include, but are not limited to a small molecule, protein, antibody, aptamer, ribozyme, nucleic acid or nucleic acid analogue.

In some embodiments, the methods as disclosed herein are useful for the treatment or prevention of a cancer, for example where a cancer is characterized by the reduction or loss of a let-7 miRNA. In some embodiments the cancer comprises a cancer stem cell. In some embodiments, the cancer is a pre-cancer, and/or a malignant cancer and/or a therapy resistant cancer. In some embodiments, the cancer is a breast cancer.

In some embodiments, the let-7 miRNA or let-7 agent can further comprise a binding moiety and a targeting moiety, and in some embodiments the binding moiety binds let-7 miRNA to the targeting moiety. In some embodiments, a targeting moiety is a cell surface receptor ligand or antigen-binding fragment thereof, for example a cell surface receptor ligand including, but not limited to, CD133, CD44, mini-MUC; MUC-1; HER2/neu; HER2; mammoglobulin; labyrinthin; SCP-1; NY-ESO-1; SSX-2; N-terminal blocked soluble cytokeratin; 43 kD human cancer antigen; human tumor associated antigen (PRAT); human tumor associated antigen (TUAN); L6 antigen; carcinoembryonic antigen; CA15-3; oncoprotein 18/stathmin (Op18); human glandular kallikrein (hK2); NY-BR antigens, tumor protein D52, and prostate-specific antigen; and early endosome antigen 1 (EEA), c-kit, ABC7, SCA1 or combinations or antigen binding fragments thereof. In some embodiments, a targeting moiety useful in the methods as disclosed herein is an antibody, for example an antibody including not just complete or full length antibodies, but also antibody derivatives, such as a single chain antibody, a Fab portion of an antibody or a (Fab')$_2$ segment, which binds to a cell surface antigen present on a cancer cell. In some embodiments, a binding moiety useful in the methods as disclosed herein is a protein or a nucleic acid binding domain of a protein, and in some embodiments the binding moiety is fused to the carboxyl terminus of the targeting moiety, and in some embodiments, the binding moiety is the protein protamine or nucleic acid binding fragment of protamine.

In some embodiments, the methods as disclosed herein further comprise administering to the subject at least one or more additional cancer therapies, such as surgery, chemotherapy, radiotherapy, thermotherapy, immunotherapy, hormone therapy and laser therapy.

In some embodiments, the let-7 miRNA is administered to a subject more than once, and can be administered before, after or at the same time as an additional cancer therapy or agent.

In some embodiments, the let-7 miRNA is encoded by a nucleic acid in a vector, for example, a plasmid, cosmid, phagemid, or virus or variants thereof, and in some embodiments the let-7 miRNA is operatively linked to a promoter. In some embodiments, the vector further comprises one or more in vivo expression elements for expression in human cells, such as a promoter or enhancer and combinations thereof.

In some embodiments, administration of the let-7 miRNA or let-7 agents can be intravenous, intradermal, intramuscular, intraarterial, intralesional, percutaneous, subcutaneous, or by aerosol administration, or combinations thereof. In some embodiments, administration is prophylactic administration, and in alternative embodiments, administration is therapeutic administration.

In some embodiments, the methods and compositions as disclosed herein can be adminisistered to a subject, where the subject is, for example, a mammal such as a human. In some embodiments, the subject has previously undergone at least one or more cancer therapies including, but not limited to, surgery, chemotherapy, radiotherapy, thermotherapy, immunotherapy, hormone therapy and laser therapy.

Another aspect of the present invention relatest to a method of treating or preventing a cancer in a subject, the methods comprising administering to the subject an effective amount of at least one agent that inhibits one or more genes and/or a product of such gene expression, wherein the RNA transcript of (i.e. transcribed from) the gene comprises a let-7 target sequence, and the gene is gene silenced by let-7 miRNA in non cancer cells.

In some embodiments, the let-7 target sequence comprises SEQ ID NO:9 or a homologue thereof effective in gene silencing. For example, the let-7 target sequence can comprise SEQ ID NO:10 or SEQ ID NO:11 or a homologue thereof effective in directing gene silencing.

In some embodiments, the genes which comprise a let-7 target sequence in their RNA transcript include, but are not limited to, RAS, lin-42, KRAS, GRB2, hbl-1, daf-12, pha-4 or human homologues thereof.

In some embodiments, an agent as disclosed herein can be, for example a small molecule, nucleic acid, nucleic acid analogue, aptamer, ribozyme, peptide, protein, antibody, or variants and fragments thereof. In some embodiments, a nucleic acid agent can be DNA, RNA, nucleic acid analogue, peptide nucleic acid (PNA), pseudo-complementary PNA (pcPNA), locked nucleic acid (LNA) or analogue thereof, and in embodiments where the nucleic acid agent is RNA, the RNA can be a small inhibitory RNA (RNAi), siRNA, microRNA, shRNA, miRNA and analogues and homologues and variants thereof effective in gene silencing.

In some embodiments, a let-7 miRNA or agent can be admininstered to a subject via a variety of different routes, for example intravenous, intradermal, intramuscular, intraarterial, intralesional, percutaneous, subcutaneous, or by aerosol administration. In some embodiments, administration is prophylactic administration and in alternative embodiments, administration is therapeutic administration. In some embodiments, the methods and compositions as disclosed herein can be adminisistered to a subject, where the subject is, for example, a mammal such as a human. In some embodiments, the subject has previously undergone at least one or more cancer therapies, scuh as, but not limited to surgery, chemotherapy, radiotherapy, thermotherapy, immunotherapy, hormone therapy and laser therapy.

Another aspect of the present invention relates to a method to determine if a subject is at risk of having a metastasis or malignant cancer, the method comprising assessing the presence of a let-7 miRNA in a test biological sample obtained from the subject, wherein if the level of a let-7 miRNA in the test biological sample is reduced relative to the level of the let-7 miRNA in a reference sample, the subject is at risk of having a metastasis or a malignant cancer. In some embodiments, if the subject is identified as having a risk of metastasis or a malignant cancer, the method further comprises administering to the subject an effective amount of a pharmaceutical composition comprising at least one let-7 miRNA, or an agent that increases the expression of a let-7 miRNA according to claim 1.

In some embodidments, biological sample as disclosed herein is a tissue samples, such as a tumor tissue sample or a cancer cell or tumor cell, for example a biopsy tissue sample obtained from the subject, such as a biopsy tissue sample is from a cancer. In some embodiments, the biopsy sample is from breast cancer.

In some embodiments, let-7 miRNA levels can be determined by any methods known by persons of ordinary skill in the art. For example, let-7 miRNA levels can be determined using a nucleic acid probe in, for example, Northern blot analysis, PCR, RT-PCR or quantitative RT-PCR. Examples of a nucleic acid probe useful in the methods as disclosed herein include a nucleic acid probe corresponding to SEQ ID NO:12 or SEQ ID NO:13 or SEQ ID NO:14 or a nucleic acid probe which specifically hybridizes to SEQ ID NO: 13 or SEQ ID NO:14, where such nucleic acid probes can be used in Northern blot analysis, PCR, RT-PCR, quantitative RT-PCR and other methods to determine expression levels of nucleic acids in a biological sample.

Another aspect of the present invention relates to a method to enrich for cancer stem cells, the method comprising; (i) transplanting a plurality of cancer cells into a mammal, wherein the mammal is administered a low dose cancer therapy, and allowing a sufficient period of time for the cancer cells to form a tumor, (ii) removing the tumor from the mammal and dissociating the tumor into single cells, (iii) transplanting a plurality of the single cells into a mammal, wherein the mammal is administered a low dose cancer therapy, and allowing a sufficient period of time for the cancer cells to form a tumor, (iv) repeating steps (iii) and (iv) a plurality of times, for example, at least 2 times and in some instances at least 3, 4, 5 or more times, (v) removing the tumor from the mammal and dissociating the tumor into single cells, and (vi) culturing the cells as single-cells for sufficient time to form an embryoid body, wherein the embryoid body comprise a population of cells enriched in cancer stem cells.

In some embodiments of methods to enrich for cancer stem cell, the embryoid body is a mammosphere. In some embodiments, a cancer cell that is transplanted into a mammal is a primary cancer cell or a cancer cell line, such as a genetically modified primary cancer cell or cancer cell line. In some embodiments, a cancer cell is from a biological sample, such as a biopsy tissue, for example a cancer biopsy tissue sample.

In alternative embodiments where the cancer cell is of a cancer cell line, the cancer cell line can be derived from a tumor or cancer including, but not limited to, breast cancer, lung cancer, head and neck cancer, bladder cancer, stomach cancer, cancer of the nervous system, bone cancer, bone marrow cancer, brain cancer, colon cancer, esophageal cancer, endometrial cancer, gastrointestinal cancer, genital-urinary cancer, stomach cancer, lymphomas, melanoma, glioma, bladder cancer, pancreatic cancer, gum cancer, kidney cancer, retinal cancer, liver cancer, nasopharynx cancer, ovarian cancer, oral cancers, bladder cancer, hematological neoplasms, follicular lymphoma, cervical cancer, multiple myeloma, osteosarcomas, thyroid cancer, prostate cancer, colon cancer, prostate cancer, skin cancer, stomach cancer, testis cancer, tongue cancer, or uterine cancer. In some embodiments, the cancer cell line is a breast cancer cell line.

In some embodiments, cancer cells are transplanted into a mammal which can be any mammal, such as a monkey, rodent or genetically modified rodent. In some embodiments, the mammal is an immunocompromised mammal, for example, a NOD/SCID mouse.

In some embodiments of methods to enrich for cancer stem cells, a cancer therapy can be for example, chemotherapy, radiotherapy, thermotherapy, immunotherapy, hormone therapy and laser therapy. An example of chemotherapy is the chemotherapy agent Epirubicin.

In some embodiments of methods to enrich for cancer stem cells, administration of the low-dose cancer therapy can be continuous administration or in alternative embodiments, non-continuous administration, for example twice a day, once a day, every other day, twice a week, once a week, every other week or once a month. In some embodiments, administration can be by any route known by persons of ordinary skill in the art, such as intravenous, intradermal, intramuscular, intraarterial, intralesional, percutaneous, subcutaneous, intraperitoneal, or aerosol administration. In some embodiments, the time to culture the cells to enable them to form an embryoid body is a sufficient period of time is a period of time to allow the tumors to reach at least about 2 cm in diameter. In some embodiments, transplanting the cells relates to transplanting the cells into the mammary fat pad of a female rodent.

Another aspect of the present invention relates to methods to identify miRNAs that contribute to the self-renewal capacity of cancer stem cells, the method comprising obtaining cancer stem cells, for example by the methods as disclosed herein, and analyzing the expression of a plurality of miRNAs from said cancer stem cells, and comparing the expression profile of miRNAs of said cancer stem cells with the miRNA expression profile from a reference sample, wherein an increased or reduced level of expression of an miRNA in the cancer stem cells as compared to the level of miRNA in the reference sample identifies an miRNA that contributes to the self-renewal capacity of the cancer stem cells. In some embodiments, a reference sample useful in the methods as disclosed herein is a non-stem cell cancer cell, or a differentiated cancer stem cell.

Any means to analyze a miRNA expression profile known by persons of ordinary skill in the art can be used in the methods as disclosed herein, for example by microarray assay.

In some embodiments of the methods as disclosed herein, the methods can further comprise assessing the miRNA that contributes to the self-renewal capacity, the method comprising introducing into the cancer stem cell the miRNA if the miRNA is identified to be expressed at a lower level in a cancer stem cell as compared to the reference sample, and assessing the ability of the cancer stem cell to from a embryoid body, wherein a reduced ability to from a embryoid body indicates that the miRNA contributes to a cancer stem cell's self-renewal capacity. In alternative embodiments, the methods can further comprise assessing the miRNA that contributes to the self-renewal capacity, the method comprising inhibiting the expression of an miRNA in the cancer stem cell if the miRNA is identified to be expressed at a higher level in the cancer stem cell as compared to the reference sample, and assessing the ability of the cancer stem cell to from an embryoid body, wherein a reduced ability to from an embryoid body identified an miRNA that contributes to cancer stem cell self-renewal capacity.

Another aspect of the present invention relates to a pharmaceutical composition comprising a let-7 miRNA and a pharmaceutically acceptable carrier, wherein the let-7 miRNA binds to and inhibits an RNA transcript comprising a let-7 target sequence.

Another aspect of the present invention relates to a pharmaceutical composition comprising an agent which increases the expression of a let-7 miRNA and a pharmaceutically acceptable carrier, wherein the let-7 miRNA binds to and inhibits an RNA transcript comprising a let-7 target sequence.

Another aspect of the present invention relates to a pharmaceutical composition comprising an agent which decreases the expression of at least one of miR-129, miR-140, miR-184 or miR-198 and a pharmaceutically acceptable carrier.

In some embodiments, a pharmaceutical composition as disclosed herein comprises a let-7 miRNA or an agent which increases a let-7 miRNA, and the let-7 target sequence comprises SEQ ID NO:9 or a homologue thereof effective in gene silencing, such as a let-7 target sequence comprising SEQ ID NO: 10 or SEQ ID NO:11.

In some embodiments, the pharmaceutical compositions as disclosed herein are useful of for the treatment or prevention of cancer in a subject, for example, for the treatment or prevention of breast cancer. In some embodiments, the subject is a mammal, such as a human subject.

In some embodiments where a pharmaceutical composition comprises an agent, the agent can be, for example, a small molecule, nucleic acid, nucleic acid analogue, aptamer, ribozyme, peptide, protein, antibody, or variants and fragments thereof. In some embodiments where the agent is a nucleic acid, the nucleic acid can be for example, DNA, RNA, nucleic acid analogue, peptide nucleic acid (PNA), pseudo-complementary PNA (pcPNA), locked nucleic acid (LNA) or analogue thereof.

BRIEF DESCRIPTION OF DRAWINGS

FIG. 1A shows that primary breast cancer cells isolated from surgical specimens from patients who received preoperative neoadjuvant chemotherapy are substantially enriched for self-renewing cells with the properties of cancer stem cells, compared to untreated patients. Representative images show increased numbers and size of mammospheres after 15 d of culture, and FIG. 1B shows a higher percentage of CD44$^+$CD24$^-$ cells in freshly isolated tumor cells from patients who received chemotherapy. Similarly, FIGS. 1C-1G show that passaging the human breast cancer cell line SKBR3 in Epirubicin-treated immunodeficient mice enriches for tumor-initiating cells. SK-3rd cells dissociated from the 3$^{rd}$ passage xenograft are self-renewing. They have enhanced ability, compared to the parental line, to form mammospheres, and the mammospheres can be repetitively passaged in vitro and are larger. FIG. 1C shows numbers of primary, secondary (generated from dissociated primary mammospheres) and tertiary (generated from dissociated secondary mammospheres) mammospheres on day 15 from 1000 cells. *, P<0.001 compared with SKBR3. FIG. 1D shows mammospheres generated from single-cell cultures of SK-3rd and SKBR3, imaged on indicated days of suspension culture. Shown are the mean±SD number of cells/sphere for each timepoint. *, P<0.001 compared with SKBR3. FIGS. 1F and 1G show that when SK-3rd cells have the phenotype of breast tumor-initiating cells; they are CD44$^+$CD24$^-$Oct4$^+$. FIG. 1E (left) shows when SK-3rd mammospheres are dissociated, and removed from growth factors and plated on collagen, they adhere and differentiate (FIG. 1E, right) and assume the parental SBKR3 phenotype (Oct-4 immunoblot, as shown in FIG. 1F). FIG. 1G shows that SK-3rd and SKBR3 cells cultured as spheres are CD44$^+$ CD24$^-$. When they differentiate in adherent cultures, they gradually assume the parental SBKR3 phenotype, but somewhat more rapidly for SKBR3 mammospheres.

FIG. 2A shows miRNA array analysis, which shows that miRNAs are differentially expressed in SK-3rd cells cultured in mammospheres (1) or adhered for 8 hr (2), 24 hr (3), or 10 days (4) and parent SKBR3 (5). Most miRNAs, including all let-7 homologs or let-7 family members, are reduced in SK-3rd cultured in mammospheres or just adhered for 8 hr, and increase during differentiation to similar levels as SKBR3. FIG. 2B shows the microarray results for let-7 were verified by Northern blot using a nonspecific let-7 probe, and FIG. 2C shows verification by qRT-PCR amplified for let-7a (mean±SD relative to U6). FIG. 1D shows that infection of SK-3rd with lentivirus expressing pre-let-7a (lenti-let-7) vs. empty vector increased let-7 expression to levels comparable to differentiated SK-3rd. let-7 function, assayed by luciferase assay in cells transfected with a reporter gene containing a let-7 target site in its 3'-UTR, is negligible in SK-3rd cells but increases upon differentiation or by infection with lenti-let-7 (*, P<0.001 compared with SK-3rd). Transfection with let-7 ASO reduces endogenous or exogenous let-7 activity (#, P<0.01 compared to cells not transfected with let-7 ASO). FIG. 2E shows that H-RAS, a target of let-7, is highly expressed in SK-3rd, but not in the differentiated adherent cell line or SKBR3 (protein assayed by immunoblot relative to α-actin). FIGS. 2F and 2G shows that infection with lenti-let-7 or lentivirus encoding RAS-shRNA, but not GFP-shRNA or empty vector, suppresses H-RAS expression in SK-3rd cells, while transfection of SKBR3 with let-7 ASO augments H-RAS protein. FIG. 2F shows let-7 is also reduced in primary mammospheres from isolated tumor cells from patients who received neoadjuvant chemotherapy, compared to patients who did not. FIG. 2F shows a northern blot of representative samples probed for let-7 family miRNAs and FIG. 2G shows qRT-PCR results for 5 chemotherapy-treated patients and 6 untreated patients amplified for let-7a (mean±SD relative to U6). In FIG. 2F, samples are mammospheric (lane 1) and adherent differentiated cell (lane 2) RNA from representative chemotherapy patient, compared with RNA extracted from a patient who did not receive chemotherapy (lane 3).

FIG. 3A shows that single cell cultures of dissociated SK-3rd cells, infected with lenti-let-7 or lentivirus expressing RAS-shRNA, but not GFP-shRNA or empty vector, form fewer mammospheres, and FIG. 3B shows that mammospheres that do form develop more slowly and are reduced in cell number (*, P<0.0001; compared to untransduced cells). Conversely, FIG. 3C shows that SKBR3 cells transfected with let-7a ASO, but not control lin-4 ASO, generate 10-fold more mammospheres. FIG. 3D shows that let-7 expression, assayed by qRT-PCR relative to U6, increases during in vitro differentiation of SK-3rd. FIG. 3E shows that SK-3rd cells infected with lenti-let-7, and to a lesser extent lentivirus expressing RAS-shRNA, proliferate less during in vitro differentiation than untransduced or control transduced cells as measured by [$^3$H]-incorporation *, P<0.01; #, P<0.05 compared with untransduced SK-3rd. FIG. 3F shows that after 10 d of in vitro differentiation, SK-3rd cells overexpressing let-7a, but not RAS-shRNA, have half as many undifferentiated cells lacking expression of the cytokeratins CK14 or CK18.

FIG. 4A shows tumor volume which was measured after subcutaneous mammary fat pad inoculation of 2×10$^3$ (top), 2×10$^4$ (middle) or 2×10$^5$ (bottom) SKBR3 cells or SK-3rd cells that were untransduced or transduced with empty vector or to express let-7. The number in the figure legend indicates the number of mice who developed tumors. 10 mice were in each group. Over-expression of let-7a led to fewer tumors and the tumors that arose grew more slowly. FIG. 4B shows tumors that grew in mice inoculated with 2×10$^5$ cells had similar histology by hematoxylin and eosin staining (HE, magnification 200×), but the SK-3rd tumors, either untransduced or transduced with empty vector, had higher expression of H-RAS (400×, and shown in FIG. 4C) and a higher proliferative index assessed by PCNA staining (400×, shown in FIG. 4D), than the parental SKBR3 cells or SK-3rd cells transduced with lenti-let-7.

FIG. 5A shows Hematoxylin and eosin staining of the lung (×200) and liver (×400) of mice implanted subcutaneously with 2×10$^5$ SK-3rd cells (either untransduced or transduced with lentivirus vector or lenti-let-7) or SKBR3. Arrows indicate focal metastasis. FIG. 5B shows mean±SD wet lung weight in mice bearing tumor xenografts (n=10/group). FIG. 5C shows the expression of human HPRT mRNA relative to mouse GAPDH, by qRT-PCR. The numbers indicate the number of animals in each group of 10 with lung or liver metastasis. N.D., not detected

FIGS. 7A-7D shows sequences of let-7 miRNA. FIG. 7A shows the nucleic acid sequences of isoforms or homologues of let-7, let-7a (SEQ ID NO:1); let-7b (SEQ ID NO:2); hsa-let-7c (SEQ ID NO:3); hsa-let-7d (SEQ ID NO:4); hsa-let-7e (SEQ ID NO:5); hsa-let-7f (SEQ ID NO:6). FIG. 7B shows the nucleic acid sequence of let-7 miRNA (SEQ ID NO:7). FIG. 7C shows the nucleic acid sequence *homo sapiens* let-7a1 stem loop (SEQ ID NO: 8). FIG. 7D shows the nucleic acid sequence of the let-7 target sequence (5'-AACTATACAACCTACTACCTCA-3'; SEQ ID NO: 9) and 2 let-7 target sequences (SEQ ID NO:10 and SEQ ID NO:11) inserted into the reporter vector.

FIG. 8A shows that the majority of freshly isolated SK-3rd cells are CD44+CD24-, as expected for BT-IC, while cells with this phenotype are rare in SKBR3 (representative data of five experiments shown). FIG. 8B shows that when SK-3rd spheres are dissociated, removed from growth factors, and plated on collagen for 8 hr (top), they do not express luminal (Muc1 and CK-18) or myoepithelial (CK-14 and α-SMA) differentiation markers, while after further differentiation (bottom), they develop into elongated cells with subpopulations staining for either differentiated subtype. FIG. 8C shows that freshly isolated SK-3rd cells are enriched for Hoechst low SP cells compared with SKBR3 cells.

FIG. 9A shows Northern Blot probed for let-7m and FIG. 9B shows results from qRT-PCR amplified for let-9a (mean±SD relative to U6) to verify the microarray results. Spheres derived from either SK-3rd or SKBR3 show similar low expression of let-7 that increases gradually beginning 1 days following induction of differentiation and plateaus within 6 days. #, p<0.01; *, p<0.001 as compared with cells cultured in spheres. Error bars correspond to mean±SD. FIG. 9C shows HMGA2, a target of let-7, is highly expressed in mammospheric SK-3rd but not in differentiated adherent SK-3rd or SKBR3 (protein assayed by immunoblot relative to b-actin). Infection with lenti-let-7 or lentivirus encoding RAS- or HMGA2-shRNA, but not GFP shRNA or vector, suppresses HMGA2 expression, respectively, in mammospheric SK-3rd cells, while transfection of SKBR3 with let-7 ASO augments HMGA2 protein. In addition, FIGS. 9D-F show tumors from eight untreated patients and five patients treated with neoadjuvant chemotherapy were enriched for BT-IC by sorting for lin⁻CD44⁺CD24⁻ cells or by growth as mammospheres. Tumors depleted of BT-IC by adherent growth or by excluding CD44⁺CD24⁻ cells also have reduced let-7 compared to adjacent normal breast tissue. FIG. 9D shows FACS analysis and FIG. 9E shows Northern blots probed for let-7 and U6 for representative untreated (#7), and neoadjuvant chemotherapy treated (#5) patients. FIG. 9F shows mean±SD of relative let-7 expression for all samples analyzed by qRT-PCR. Infection with lenti-let-7 increases let-7 in BT-IC-enriched primary cells. #, p<0.05; *, p<0.01 compared with samples depleted of CD44⁺CD24⁻ cells.

FIG. 10A shows that BT-IC-enriched cells, sorted for lin⁻CD44⁺CD24⁻$^{/low}$ phenotype from primary chemotherapy-naive breast tumors, have a markedly higher capacity to form mammospheres compared with CD44⁺CD24⁻-depleted cells. Transduction with lenti-let-7, but not lentivector, reduces mammosphere generation. *, p<0.001 compared with untransduced cells. Mammosphere formation by let-7-transduced BT-IC is also significantly reduced on serial passage but is stable in untransduced cells. FIG. 10B shows single-cell cultures of dissociated SK-3$^{rd}$ cells, infected with lenti-HMGA2-shRNA, form a comparable number of mammospheres as uninfected cells or cells infected with lenti-GFP-shRNA or lentivector. Lenti-let-7 was used as a positive control. *, p<0.01 as compared with untransduced SK-3rd. FIG. 10C shows that silencing HMGA2 with lenti-HMGA2-shRNA reduces proliferation of SK-3rd cells on day 4 of in vitro differentiation in adherent cultures (peak of proliferation), but not as much as lenti-let-7 transduction. Cell proliferation was measured by [3H]-incorporation *, p<0.01; #, p<0.05 compared with untransduced SK-3rd. FIG. 10D shows that transduction with lenti-HMGA2-shRNA or lenti-let-7, but not with lenti-GFP-shRNA or vector, similarly reduces the proportion of lin⁻ cells in SK-3rd cells cultured in mammospheres. *, p<0.01 compared with vector transduced cells. Error bars correspond to mean±SD.

DESCRIPTION OF THE INVENTION

Figure 1A:
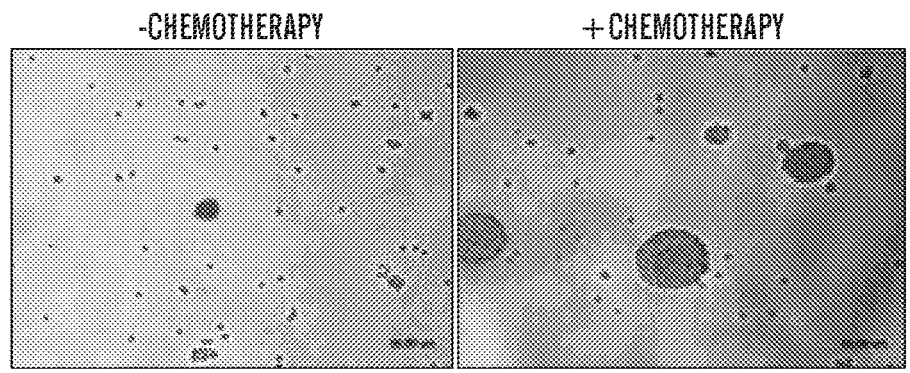
FIGS. 1A-1G show that breast cancer cells under pressure of chemotherapy are enriched for breast tumor-initiating cells.

In accordance with the present invention, the inventors have discovered that preoperative chemotherapy in patients enriches for tumor-initiating cells, herein referred to as "cancer stem cells". The inventors have also discovered that cancer stem cells lack or have reduced expression of specific miRNA as compared with normal tissue and non-stem cell cancer cells. The inventors herein have discovered cancer stem cells lack or have reduced miRNA expression of miRNAs including, but not limited to, let-7, miR-107, miR-10a, miR-128a, miR128b, miR-132, miR-138, miR-16, miR-17, miR-195, miR-199a, miR-20, miR-200a, miR-200b, miR-200c, miR-20b, miR-22. In particular, the inventors have discovered that cancer stem cells have reduced or lack let-7 miRNA expression compared with normal tissue and non-stem cell cancer cells. Furthermore, the inventors have discovered that breast cancer stem cells have reduced expression of let-7 which is not the case in non-stem cell breast cancer cells, and that reduced expression or lack of let-7 is required to maintain "stemness" of the cancer stem cells, for example lack of let-7 enables cancer stem cells to self-renew and be maintained in an undifferentiated state. The inventors also discovered that cancer stem cells that lack or have reduced expression of let-7 as compared to non-stem cell cancers were highly malignant and were more likely to result in metastasis in the liver and lung. Thus, the inventors have discovered that cells having reduced expression or lacking specific miRNAs, for example but not limited to, cells having reduced expression or lacking expression of let-7 miRNA identifies a cell as a cancer stem cell and identifies the cell as contributing to increased tumorigenicity and cancer metastasis.

In another aspect of the invention, the inventors discovered that expression of specific miRNAs is reduced or absent in cancer stem cells, and that expression of such miRNAs reduces these cancer stem cells' self-proliferative capacity and converts the cancer stem cells from highly malignant and metastasizing cancer stem cells into less malignant cells. For example, the expression of let-7 in cancer stem cells was discovered to reduce the cells capacity for self-proliferation and render them less malignant. Thus, the inventors have discovered that specific miRNA that are reduced and/or lacking in cancer stem cells act as tumor suppressors; for example, let-7 acts as a tumor suppressor.

Another aspect of the invention relates to the inventors discovery of a novel method to enrich for cancer stem cells using repeated passaging of cancer cells. The inventors demonstrate a method for enriching for a population of cancer stem cells by (i) transplanting cancer cells in an animal model in vivo, and allowing the cancer cells to grow into a tumor in the presence of low dose chemotherapy, then harvesting the cancer cells from the tumor and (ii) re-transplanting the harvested cancer cells into a subsequent animal model and repeating step (i). The steps (i) and (ii) can be repeated a number of times, for example at least 2, or at least 3 or at least 4 or up to as many as 10 or more times to enrich for a population of cancer stem cells that are resistant to at least one or more different low dose chemotherapy agents.

Further, the inventors have discovered a method to identify miRNAs that contribute to cancer stem cells' self-proliferative capability and "stemness". As disclosed herein, the term "stemness" is defined below, and typically refers to the self-proliferative capacity of an immature or non-terminally differentiated cell, for example, the capacity of a cell to produce a daughter cell, which themselves can be induced to proliferate and produce progeny that subsequently differentiate into one or more mature cell types, while also retaining one or more cells with parental developmental potential.

Accordingly, the present invention provides methods to treat cancers by targeting cancer stem cells, the method comprising targeting the cancer stem cell with miRNAs or mimetics thereof to increase the levels of miRNAs which are reduced or lacking in cancer stem cells as compared to non-stem cell cancer cells. As a non-limiting example, the present invention provides methods to treat and prevent cancers by targeting cancer stem cells with let-7 miRNA, and/or a mimetic thereof, to increase levels of let-7 miRNA in the cancer stem cell. An increase in let-7 miRNA in the cell will increase let-7 mediated gene silencing in the cancer stem cell, which will cause a reduction in the self-renewal and proliferative capacity and/or differentiation capacity of a cancer stem cell to a less malignant cell. In some embodiments, any form of let-7 can be used in the methods as disclosed herein, for example any nucleic acid or any agent which has a minimum biological activity of binding to and inhibiting the let-7 target sequence 5'-AACTATACAACC-TACTACCTCA-3' (SEQ ID NO: 9). In some embodiments, one can use let-7a, and in alternative embodiments, let-7 miRNA can be in the form of any of the following, but not limited to, let-7 pre-miRNA, let-7 pri-miRNA or mature let-7 miRNA or homologues, fragments and variants thereof that retain a gene regulatory biological activity of the mature let-7 miRNA, especially the ability to down-regulate the expression of a target gene by miRNA-mediated gene silencing.

In alternative embodiments, cancers can be treated by targeting the cancer stem cell with any one or a combination of the following miRNAs and mimetics thereof: miR-107; miR-10a; miR-128a; miR128b; miR-132; miR-138; miR-16; miR-17; miR-195; miR-199a; miR-20; miR-200a; miR-200b; miR-200c; miR-20b and miR-22.

In some embodiments, the invention provides methods to treat cancers by targeting cancer cells with a plurality of different miRNA and/or miRNA mimetics to increase the levels of more than one miRNA that are reduced or lacking in the cancer stem cells compared with non-stem cell cancer cells.

Conversely, the inventors have also discovered that cancer stem cells have increased expression of other specific miRNAs as compared with normal tissue and non-stem cell cancer cells. For example, the inventors have discovered that cancer stem cells have an increased level of expression of at least the following miRNA's: miRNAs miR-129; miR-140; miR-184; and miR-198. Accordingly, the present invention also provides methods to treat cancers by targeting cancer stem cells, the method comprising targeting the cancer stem cell with agents which inhibit the expression of miRNAs which are increased or elevated in the cancer stem cells as compared with non-stem cell cancer cells. As a non-limiting example, the invention provides methods to treat cancers by targeting cancer stem cells with an agent that inhibits the activity and/or expression of miR-198 to reduce levels of miR-198 miRNA in the cancer stem cell. Such an agent can be an inhibitory nucleic acid molecule, for example but not limited to antisense nucleic acid molecules and RNA-interference molecules such as siRNA, etc.

Therefore in some embodiments, the methods of the present invention relate to the treatment of cancers by targeting cancer stem cells, the method comprising upregulating miRNAs that are reduced or lacking in cancer stem cells. As a non-limiting example, let-7 miRNAs can be upregulated by providing, pharmaceutical compositions comprising let-7 miRNA and/or let-7 mimetics to a cancer stem cell in a therapeutically effective amount for the treatment of cancer. In such embodiments, the cancer comprises a cancer stem cell and/or a cell with reduced or lacking let-7 expression.

In some embodiments, the pharmaceutical composition comprising miRNA or mimetics thereof, for example let-7 and/or let-7 mimetics is administered with, at the same time, or sequential to another agent or therapy, for example a cancer therapy. Such additional agents include, but are not limited to, surgery, chemotherapy, radiotherapy, thermotherapy, immunotherapy, hormone therapy and laser therapy.

Another aspect of the invention relates to use of let-7 miRNA and/or let-7 mimetics as diagnostics and as therapeutics. In some embodiments, let-7 miRNAs and/or let-7 mimetics are administered to a subject in a pharmaceutical composition where the subject has a cancer stem cell. The administration can be a treatment and/or prophylaxis for cancer, where the subject has at least one cancer stem cell. The subject can have, or not have, symptoms or manifestation of cancer, since cancer stem cells can exist in the absence of symptoms of cancer. In some embodiments, the pharmaceutical compositions comprising let-7 miRNA and/or let-7 mimetics are administered to a subject with a cancer stem cell.

The cancer stem cell can be present in any type of cancer including, for example breast cancer. In some embodiments, the cancer is a treatment-resistant cancer, for example, but not limited to a cancer which is resistant to chemotherapy, such as a chemotherapy-resistant breast cancer.

In another aspect of the present invention, methods are provided to treat cancers by targeting the cancer stem cells, the method comprising targeting the cancer stem cell with agents that inhibit genes and/or their gene products (i.e. mRNAs or proteins) which are normally gene silenced by the miRNAs that are reduced in the cancer stem cells, for example, genes that are gene silenced by let-7 miRNA. Such genes that are regulated by miRNA are genes which comprise miRNA target sequences in their mRNA. For example, genes silenced by let-7 comprise a let-7 target sequence within their mRNA. The let-7 target sequence can be in the 5'UTR, 3'UTR or coding sequence. Examples of such genes that comprise a let-7 target sequence in their mRNA include, but are not limited to, RAS, HRAS, KRAS, lin-42, GRB2, hbl-1, daf-12 and pha-4, or human homologues thereof. In some embodiments, agents inhibit the activity and/or the expression of genes that are gene silenced by miRNAs that are reduced or lacking on cancer stem cells. As a non-limiting example, in some embodiments an agent inhibits the activity and/or expression of genes comprising let-7 target sequence within their mRNA.

In some embodiments, the methods of the present intervention relate to the treatment of cancers by targeting cancer stem cells, the method comprising administering a pharmaceutical composition comprising at least one agent that inhibits the activity and/or the expression of at least one gene that is gene silenced by miRNA that are reduced or lacking in cancer stem cells. As a non-limiting example, a pharmaceutical composition comprising at least one agent that inhibits the activity and/or the expression of at least one gene that is gene silenced by let-7 and/or comprises a let-7 target within their mRNA is administered to a cancer stem cell in a therapeutically effective amount for the treatment of cancer. In such embodiments, the cancer comprises a cancer stem cell and/or a cell with reduced or lacking let-7 expression.

In another aspect of the present invention, methods for diagnosing whether a subject is at risk of having or has a metastasis or a malignant cancer are provided. In some embodiments, the methods comprise assessing the level of let-7 in a biological sample from the subject, and if the level of let-7 is below a reference level, the subject is identified as being at risk of having a metastasis and/or malignant cancer. In some embodiments, the biological sample is from a cancer biopsy. In some embodiments, the cancer biopsy is a breast cancer biopsy. In such embodiments, if the level of let-7 in the biological sample obtained from the subject is below the reference level, the subject is administered a pharmaceutical compositions comprising let-7 miRNA and/or a let-7 mimetic.

In another embodiment, the cancer to be treated is any cancer that comprises cancer stem cells. In alternative embodiments, the cancer to be treated is any cancer characterized by reduced expression and/or lack of let-7 miRNA expression. In some embodiments, the cancer is breast cancer. In some embodiments, the cancer is a resistant cancer, for example a multi-drug and/or chemotherapy-resistant cancer. In some embodiments, the cancer is lung or colon cancer.

In some embodiments, the let-7 miRNA are nucleic acids, include but not limited to let-7 pri miRNA, let-7 pre-miRNA, mature let-7 miRNA or homologues, fragments or variants thereof that retain the biological activity of the mature let-7 miRNA.

In alternative embodiments, mimetics of let-7 miRNA are useful in the methods of the present invention. A let-7 mimetic is an entity or agent that functions as a let-7 miRNA, for example, a nucleic acid or agent which has a minimum biological activity of binding to and inhibiting expression of a gene comprising the let-7 target sequence 5'-AACTATACAACCTACTACCTCA-3' (SEQ ID NO: 9). Examples of let-7 mimetics include, but are not limited to, small molecules, proteins, nucleic acids, ribosomes, aptamers, antibodies and nucleic acid analogues that mimic let-7 miRNA. Nucleic acid let-7 mimetics can also include, but are not limited to, RNA interference-inducing molecules (RNAi), including but not limited to, siRNA, dsRNA, stRNA, shRNA and modified versions thereof, where the RNA interference (RNAi) molecule has a minimum biological activity of binding to and inhibiting the expression of a gene comprising the let-7 target sequence 5'-AACTATACAACCTACTACCTCA-3' (SEQ ID NO: 9).

Effective, safe dosages can be experimentally determined in model organisms and in human trials by methods well known to one of ordinary skill in the art. The let-7 miRNA and/or let-7 mimetics in a pharmaceutical composition can be administered alone or in combination with adjuvant cancer therapy such as surgery, chemotherapy, radiotherapy, thermotherapy, immunotherapy, hormone therapy and laser therapy, to provide a beneficial effect, e.g. reduce tumor size, reduce cell proliferation of the tumor, inhibit angiogenesis, inhibit metastasis, or otherwise improve at least one symptom or manifestation of the disease.

Another aspect of the invention provides methods for the enrichment of cancer stem cells. The method relates to sequential passaging of cancer cells in vivo when exposed to low dose chemotherapy.

In another embodiment, the present invention provides methods to identify miRNAs that contribute to the self-proliferative capacity and/or tumorogenicity of a cancer stem cell. In some embodiments, the method comprises comparing the miRNA expression profile of a cancer stem cell enriched by the methods as disclosed herein, with the miRNA expression profile of a reference sample, such as, but not limiting to an expression profile of a non-stem cancer cell. A change in a miRNA in the cancer stem cell as compared with a reference sample identifies a miRNA that contributes, in whole or in part, to the self-proliferative capacity and/or tumorogenicity of the cancer stem cell. In further embodiments, the present invention provides methods to assess the role and level of such contribution of the identified miRNA to the cancer stem cells self-proliferative capability, the method comprising either introducing or inhibiting the miRNA in the cancer stem cell, depending upon whether the miRNA being assessed is downregulated or upregulated respectively, in the cancer stem cell as compared with the reference sample.

Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

As used herein, the term "let-7" refers to a nucleic acid or an agent which has a minimum biological activity of binding to (or hybridizing to) and inhibiting the expression of a gene comprising the let-7 target sequence, where the target sequence is 5'-AACTATACAACCTACTACCTCA-3' (SEQ ID NO: 9). A let-7 can be assessed for its ability to bind to and inhibit the target sequence SEQ ID NO:9 using the let-7 luciferase assay as disclosed herein in the Examples, for example by using the pMIR-REPORT™ luciferase reporter vector with a let-7 target sequence (SEQ ID NO: 9) (as well as SEQ ID NO:10 and SEQ ID NO:11) cloned into its 3'UTR. let-7 can refer to a nucleic acid encoding a let-7 miRNA corresponding to SEQ ID NO: 1. "let-7" also refers to a nucleic acid encoding a let-7 miRNA or homologues and variants of SEQ ID NO: 1, including conservative substitutions, additions, and deletions therein which do not adversely affect the structure or function, and where such homologues and variants have the same function or same activity of let-7 encoded by SEQ ID NO:1 and are capable of binding to and inhibiting the expression of a gene comprising the let-7 target sequence 5'-AACTATACAACC-TACTACCTCA-3' (SEQ ID NO: 9). Preferably, let-7 refers to the nucleic acid encoding let-7 from *C. elegans* (NCBI Accession No. AY390762), and in some embodiments, let-7 refers to the nucleic acid encoding a let-7 family member from humans, including but not limited to, NCBI Accession Nos. AJ421724, AJ421725, AJ421726, AJ421727, AJ421728, AJ421729, AJ421730, AJ421731, AJ421732, and functional or biologically active sequence variants of let-7, including alleles, and in vitro generated derivatives of let-7 that demonstrate let-7 activity. The term "let-7 family" includes let-7 homologues and isoforms, for example but not limited to let-7 family members including let-7a (SEQ ID NO:1); let-7b (SEQ ID NO:2); hsa-let-7c (SEQ ID NO:3); hsa-let-7d (SEQ ID NO:4); hsa-let-7e (SEQ ID NO:5); hsa-let-7f (SEQ ID NO:6).

A let-7 agent as also referred to herein also encompasses a "let-7 mimetic" and means an agent which binds to and inhibits the let-7 target sequence 5'-AACTATACAACC-TACTACCTCA-3' (SEQ ID NO: 9). In this context, a let-7 agent can be any agent or RNA interference-inducing molecule, for example but not limited to unmodified and modified double stranded (ds) RNA molecules including, short-temporal RNA (stRNA), small interfering RNA (siRNA), short-hairpin RNA (shRNA), microRNA (miRNA), double-stranded RNA (dsRNA). Alternatively, a let-7 agent can be a small molecule, protein, aptamer, nucleic acid analogue, antibody etc. that binds to and inhibits the let-7 target sequence SEQ ID NO:9; Activity of a let-7 agent can be assessed using, for example, the let-7 luciferase assay as disclosed herein in the Examples which uses the pMIR-REPORT™ luciferase reporter vector with a let-7 target sequence (SEQ ID NO: 9) cloned into its 3'UTR.

The terms "same activity" or "same function" as used in reference to the same activity or function of let-7 means a let-7 molecule which can bind to and inhibit the target sequence SEQ ID NO:9 with at least 80% of the efficiency, or greater efficiency, as the wild type let-7 (SEQ ID NO:1), as assessed using, for example, the let-7 luciferase assay as disclosed herein in the Examples.

The terms "microRNA" or "miRNA" used interchangeably herein, are endogenous RNAs, some of which are known to regulate the expression of protein-coding genes at the posttranscriptional level. As used herein, the term "microRNA" refers to any type of micro-interfering RNA, including but not limited to, endogenous microRNA and artificial microRNA. Typically, endogenous microRNA are small RNAs encoded in the genome which are capable of modulating the productive utilization of mRNA. A mature miRNA is a single-stranded RNA molecule of about 21-23 nucleotides in length which is complementary to a target sequence, and hybridizes to the target RNA sequence to inhibit expression of a gene which encodes a miRNA target sequence. miRNAs themselves are encoded by genes that are transcribed from DNA but not translated into protein (non-coding RNA); instead they are processed from primary transcripts known as pri-miRNA to short stem-loop structures called pre-miRNA and finally to functional miRNA. Mature miRNA molecules are partially complementary to one or more messenger RNA (mRNA) molecules, and their main function is to downregulate gene expression. MicroRNA sequences have been described in publications such as, Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into the precursor molecule.

A mature miRNA is produced as a result of a series of miRNA maturation steps; first a gene encoding the miRNA is transcribed. The gene encoding the miRNA is typically much longer than the processed mature miRNA molecule; miRNAs are first transcribed as primary transcripts or "pri-miRNA" with a cap and poly-A tail, which is subsequently processed to short, about 70-nucleotide "stem-loop structures" known as "pre-miRNA" in the cell nucleus. This processing is performed in animals by a protein complex known as the Microprocessor complex, consisting of the nuclease Drosha and the double-stranded RNA binding protein Pasha. These pre-miRNAs are then processed to mature miRNAs in the cytoplasm by interaction with the endonuclease Dicer, which also initiates the formation of the RNA-induced silencing complex (RISC). This complex is responsible for the gene silencing observed due to miRNA expression and RNA interference. The pathway is different for miRNAs derived from intronic stem-loops; these are processed by Drosha but not by Dicer. In some instances, a given region of DNA and its complementary strand can both function as templates to give rise to at least two miRNAs. Mature miRNAs can direct the cleavage of mRNA or they can interfere with translation of the mRNA, either of which results in reduced protein accumulation, rendering miRNAs capable of modulating gene expression and related cellular activities.

The term "pri-miRNA" refers to a precursor to a mature miRNA molecule which comprises; (i) a microRNA sequence and (ii) stem-loop component which are both flanked (i.e. surrounded on each side) by "microRNA flanking sequences", where each flanking sequence typically ends in either a cap or poly-A tail. A pri-microRNA, (also referred to as large RNA precursors), are composed of any type of nucleic acid based molecule capable of accommodating the microRNA flanking sequences and the microRNA sequence. Examples of pri-miRNAs and the individual components of such precursors (flanking sequences and microRNA sequence) are provided herein. The nucleotide sequence of the pri-miRNA precursor and its stem-loop components can vary widely. In one aspect a pre-miRNA molecule can be an isolated nucleic acid; including microRNA flanking sequences and comprising a stem-loop structure and a microRNA sequence incorporated therein. A pri-miRNA molecule can be processed in vivo or in vitro to an intermediate species caller "pre-miRNA", which is further processed to produce a mature miRNA.

The term "pre-miRNA" refers to the intermediate miRNA species in the processing of a pri-miRNA to mature miRNA, where pri-miRNA is processed to pre-miRNA in the nucleus, where upon pre-miRNA translocates to the cytoplasm where it undergoes additional processing in the cytoplasm to form mature miRNA. Pre-miRNAs are generally about 70 nucleotides long, but can be less than 70 nucleotides or more than 70 nucleotides.

The term "microRNA flanking sequence" as used herein refers to nucleotide sequences including microRNA processing elements. MicroRNA processing elements are the minimal nucleic acid sequences which contribute to the production of mature miRNA from precursor microRNA. Often these elements are located within a 40 nucleotide sequence that flanks a microRNA stem-loop structure. In some instances the microRNA processing elements are found within a stretch of nucleotide sequences of between 5 and 4,000 nucleotides in length that flank a microRNA stem-loop structure. Thus, in some embodiments the flanking sequences are 5-4,000 nucleotides in length. As a result, the length of the precursor molecule can be, in some instances at least about 150 nucleotides or 270 nucleotides in length. The total length of the precursor molecule, however, can be greater or less than these values. In other embodiments the minimal length of the microRNA flanking sequence is 10, 20, 30, 40, 50, 60, 70, 80, 90, 100, 150, 200 and any integer there between. In other embodiments the maximal length of the microRNA flanking sequence is 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900 4,000 and any integer there between.

MicroRNA flanking sequences can be native microRNA flanking sequences or artificial microRNA flanking sequences. A native microRNA flanking sequence is a nucleotide sequence that is ordinarily associated in naturally existing systems with microRNA sequences, i.e., these sequences are found within the genomic sequences surrounding the minimal microRNA hairpin in vivo. Artificial microRNA flanking sequences are nucleotides sequences that are not found to be flanking to microRNA sequences in naturally existing systems. microRNA flanking sequences within the pri-miRNA molecule can flank one or both sides of the stem-loop structure encompassing the microRNA sequence. Thus, one end (i.e., 5') of the stem-loop structure can be adjacent to a single flanking sequence and the other end (i.e., 3') of the stem-loop structure can not be adjacent to a flanking sequence. Preferred structures have flanking sequences on both ends of the stem-loop structure. The flanking sequences can be directly adjacent to one or both ends of the stem-loop structure or can be connected to the stem-loop structure through a linker, additional nucleotides or other molecules.

A "stem-loop structure" refers to a nucleic acid having a secondary structure that includes a region of nucleotides which are known or predicted to form a double strand (stem portion) that is linked on one side by a region of predominantly single-stranded nucleotides (loop portion). The terms "hairpin" and "fold-back" structures are also used herein to refer to stem-loop structures. Such structures are well known in the art and the term is used consistently with its known meaning in the art. The actual primary sequence of nucleotides within the stem-loop structure is not critical to the practice of the invention as long as the secondary structure is present. As is known in the art, the secondary structure does not require exact base-pairing. Thus, the stem can include one or more base mismatches. Alternatively, the base-pairing can be exact, i.e. not include any mismatches. In some instances the precursor microRNA molecule can include more than one stem-loop structure. The multiple stem-loop structures can be linked to one another through a linker, such as, for example, a nucleic acid linker or by a microRNA flanking sequence or other molecule or some combination thereof.

Furthermore, miRNA-like stem-loops can be expressed in cells as a vehicle to deliver artificial miRNAs and short interfering RNAs (siRNAs) for the purpose of modulating the expression of endogenous genes through the miRNA and or RNAi pathways. As used herein, the term "miRNA mimetic" refers to an artificial miRNA or RNAi (RNA interference molecule) which is flanked by the stem-loop like structures of a pri-miRNA.

The term "artificial microRNA" includes any type of RNA sequence, other than endogenous microRNA, which is capable of modulating the productive utilization of mRNA. For instance, the term artificial microRNA also encompasses a nucleic acid sequence which would be previously identified as siRNA, where the siRNA is incorporated into a vector and surrounded by miRNA flanking sequences as described herein.

As used herein, "double stranded RNA" or "dsRNA" refers to RNA molecules that are comprised of two substantially complementary strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 116:281-297), comprises a dsRNA molecule.

As used herein, "gene silencing" or "gene silenced" by a miRNA and/or RNA interference molecule "refers to a decrease in the mRNA level in a cell for a target gene by at least about 5%, at least about 10%, at least about 20%, at least about 30%, at least about 40%, at least about 50%, at least about 60%, at least about 70%, at least about 80%, at least about 90%, at least about 95%, at least about 99% up to and including 100%, and any integer in between of the mRNA level found in the cell without the presence of the miRNA or RNA interference molecule. In one preferred embodiment, the mRNA levels are decreased by at least about 70%, at least about 80%, at least about 90%, at least about 95%, at least about 99%, up to and including 100% and any integer in between 5% and 100%."

The term "reduced" or "reduce" as used herein generally means a decrease by a statistically significant amount. However, for avoidance of doubt, "reduced" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

The term "lacking" or "lack of" when used in the context of the expression of let-7 herein, refers to a level let-7 which is undetectable by the methods as used herein to measure such levels. The term "lack of" typically refers to minimal, absent or about null levels of let-7 expression, but does not necessarily mean let-7 is completely absent, it means the level of let-7 in a cell is below a level for a significant let-7 target gene silencing in that cell.

The term "increased" or "increase" as used herein generally means an increase by a statically significant amount; for the avoidance of any doubt, "increased" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The terms "enriching" or "enriched" are used interchangeably herein and mean that the yield (fraction) of cells of one type is increased by at least 10% over the fraction of cells of that type in the starting culture or preparation.

The term "tissue" refers to a group or layer of similarly specialized cells which together perform certain special functions. The term "tissue-specific" refers to a source of cells from a specific tissue.

The term "substantially pure", with respect to a particular cell population, refers to a population of cells that is at least about 75%, preferably at least about 85%, more preferably at least about 90%, and most preferably at least about 95% pure, with respect to the cells making up a total cell population. Recast, the terms "substantially pure" or "essentially purified", with regard to a preparation of one or more partially and/or terminally differentiated cell types, refer to a population of cells that contain fewer than about 20%, more preferably fewer than about 15%, 10%, 8%, 7%, most preferably fewer than about 5%, 4%, 3%, 2%, 1%, or less than 1%, of cells that are not stem cells or stem cell progeny.

The term "stem cell" as used herein, as used in the context of or with reference to a "cancer stem cell" refers to an undifferentiated cell which is capable of proliferation and giving rise to more progenitor cells having the ability to generate a large number of mother cells that can in turn give rise to differentiated, or differentiable daughter cells. The daughter cells themselves can be induced to proliferate and produce progeny that subsequently differentiate into one or more mature cell types, while also retaining one or more cells with parental developmental potential. The term "cancer stem cell" refers then, to a cell with the capacity or potential, under particular circumstances, to differentiate to a more specialized or differentiated phenotype, and which retains the capacity, under certain circumstances, to proliferate without substantially differentiating. In one embodiment, the term progenitor or stem cell refers to a generalized mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell can derive from a multipotent cell which itself is derived from a multipotent cell, and so on. While each of these multipotent cells can be considered stem cells, the range of cell types each can give rise to can vary considerably. Some differentiated cells also have the capacity to give rise to cells of greater developmental potential. Such capacity can be natural or can be induced artificially upon treatment with various factors. In many biological instances, stem cells are also "multipotent" because they can produce progeny of more than one distinct cell type, but this is not required for "stemness." Self-renewal is the other classical part of the stem cell definition, and it is essential as used in this document. In theory, self-renewal can occur by either of two major mechanisms. Stem cells can divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Formally, it is possible that cells that begin as stem cells might proceed toward a differentiated phenotype, but then "reverse" and re-express the stem cell phenotype, a term often referred to as "dedifferentiation". Cancer stem cells have the ability for self-renewal, multipotent differentiation and vigorous proliferative capacity, as well as the ability to form mammospheres (or emboid bodies). In some embodiments, breast cancer stem cells are also positive for breast cancer stem cell phenotype (Oct4$^+$CD44$^+$CD24$^-$lineage$^-$)[1]

The term "progenitor cells" is used synonymously with "stem cell." Generally, "progenitor cells" have a cellular phenotype that is more primitive (i.e., is at an earlier step along a developmental pathway or progression) than is a fully differentiated cell. Often, progenitor cells also have significant or very high proliferative potential. Progenitor cells can give rise to multiple distinct differentiated cell types or to a single differentiated cell type, depending on the developmental pathway and on the environment in which the cells develop and differentiate. It is possible that cells that begin as progenitor cells might proceed toward a differentiated phenotype, but then "reverse" and re-express the progenitor cell phenotype.

In the context of cell ontogeny, the adjective "differentiated", or "differentiating" is a relative term. A "differentiated cell" is a cell that has progressed further down the developmental pathway than the cell it is being compared with. Thus, stem cells can differentiate to lineage-restricted precursor cells (such as a mesodermal stem cell), which in turn can differentiate into other types of precursor cells further down the pathway, and then to an end-stage differentiated cell, which plays a characteristic role in a certain tissue type, and can or can not retain the capacity to proliferate further.

As indicated above, there are different levels or classes of cells falling under the general definition of a "stem cell." These are "totipotent," "pluripotent" and "multipotent" stem cells. The term "totipotent" refers to a stem cell that can give rise to any tissue or cell type in the body. "Pluripotent" stem cells can give rise to any type of cell in the body except germ line cells. Stem cells that can give rise to a smaller or limited number of different cell types are generally termed "multipotent." Thus, totipotent cells differentiate into pluripotent cells that can give rise to most, but not all, of the tissues necessary for fetal development. Pluripotent cells undergo further differentiation into multipotent cells that are committed to give rise to cells that have a particular function. For example, multipotent hematopoietic stem cells give rise to the red blood cells, white blood cells and platelets in the blood.

The term "stemness" as used herein refers to a cell with stem cell properties, for example a cell that has the capacity for self-renewal, for example a cell that is totipotent, pluripotent or multipotent. A cancer cell that is a "cancer stem cell" or a cancer cell with stemness properties is a cancer cell which can give rises to daughter cells which themselves can be induced to proliferate and produce progeny that subsequently differentiate into one or more mature cell types, while also retaining one or more cells with parental developmental potential. The term "cancer stem cell" therefore refers to a cell with the capacity or potential, under particular circumstances, to differentiate to a more specialized or differentiated phenotype, and which retains the capacity, under certain circumstances, to proliferate without substantially differentiating the self-renewal potential of breast tumor-initating cells can be determined by their capacity to give rise to mammospheres[10] or emboid bodies in vitro. Furthermore, self-renewing breast cancer cells have been shown to be $CD44^+CD24^{-9,10,15}$, as demonstrated in Example 1 herein. Cancer stem cells have the ability for self-renewal, multipotent differentiation and vigorous proliferative capacity, as well as the ability to form mammospheres (or emboid bodies).

As used herein a "siRNA" refers to a nucleic acid that forms a double stranded RNA, which double stranded RNA has the ability to reduce or inhibit expression of a particular gene or target gene when the siRNA is expressed in the same cell as the gene or target gene. The double stranded RNA siRNA can be formed by the complementary strands. The complementary portions of the siRNA that hybridize to form the double stranded molecule typically have substantial or complete identity. In one embodiment, a siRNA refers to a nucleic acid that has substantial or complete identity to sequence of a target gene and forms a double stranded RNA. The sequence of the siRNA can correspond to the full length target gene, or to a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The term "biological sample" as used herein means a sample of biological tissue or fluid that comprises nucleic acids. Such samples include, but are not limited to, tissue isolated from animals. Biological samples can also include sections of tissues such as biopsy and autopsy samples, frozen sections taken for histologic purposes, blood, plasma, serum, sputum, stool, tears, mucus, hair, and skin. Biological samples also include explants and primary and/or transformed cell cultures derived from patient tissues. A biological sample can be provided by removing a sample of cells from an animal, but can also be accomplished by using previously isolated cells (e.g., isolated by another person, at another time, and/or for another purpose), or by performing the methods as disclosed herein in vivo. Archival tissues, such as those having treatment or outcome history can also be used.

The term "tissue" is intended to include, blood, blood preparations such as plasma and serum, bones, joints, muscles, smooth muscles, and organs.

The terms "disease" or "disorder" are used interchangeably herein, and refer to any alteration in state of the body or of some of the organs, interrupting or disturbing the performance of the functions and/or causing symptoms such as discomfort, dysfunction, distress, or even death to the person afflicted or those in contact with a person. A disease or disorder can also related to a distemper, ailing, ailment, malady, disorder, sickness, illness, complaint, indisposition or affliction.

The terms "subject" and "individual" are used interchangeably herein, and refer to an animal, for example a human, to whom treatment, including prophylactic treatment, with a pharmaceutical composition as disclosed herein, is provided. The term "subject" as used herein refers to human and non-human animals. The term "non-human animals" and "non-human mammals" are used interchangeably herein and includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model.

The term 'effective amount" as used herein refers to the amount of therapeutic agent of pharmaceutical composition to alleviate at least one of the symptoms of the disease or disorder.

The terms "malignancy" and "cancer" are used interchangeably herein and refers to any disease of an organ or tissue in mammals characterized by poorly controlled or uncontrolled multiplication of normal or abnormal cells in that tissue which results in a tumor and has an effect on the body as a whole. Cancer diseases within the scope of the definition comprise benign neoplasms, dysplasias, hyperplasias as well as neoplasms showing metastatic growth or any other transformations like e.g. leukoplakias which often precede a breakout of cancer.

As used herein, the term "tumor" refers to a mass of transformed cells that are characterized, at least in part, by containing angiogenic vasculature. The transformed cells are characterized by neoplastic uncontrolled cell multiplication which is rapid and continues even after the stimuli that initiated the new growth has ceased. The term "tumor" is used broadly to include the tumor parenchymal cells as well as the supporting stroma, including the angiogenic blood vessels that infiltrate the tumor parenchymal cell mass. Although a tumor generally is a malignant tumor, i.e., a cancer having the ability to metastasize (i.e. a metastatic tumor), a tumor also can be nonmalignant (i.e. non-metastatic tumor). Tumors are hallmarks of cancer, a neoplastic disease the natural course of which is fatal. Cancer cells exhibit the properties of invasion and metastasis and are highly anaplastic.

As used herein, the term "metastases" or "metastatic tumor" refers to a secondary tumor that grows separately elsewhere in the body from the primary tumor and has arisen from detached, transported cells, wherein the primary tumor is a solid tumor. The primary tumor, as used herein, refers to a tumor that originated in the location or organ in which it is present and did not metastasize to that location from another location. As used herein, a "malignant tumor" is one having the properties of invasion and metastasis and showing a high degree of anaplasia. Anaplasia is the reversion of cells to an immature or a less differentiated form, and it occurs in most malignant tumors.

The term "therapy resistant cancer" as used herein refers to a cancer present in a subject which is resistant to, or refractory to at least two different anti-cancer agents such as chemotherapy agents, which means, typically a subject has been treated with at least two different anti-cancer agents that did not provide effective treatment as that term is defined herein.

The term "gene" as used herein refers to a genomic gene comprising transcriptional and/or translational regulatory sequences and/or a coding region and/or non-translated sequences (e.g., introns, 5'- and 3'-untranslated sequences). The coding region of a gene can be a nucleotide sequence coding for an amino acid sequence or a functional RNA, such as tRNA, rRNA, catalytic RNA, siRNA, miRNA and antisense RNA. A gene can also be an mRNA or cDNA corresponding to the coding regions (e.g., exons and miRNA) optionally comprising 5'- or 3' untranslated sequences linked thereto. A gene can also be an amplified nucleic acid molecule produced in vitro comprising all or a part of the coding region and/or 5'- or 3'-untranslated sequences linked thereto.

The term "nucleic acid" or "oligonucleotide" or "polynucleotide" used herein means at least two nucleotides covalently linked together. As will be appreciated by those in the art, the depiction of a single strand also defines the sequence of the complementary strand. Thus, a nucleic acid also encompasses the complementary strand of a depicted single strand. As will also be appreciated by those in the art, many variants of a nucleic acid can be used for the same purpose as a given nucleic acid. Thus, a nucleic acid also encompasses substantially identical nucleic acids and complements thereof. As will also be appreciated by those in the art, a single strand provides a probe that can hybridize to the target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

A nucleic acid will generally contain phosphodiester bonds, although nucleic acid analogs can be included that can have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog can be located for example at the 5'-end and/or the 3'-end of the nucleic acid molecule. Representative examples of nucleotide analogs can be selected from sugar- or backbone-modified ribonucleotides. It should be noted, however, that also nucleobase-modified ribonucleotides, i.e. ribonucleotides, containing a non naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e. g. 7 deaza-adenosine; O- and N-alkylated nucleotides, e.g. N6-methyl adenosine are suitable. The 2' OH— group can be replaced by a group selected from H. OR, R. halo, SH, SR, NH2, NHR, NR2 or CN, wherein R is C-C6 alkyl, alkenyl or alkynyl and halo is F. Cl, Br or I. Modifications of the ribose-phosphate backbone can be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs can be made.

The term "probe" as used herein refers to an oligonucleotide capable of binding to a target nucleic acid of complementary sequence through one or more types of chemical bonds, usually through complementary base pairing, usually through hydrogen bond formation. Probes can bind target sequences lacking complete complementarily with the probe sequence depending upon the stringency of the hybridization conditions. There can be any number of base pair mismatches which will interfere with hybridization between the target sequence and single stranded target nucleic acids, but a probe will bind a selected target specifically, i.e. to the substantial exclusion of non-target nucleic acids under at least one set of conditions. A probe can be single stranded or partially single and partially double stranded. A probe will generally be detectably labeled or carry a moiety that permits signal detection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, for example, by the local homology algorithm of Smith and Waterman (Adv. Appl. Math. 2:482 (1981), which is incorporated by reference herein), by the homology alignment algorithm of Needleman and Wunsch (J. Mol. Biol. 48:443-53 (1970), which is incorporated by reference herein), by the search for similarity method of Pearson and Lipman (Proc. Natl. Acad. Sci. USA 85:2444-48 (1988), which is incorporated by reference herein), by computerized implementations of these algorithms (e.g., GAP, BESTFIT, FASTA, and TFASTA in the Wisconsin Genetics Software Package, Genetics Computer Group, 575 Science Dr., Madison, Wis.), or by visual inspection. (See generally Ausubel et al. (eds.), Current Protocols in Molecular Biology, 4th ed., John Wiley and Sons, New York (1999)).

One example of a useful algorithm is PILEUP. PILEUP creates a multiple sequence alignment from a group of related sequences using progressive, pairwise alignments to show the percent sequence identity. It also plots a tree or dendogram showing the clustering relationships used to create the alignment. PILEUP uses a simplification of the progressive alignment method of Feng and Doolittle (J. Mol. Evol. 25:351-60 (1987), which is incorporated by reference herein). The method used is similar to the method described by Higgins and Sharp (Comput. Appl. Biosci. 5:151-53 (1989), which is incorporated by reference herein). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of an algorithm that is suitable for determining percent sequence identity and sequence similarity is the BLAST algorithm, which is described by Altschul et al. (J. Mol. Biol. 215:403-410 (1990), which is incorporated by reference herein). (See also Zhang et al., Nucleic Acid Res. 26:3986-90 (1998); Altschul et al., Nucleic Acid Res. 25:3389-402 (1997), which are incorporated by reference herein). Software for performing BLAST analyses is publicly available through the National Center for Biotechnology Information internet web site. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990), supra). These initial neighborhood word hits act as seeds for initiating searches to find longer HSPs containing them. The word hits are then extended in both directions along each sequence for as far as the cumulative alignment score can be increased. Extension of the word hits in each direction is halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff and Henikoff, Proc. Natl. Acad. Sci. USA 89:10915-9 (1992), which is incorporated by reference herein) alignments (B) of 50, expectation (E) of 10, M=5, N=−4, and a comparison of both strands.

In addition to calculating percent sequence identity, the BLAST algorithm also performs a statistical analysis of the similarity between two sequences (see, e.g., Karlin and Altschul, Proc. Natl. Acad. Sci. USA 90:5873-77 (1993), which is incorporated by reference herein). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more typically less than about 0.01, and most typically less than about 0.001.

The term "variant" as used in the context of let-7 miRNA variants means a modified let-7 miRNA with at least on of the following; altered nucleic acid sequence, such as insertions, deletions, substitutions, fragments of at least 5 nucleic acids, modification of the nucleic acids or nucleic acid analogues as compared to the wild type mature let-7 miRNA (SEQ ID NO:1).

As used herein, the terms "homologous" or "homologues" are used interchangeably, and when used to describe a polynucleotide or polypeptide, indicates that two polynucleotides or polypeptides, or designated sequences thereof, when optimally aligned and compared, for example using BLAST, version 2.2.14 with default parameters for an alignment (see below) are identical, with appropriate nucleotide insertions or deletions or amino-acid insertions or deletions, in at least 70% of the nucleotides, usually from about 75% to 99%, and more preferably at least about 98 to 99% of the nucleotides. The term "homolog" or "homologous" as used herein also refers to homology with respect to structure and/or function. With respect to sequence homology, sequences are homologs if they are at least 50%, at least 60 at least 70%, at least 80%, at least 90%, at least 95% identical, at least 97% identical, or at least 99% identical. The term "substantially homologous" refers to sequences that are at least 90%, at least 95% identical, at least 97% identical or at least 99% identical. Homologous sequences can be the same functional gene in different species.

Determination of homologs of the genes or peptides of the present invention can be easily ascertained by the skilled artisan. The terms "homology", "identity" and "similarity" refer to the degree of sequence similarity between two peptides or between two optimally aligned nucleic acid molecules. Homology and identity can each be determined by comparing a position in each sequence which can be aligned for purposes of comparison. When an equivalent position in the compared sequences is occupied by the same base or amino acid, then the molecules are identical at that position; when the equivalent site occupied by similar amino acid residues (e.g., similar in steric and/or electronic nature such as, for example conservative amino acid substitutions), then the molecules can be referred to as homologous (similar) at that position. Expression as a percentage of homology/similarity or identity refers to a function of the number of similar or identical amino acids at positions shared by the compared sequences, respectfully. A sequence which is "unrelated" or "non-homologous" shares less than 40% identity, though preferably less than 25% identity with a sequence of the present application.

As used herein, the term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T. C, G. U. or 1) or residue occurs in both sequences to yield the number of matched positions, dividing the number of matched positions by the total number of positions in the comparison window (i.e., the window size), and multiplying the result by 100 to yield the percentage of sequence identity.

The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the; percentage of sequence identity is calculated by comparing the reference sequence to the sequence which can include deletions or additions which total 20 percent or less of the reference sequence over the comparison window. The reference sequence can be a subset of a larger sequence. The term "similarity", when used to describe a polypeptide, is determined by comparing the amino acid sequence and the conserved amino acid substitutes of one polypeptide to the sequence of a second polypeptide.

As used herein, the term "expression profile" refers to the amount or level of a plurality of different miRNAs expressed in a cell or a population of cells or a tissue.

The term "target" as used herein refers to a polynucleotide that can be bound by one or more probes under stringent hybridization conditions. The term "targeting" as used herein in the context of "targeting a cancer cell" means directing a therapeutic agent as disclosed herein, such as a let-7 miRNA or homologues thereof to that cancer cell to treat a cancer compring such a cancer stem cell.

The term "target cell" as used herein refers to a cell which comprises cell surface antigens, such as for example but not limited to, cell surface receptors or glycoprotein or other cell surface markers which the targeting moiety as disclosed herein can recognize and bind thereto.

The terms "targeting moiety" or "target moiety" are used interchangeably herein and refer to a molecule which has affinity for, or binds to a molecule on the surface of a target cell, for example a targeting moiety functions as an agent that homes in on or preferentially associates or binds to a particular tissue, cell type, receptor, infecting agent or other area of interest. Examples of a targeting moiety include, but are not limited to, an antibody, an antigen binding fragment of an antibody, an antigen, a ligand, a receptor, one member of a specific binding pair, a polyamide including a peptide having affinity for a biological receptor, an oligosaccharide, a polysaccharide, a steroid or steroid derivative, a hormone, e.g., estradiol or histamine, a hormone-mimic, e.g., morphine, or other compound having binding specificity for a cellular target. In the methods of the present invention, a targeting moiety promotes transport or preferential localization of the let-7 miRNA to a target cell, for example a target cancer stem cell. Targeting moiety useful in the methods and compositions as disclosed herein binds to cell-surface antigens or proteins present on cancer stem cells. Examples include, but are not limited to, tumor-associated antigens (TAAs), the HLA-DR antigen, c-erbB-2 proto-oncogene, MUC1, MAG-1, VEGFR2, pro-vasopressin (pro-VP), TAG-72 (sialyl Tn or STn), STn-KLH, GD3, cancer antigen 125 (CA 125, human ovarian cancer cell surface antigen. (OC-CSA), alpha fetoprotein (AFP), and other cancer cell surface antigens which are disclosed in, for example, US20030143237A1, which is incorporated herein by reference.

As used herein, the term "binding moiety" refers to a protein or the nucleic acid binding domain of a protein which has the ability to associate with or complex with nucleic acids such as let-7 miRNA as disclosed herein. In some embodiments, a binding moiety is complexed with a targeting moiety by any means commonly known by persons of ordinary skill in the art, for example but not limited to, fusion, chemical conjugation, van de Waals forces, and in some embodiments the binding moiety can be fused to the carboxy portion of the targeting moiety. The location of the targeting moiety may be either in the carboxyl-terminal or amino-terminal end of the construct or in the middle of the fusion protein. Alternatively, the fusion protein may comprise more than one miRNA binding moiety and one or more targeting moieties. In one embodiment, the binding moiety is the nucleic acid binding domain of a protein selected from the group of nucleic acid binding domains present in proteins selected from the group consisting of protamine, GCN4, Fos, Jun, TFIIS, FMRI, yeast protein HX, Vigillin, Merl, bacterial polynucleotide phosphorylase, ribosomal protein S3, and heat shock protein. In one embodiment, the binding moiety is the protein protamine or an nucleic acid-binding fragment of protamine.

The term "vectors" refers to a nucleic acid molecule capable of transporting another nucleic acid to which it has been linked; a plasmid is a species of the genus encompassed by "vector". The term "vector" typically refers to a nucleic acid sequence containing an origin of replication and other entities necessary for replication and/or maintenance in a host cell. Vectors capable of directing the expression of genes and/or nucleic acid sequence to which they are operatively linked are referred to herein as "expression vectors". In general, expression vectors of utility are often in the form of "plasmids" which refer to circular double stranded DNA loops which, in their vector form are not bound to the chromosome, and typically comprise entities for stable or transient expression or the encoded DNA. Other expression vectors can be used in the methods as disclosed herein for example, but are not limited to, plasmids, episomes, bacterial artificial chromosomes, yeast artificial chromosomes, bacteriophages or viral vectors, and such vectors can integrate into the host's genome or replicate autonomously in the particular cell. A vector can be a DNA or RNA vector. Other forms of expression vectors known by those skilled in the art which serve the equivalent functions can also be used, for example self replicating extrachromosomal vectors or vectors which integrates into a host genome.

As used herein, the terms "treat" or "treatment" or "treating" refers to both therapeutic treatment and prophylactic or preventative measures, wherein the object is to prevent or slow the development of the disease, such as slow down the development of a tumor, the spread of cancer, or reducing at least one effect or symptom of a condition, disease or disorder associated with inappropriate proliferation or a cell mass, for example cancer. Treatment is generally "effective" if one or more symptoms or clinical markers are reduced as that term is defined herein. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already diagnosed with cancer, as well as those likely to develop secondary tumors due to metastasis.

The term "effective amount" as used herein refers to the amount of therapeutic agent of pharmaceutical composition to alleviate at least one or more symptom of the disease or disorder, and relates to a sufficient amount of pharmacological composition to provide the desired effect. The phrase "therapeutically effective amount" as used herein, e.g., of an miRNA-related composition as disclosed herein means a sufficient amount of the composition to treat a disorder, at a reasonable benefit/risk ratio applicable to any medical treatment. The term "therapeutically effective amount" therefore refers to an amount of the composition as disclosed herein that is sufficient to effect a therapeutically or prophylacticly significant reduction in a symptom or clinical marker associated with a T-cell disease or a cancer-mediated condition when administered to a typical subject who has a T-cell disease or a cancer.

A therapeutically or prophylatically significant reduction in a symptom is, e.g. at least about 10%, at least about 20%, at least about 30%, at least about 40%, at least about 50%, at least about 60%, at least about 70%, at least about 80%, at least about 90%, at least about 100%, at least about 125%, at least about 150% or more in a measured parameter as compared to a control or non-treated subject. Measured or measurable parameters include clinically detectable markers of disease, for example, elevated or depressed levels of a biological marker, as well as parameters related to a clinically accepted scale of symptoms or markers for a disease or disorder. It will be understood, however, that the total daily usage of the compositions and formulations as disclosed herein will be decided by the attending physician within the scope of sound medical judgment. The exact amount required will vary depending on factors such as the type of disease being treated.

With reference to the treatment of a subject with a cancer, the term "therapeutically effective amount" refers to the amount that is safe and sufficient to prevent or delay the development and further growth of a tumor or the spread of metastases in cancer patients. The amount can thus cure or cause the cancer to go into remission, slow the course of cancer progression, slow or inhibit tumor growth, slow or inhibit tumor metastasis, slow or inhibit the establishment of secondary tumors at metastatic sites, or inhibit the formation of new tumor metastases. The effective amount for the treatment of cancer depends on the tumor to be treated, the severity of the tumor, the drug resistance level of the tumor, the species being treated, the age and general condition of the subject, the mode of administration and so forth. Thus, it is not possible to specify the exact "effective amount". However, for any given case, an appropriate "effective amount" can be determined by one of ordinary skill in the art using only routine experimentation. The efficacy of treatment can be judged by an ordinarily skilled practitioner, for example, efficacy can be assessed in animal models of cancer and tumor, for example treatment of a rodent with a cancer, and any treatment or administration of the compositions or formulations that leads to a decrease of at least one symptom of the cancer, for example a reduction in the size of the tumor or a slowing or cessation of the rate of growth of the tumor indicates effective treatment. In embodiments where the compositions are used for the treatment of cancer, the efficacy of the composition can be judged using an experimental animal model of cancer, e.g., wild-type mice or rats, or preferably, transplantation of tumor cells. When using an experimental animal model, efficacy of treatment is evidenced when a reduction in a symptom of the cancer, for example a reduction in the size of the tumor or a slowing or cessation of the rate of growth of the tumor occurs earlier in treated, versus untreated animals. By "earlier" is meant that a decrease, for example in the size of the tumor occurs at least 5% earlier, but preferably more, e.g., one day earlier, two days earlier, 3 days earlier, or more.

As used herein, the term "treating" when used in reference to a cancer treatment is used to refer to the reduction of a symptom and/or a biochemical marker of cancer, for example a reduction in at least one biochemical marker of cancer by at least about 10% would be considered an effective treatment. Examples of such biochemical markers of cancer include CD44, telomerase, TGF-α, TGF-β, erbB-2, erbB-3, MUC1, MUC2, CK20, PSA, CA125 and FOBT. A reduction in the rate of proliferation of the cancer cells by at least about 10% would also be considered effective treatment by the methods as disclosed herein. As alternative examples, a reduction in a symptom of cancer, for example, a slowing of the rate of growth of the cancer by at least about 10% or a cessation of the increase in tumor size, or a reduction in the size of a tumor by at least about 10% or a reduction in the tumor spread (i.e. tumor metastasis) by at least about 10% would also be considered as affective treatments by the methods as disclosed herein. In some embodiments, it is preferred, but not required that the therapeutic agent actually kill the tumor.

As used herein, the terms "administering," and "introducing" are used interchangeably herein and refer to the placement of the therapeutic agents as disclosed herein into a subject by a method or route which results in delivering of such agent(s) at a desired site. The compounds can be administered by any appropriate route which results in an effective treatment in the subject.

The phrases "parenteral administration" and "administered parenterally" as used herein mean modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebrospinal, and intrasternal injection and infusion. The phrases "systemic administration," "administered systemically", "peripheral administration" and "administered peripherally" as used herein mean the administration therapeutic compositions other than directly into a tumor such that it enters the animal's system and, thus, is subject to metabolism and other like processes.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent or encapsulating material, involved in maintaining the activity of or carrying or transporting the subject agents from one organ, or portion of the body, to another organ, or portion of the body. In addition to being "pharmaceutically acceptable" as that term is defined herein, each carrier must also be "acceptable" in the sense of being compatible with the other ingredients of the formulation. The pharmaceutical formulation contains a compound of the invention in combination with one or more pharmaceutically acceptable ingredients. The carrier can be in the form of a solid, semi-solid or liquid diluent, cream or a capsule. These pharmaceutical preparations are a further object of the invention. Usually the amount of active compounds is between 0.1-95% by weight of the preparation, preferably between 0.2-20% by weight in preparations for parenteral use and preferably between 1 and 50% by weight in preparations for oral administration. For the clinical use of the methods of the present invention, targeted delivery composition of the invention is formulated into pharmaceutical compositions or pharmaceutical formulations for parenteral administration, e.g., intravenous; mucosal, e.g., intranasal; enteral, e.g., oral; topical, e.g., transdermal; ocular, e.g., via corneal scarification or other mode of administration. The pharmaceutical composition contains a compound of the invention in combination with one or more pharmaceutically acceptable ingredients. The carrier can be in the form of a solid, semi-solid or liquid diluent, cream or a capsule.

The terms "composition" or "pharmaceutical composition" used interchangeably herein refer to compositions or formulations that usually comprise an excipient, such as a pharmaceutically acceptable carrier that is conventional in the art and that is suitable for administration to mammals, and preferably humans or human cells. Such compositions can be specifically formulated for administration via one or more of a number of routes, including but not limited to, oral, ocular parenteral, intravenous, intraarterial, subcutaneous, intranasal, sublingual, intraspinal, intracerebroventricular, and the like. In addition, compositions for topical (e.g., oral mucosa, respiratory mucosa) and/or oral administration can form solutions, suspensions, tablets, pills, capsules, sustained-release formulations, oral rinses, or powders, as known in the art are described herein. The compositions also can include stabilizers and preservatives. For examples of carriers, stabilizers and adjuvants, University of the Sciences in Philadelphia (2005) *Remington: The Science and Practice of Pharmacy with Facts and Comparisons,* 21st Ed.

The term "agent" refers to any entity which is normally not present or not present at the levels being administered to a cell, tissue or subject. Agent can be selected from a group comprising: chemicals; small molecules; nucleic acid sequences; nucleic acid analogues; proteins; peptides; aptamers; antibodies; or functional fragments thereof. A nucleic acid sequence can be RNA or DNA, and can be single or double stranded, and can be selected from a group comprising: nucleic acid encoding a protein of interest; oligonucleotides; and nucleic acid analogues; for example peptide-nucleic acid (PNA), pseudo-complementary PNA (pc-PNA), locked nucleic acid (LNA), etc. Such nucleic acid sequences include, but are not limited to nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide or fragment thereof can be any protein of interest, for example, but not limited to; mutated proteins; therapeutic proteins; truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, tribodies, humanized proteins, humanized antibodies, chimeric antibodies, modified proteins and fragments thereof. An gent can be applied to the media, where it contacts the cell and induces its effects. Alternatively, an agent can be intracellular as a result of introduction of a nucleic acid sequence encoding the agent into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

The articles "a" and "an" are used herein to refer to one or to more than one (i.e., to at least one) of the grammatical object of the article. By way of example, "an element" means one element or more than one element.

Other than in the operating examples, or where otherwise indicated, all numbers expressing quantities of ingredients or reaction conditions used herein should be understood as modified in all instances by the term "about." The term "about" when used in connection with percentages can mean±1%. The present invention is further explained in detail by the following examples, but the scope of the invention should not be limited thereto.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

Let-7 microRNA

The present invention relates in part to use of let-7 miRNA and/or mimetics thereof for the treatment of cancer. In some embodiments, the methods relate to the treatment of cancer by targeting cancer stem cells with let-7 miRNA and/or a mimetic thereof. In some embodiments, the let-7 is any isoform of let-7, including but not limited to let-7a. In another embodiment, the let-7 miRNA is a let-7 pre-miRNA, let-7 pri-miRNA or mature let-7 miRNA or fragments and variants thereof that retain the biological activity of the mature let-7 miRNA.

Let-7 microRNAs or let-7 miRNAs are endogenous RNAs which function as gene silencing molecules that regulate the expression of protein-coding genes that comprise a let-7 target sequence. Let-7 miRNAs function to repress the expression of genes at the posttranscriptional level. Let-7 target sites to which let-7 miRNA binds in its role as a gene silencer are typically in the mRNA of the target gene, and can be in the 5' UTR, the 3' UTR or in the coding region.

Micro RNAs (also referred to as "miRNAs") are small non-coding RNAs belonging to a class of regulatory molecules found in plants and animals. Without wishing to be bound by theory, miRNAs are thought to control gene expression by binding to complementary sites (herein referred to as "target sequences") on target messenger RNA (mRNA) transcripts. miRNAs often function as "gene silencers" to suppress or repress the expression of a target gene. miRNAs are generated from large RNA precursors (termed pri-miRNAs) that are processed in the nucleus into approximately 70 nucleotide pre-miRNAs, which fold into imperfect stem loop structures (Lee, Y., et al., Nature (2003) 425(6956):415-9) (See FIG. 7c). The pre-miRNAs undergo an additional processing step within the cytoplasm where mature miRNAs of 18-25 nucleotides in length are excised from one side of the pre-miRNA hairpin by an RNase III enzyme, Dicer (Hutvagner, G., et al., Science (2001) 12:12 and Grishok, A., et al., Cell (2001) 106(1):23-34).

MiRNAs have been shown to regulate gene expression in two ways. First, miRNAs that bind to protein-coding mRNA sequences that are exactly complementary to the miRNA induce the RNA-mediated interference (RNAi) pathway. Messenger RNA targets are cleaved by ribonucleases in the RISC complex. This mechanism of miRNA-mediated gene silencing has been observed mainly in plants (Hamilton, A. J. and D. C. Baulcombe, Science (1999) 286(5441):950-2 and Reinhart, B. J., et al., MicroRNAs in plants. Genes and Dev. (2002) 16:1616-1626), but an example is known from animals (Yekta, S., I. H. Shih, and D. P. Bartel, Science (2004) 304(5670):594-6). In the second mechanism, miRNAs that bind to imperfect complementary sites on messenger RNA transcripts direct gene regulation at the posttranscriptional level but do not cleave their mRNA targets. MiRNAs identified in both plants and animals use this mechanism to exert translational control of their gene targets (Barter, D. P., Cell (2004) 116(2):281-97).

Hundreds of miRNAs have been identified in the fly, worm, plant and mammalian genomes. The biological role for the majority of the miRNAs remains unknown because almost all of these were found through cloning and bioinformatic approaches (Lagos-Quintana, M., et al., Curr Biol (2002) 12(9):735-9, Lagos-Quintana, M., et al., RNA (2003) 9(2): 175-179, Lagos-Quintana, M., et al., Science (2001) 294(5543): 853-8; Lee, R. C. and V. Ambros, Science (2001) 294(5543):862-4; Lau, N.C., et al., Science (2001) 294 (5543):858-62; Lim, L. P., et al., Genes Dev (2003) 17(8): 991 1008; Johnston, R. J. and O. Robert, Nature (2003) 426(6968):845-9; and Chang, S., et al. Nature (2004) 430 (7001):785-9).

let-7 is an endogenous miRNA which functions as a gene silencing molecule to regulate, at the posttranscriptional level, the expression of some known protein-coding genes that comprise a let-7 target sequence. let-7 miRNA and homologues and variants thereof include conservative substitutions, additions, and deletions therein not adversely affecting the structure or gene silencing function. Preferably, let-7 refers to the nucleic acid encoding let-7 from *C. elegans* (NCBI Accession No. AY390762), most preferably, let-7 refers to the nucleic acid encoding a let-7 family member from humans, including but not limited to NCBI Accession Nos. AJ421724, AJ421725, AJ421726, AJ421727, AJ421728, AJ421729, AJ421730, AJ421731, AJ421732, and biologically active sequence variants of let-7, including alleles, and in vitro generated derivatives of let-7 that demonstrate let-7 activity in that it is capable of binding to and inhibiting the expression of a gene comprising the let-7 target sequence, where the target sequence is 5'-AACTATACAACCTACTACCTCA-3' (SEQ ID NO: 9). Let-7 also encompasses all isoforms of let-7, for example but not limited to let-7 family members including let-7a (SEQ ID NO:1); let-7b (SEQ ID NO:2); hsa-let-7c (SEQ ID NO:3); hsa-let-7d (SEQ ID NO:4); hsa-let-7e (SEQ ID NO:5); hsa-let-7f (SEQ ID NO:6).

In one embodiment, the let-7 miRNAs useful according to the present invention are members of the let-7 family, and can be selected from the group consisting of: hsa-let-7a MIMAT0000062: 5'-UGAGGUAGUAGGUUGUA-UAGUU-3' (SEQ ID NO: 1); hsa-let-7b MIMAT0000063: 5'-UGAGGUAGUAGGUUGUGUGGUU-3' (SEQ ID NO:2); hsa-let-7c MIMAT0000064: 5'-UGAGGUAGUAG-GUUGUAUGGUU-3' SEQ ID NO:3); hsa-let-7d MIMAT0000065: 5'-AGAGGUAGUAGGUUGCAUAGU-3' (SEQ ID NO:4); hsa-let-7e MIMAT0000066: 5'-UGAG-GUAGGAGGUUGUAUAGU-3' (SEQ ID NO:5); hsa-let-7f MIMAT0000067: 5'-UGAGGUAGUAGAUUG-UAUAGUU-3 (SEQ ID NO:6). In some embodiments, the let-7 miRNA is let-7a isoform, of hsa-let-7a MIMAT0000062: 5'-UGAGGUAGUAGGUUGUAUAGUU-3' (SEQ ID NO:1).

In some embodiments, the let-7 miRNA or let-7 miRNA is a pre-miRNA. In some embodiments, the let-7 miRNA is 5'-UGGGAUGAGGUAGUAGGUUGUAUAGUUUU-AGGGUCACACCCACCACUGGGAGA UAACUAUA-CAAUCUACUGUCUUUCCUA-3' (SEQ ID NO:7), also called MI0000060 herein.

In some embodiments, let-7 is *homo sapiens* let-7a1 stem loop (SEQ ID NO:8) as shown in FIG. 7C, which corresponds to 5'-ugggaugagguaguagguuguauaguuuuagggucacac ccaccacugggagauaacuauacaaucuacugucuu: uccua-3' where the underlined residues represent non hybridized nucleic acids, bold resides represent part of the hair-pin turn and the bold underlined residues represent the middle residues of hairpin turn (see FIG. 7C herein).

Let-7 useful in the present invention includes sequence variants of let-7 that retain at least 50% of the target gene-inhibitory function of wildtype mature let-7 miRNA (SEQ ID NO: 1). Let-7 variants generally fall into one or more of three classes: substitution, insertional or deletional variants. Insertions include 5' and/or 3' terminal fusions as well as intrasequence insertions of single or multiple residues. Insertions can also be introduced within the mature sequence of let-7. Intrasequence insertions ordinarily will be smaller insertions than those at the 5' or 3' terminus, on the order of 1 to 4 residues. It is understood that the variants substitutions insertions or deletions of residues will not result in a deleterious effect on the function of the variant in its ability to bind to, and inhibit the expression of genes comprising let-7 target sequence 5'-AACTATACAACC-TACTACCTCA-3' (SEQ ID NO: 9), and preferably the substitution, insertional or deletional variants with have increased binding affinity for the let-7 target sequence 5'-AACTATACAACCTACTACCTCA-3' (SEQ ID NO: 9), and thus increased gene silencing efficacy of the target gene as compared to wild type let-7 corresponding to SEQ ID NO:1.

Substitutional variants are those in which at least one residue has been removed and a different residue inserted in its place. Insertional sequence variants of let-7 are those in which one or more residues are introduced into a predetermined site in the target let-7 miRNA. Most commonly, insertional variants are fusions of nucleic acids at the 5' or 3' terminus of let-7. Deletion variants are characterized by the removal of one or more residues from the let-7 RNA sequence. These variants ordinarily are prepared by site specific mutagenesis of nucleotides in the DNA encoding let-7, thereby producing DNA encoding the variant, and thereafter expressing the DNA in recombinant cell culture. However, variant let-7 fragments can be conveniently prepared by in vitro synthesis. The variants typically exhibit the same qualitative biological activity as the naturally-occurring analogue, although variants also are selected in order to modify the characteristics of let-7.

While the site for introducing a sequence variation is selected, the mutation per se need not be predetermined. For example, in order to optimize the performance of a mutation at a given site, random mutagenesis can be conducted at the target region and the expressed let-7 variants screened for the optimal combination of desired activity. Techniques for making substitution mutations at predetermined sites in DNA having a known sequence are well known. Nucleotide substitutions are typically of single residues; insertions usually will be on the order of about from 1 to 10 residues; and deletions will range about from 1 to 30 residues. Deletions or insertions preferably are made in adjacent pairs; i.e. a deletion of 2 residues or insertion of 2 residues.

Substitutions, deletion, insertions or any combination thereof can be combined to arrive at a final construct. Changes can be made to increase the activity of the miRNA, to increase its biological stability or half-life, and the like. All such modifications to the nucleotide sequences encoding such miRNA are encompassed.

In some embodiments of the present invention, the let-7 miRNA and mimetics thereof are produced by methods known by persons of ordinary skill in the art. In some embodiments, the let-7 miRNA and mimetics thereof can be produced as disclosed in International Patent No: WO2005/047505, which is incorporated herein in its entirety by reference. In some embodiments, the let-7 microRNA molecule is a precursor microRNA molecule. A let-7 precursor microRNA (let-7 pre-miRNA) molecule is an isolated nucleic acid including a stem-loop structure wherein a microRNA sequence is incorporated into the stem-loop structure. In some embodiments, the let-7 precursor microRNA molecule includes a microRNA flanking sequence on either or both sides of the microRNA sequence.

In another embodiment, the let-7 microRNA sequence and the microRNA flanking sequence are derived from the same microRNA gene. In another embodiment of the invention the let-7 microRNA sequence and the microRNA flanking sequence are not derived from the same microRNA gene.

In another embodiment, a let-7 precursor microRNA has a nucleic acid having a stem-loop structure, wherein a let-7 microRNA sequence is incorporated into a stem of the stem-loop structure, and, a microRNA flanking sequence flanking at least one end of the stem-loop structure, wherein the microRNA sequence and the microRNA flanking sequence are not derived from the same microRNA gene.

In some embodiments, the size range of the let-7 miRNA can be from 21 nucleotides to 170 nucleotides, although let-7 miRNAs of up to 2000 nucleotides can be utilized. In some embodiments the size range of the miRNA is from 70 to 170 nucleotides in length. In another embodiment, mature let-7 miRNAs of from 21 to 25 nucleotides in length can be used.

In some embodiments, the let-7 microRNA sequence is an artificial let-7 microRNA. In alternative embodiments, let-7 is from a DNA isolate. A DNA isolate is understood to mean chemically synthesized DNA, cDNA or genomic DNA with or without the 3' and/or 5' flanking regions.

In alternative embodiments, DNA encoding let-7 can be obtained from other sources by a) obtaining a cDNA library from cells containing mRNA, b) conducting hybridization analysis with labeled DNA encoding let-7 or fragments thereof (usually, greater than 100 bp) in order to detect clones in the cDNA library containing homologous sequences, and c) analyzing the clones by restriction enzyme analysis and nucleic acid sequencing to identify full-length clones.

As used herein nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity is routinely used to establish homology. Higher levels of sequence similarity, e.g., 30%, 40%, 50%, 60%, 70%, 80%, 90%, 95% or 99% or more can also be used to establish homology. Methods for determining sequence similarity percentages (e.g., BLASTN using default parameters) are generally available. Software for performing BLAST analyses is publicly available through the National Center for Biotechnology Information (www.ncbi.nlm.nih.gov).

Suitable nucleic acids for use in the methods described herein include, but are not limited to, let-7 pri-miRNA, let-7 pre-miRNA, mature let-7 miRNA or fragments of variants thereof that retain the biological activity of let-7 miRNA and DNA encoding let-7 pri-miRNA, let-7 pre-miRNA, mature let-7 miRNA, fragments or variants thereof, or DNA encoding regulatory elements of let-7 miRNA.

Interestingly, multiple miRNAs can regulate the same mRNA target by recognizing the same or multiple sites. The presence of multiple miRNA complementarily sites in most genetically identified targets can indicate that the cooperative action of multiple RISCs provides the most efficient translational inhibition. Thus, in one embodiment, the methods provide for treatment of cancer by targeting cancer stem cells, the method comprising targeting the cancer stem cells with a pharmaceutical composition comprising let-7 mimetics, where the let-7 mimetic is a different miRNA that complements the function of wild type let-7 miRNA (i.e. SEQ ID NO:1) and/or functions independently of let-7 to gene silence the same mRNA that let-7 silences.

Let-7 Mimetics

In alternative embodiments, mimetics of miRNAs that are reduced and/or lacking in cancer stem cells are useful in the methods of the present invention. A miRNA mimetic is any entity or agent that has at least a gene-silencing function of the subject miRNA. In some embodiments, let-7 mimetics are useful in the methods of the present invention. Examples of let-7 mimetics include, but are not limited to small molecules, proteins, nucleic acids, ribosomes, aptamers, antibodies, nucleic acid analogues, etc. that have let-7 activity or function as the term is used herein. Nucleic acid let-7 mimetics can also include, but are not limited to, RNA interference-inducing molecules, including, but not limited to siRNA, dsRNA, stRNA, shRNA and modified versions thereof, where the RNA interference molecule has the same function as let-7 miRNA.

In some embodiments the let-7 mimetics can be RNA-interference or RNA interference molecules, including, but not limited to double-stranded RNA, such as siRNA, double-stranded DNA or single-stranded DNA. In some embodiments, a let-7 mimetic is a single-stranded RNA (ssRNA), a form of RNA endogenously found in eukaryotic cells as the product of DNA transcription. Cellular ssRNA molecules include messenger RNAs (and the progenitor pre-messenger RNAs), small nuclear RNAs, small nucleolar RNAs, transfer RNAs and ribosomal RNAs. Double-stranded RNA (dsRNA) induces a size-dependent immune response such that dsRNA larger than 30 bp activates the interferon response, while shorter dsRNAs feed into the cell's endogenous RNA interference machinery downstream of the Dicer enzyme.

Numerous specific siRNA molecules have been designed that have been shown to inhibit gene expression (Ratcliff et al. Science 276:1558-1560, 1997; Waterhouse et al. Nature 411:834-842, 2001). In addition, specific siRNA molecules have been shown to inhibit, for example, HIV-1 entry to a cell by targeting the host CD4 protein expression in target cells thereby reducing the entry sites for HIV-1 which targets cells expressing CD4 (Novina et al. Nature Medicine, 8:681-686, 2002). Short interfering RNA have further been designed and successfully used to silence expression of Fas to reduce Fas-mediated apoptosis in vivo (Song et al. Nature Medicine 9:347-351, 2003).

It has been shown in plants that longer, about 24-26 nt siRNA, correlates with systemic silencing and methylation of homologous DNA. Conversely, the about 21-22 nt short siRNA class correlates with mRNA degradation but not with systemic signaling or methylation (Hamilton et al. EMBO J. 2002 Sep 2; 21(17):4671-9). These findings reveal an unexpected level of complexity in the RNA silencing pathway in plants that may also apply in animals. In higher order eukaryotes, DNA is methylated at cytosines located 5' to guanosine in the CpG dinucleotide. This modification has important regulatory effects on gene expression, especially when involving CpG-rich areas known as CpG islands, located in the promoter regions of many genes. While almost all gene-associated islands are protected from methylation on autosomal chromosomes, extensive methylation of CpG islands has been associated with transcriptional inactivation of selected imprinted genes and genes on the inactive X-chromosomes of females. Aberrant methylation of normally unmethylated CpG islands has been documented as a relatively frequent event in immortalized and transformed cells and has been associated with transcriptional inactivation of defined tumor suppressor genes in human cancers. In this last situation, promoter region hypermethylation stands as an alternative to coding region mutations in eliminating tumor suppression gene function (Herman, et al.). The use of siRNA molecules for directing methylation of a target gene is described in U.S. Provisional Application No. 60/447,013, filed Feb. 13, 2003, referred to in U.S. Patent Application Publication No. 20040091918.

It is also known that the RNA interference does not have to match perfectly to its target sequence. Preferably, however, the 5' and middle part of the antisense (guide) strand of the siRNA is perfectly complementary to the target nucleic acid sequence.

The RNA interference-inducing molecule functioning as let-7 mimetics according to the present invention includes RNA molecules that have natural or modified nucleotides, natural ribose sugars or modified sugars and natural or modified phosphate backbone.

Accordingly, the RNA interference-inducing molecules functioning as a let-7 mimetic include, but are not limited to, unmodified and modified double stranded (ds) RNA molecules including short-temporal RNA (stRNA), small interfering RNA (siRNA), short-hairpin RNA (shRNA), microRNA (miRNA), and double-stranded RNA (dsRNA), (see, e.g. Baulcombe, Science 297:2002-2003, 2002). The dsRNA molecules, e.g. siRNA, also may contain 3' overhangs, preferably 3'UU or 3'TT overhangs. In one embodiment, the siRNA molecules do not include RNA molecules that comprise ssRNA greater than about 30-40 bases, about 40-50 bases, about 50 bases or more. In one embodiment, the siRNA molecules have a double stranded structure. In one embodiment, the siRNA molecules are double stranded for more than about 25%, more than about 50%, more than about 60%, more than about 70%, more than about 80% or more than about 90% of their length.

In some embodiments, let-7 is any agent which binds to and inhibits the expression of an RNA transcript comprising a let-7 target sequence, where the target sequence is 5'-AAC-TATACAACCTACTACCTCA-3' (SEQ ID NO: 9) as shown in FIG. 7D. In such embodiments, these agents can be an RNA interference-inducing molecule, including, but not limited to unmodified and modified double stranded (ds) RNA molecules including, short-temporal RNA (stRNA), small interfering RNA (siRNA), short-hairpin RNA (shRNA), microRNA (miRNA), and double-stranded RNA (dsRNA). In other embodiments, the agents may be any small molecule, protein, aptamer, nucleic acid analogue, antibody etc. that binds to and inhibits the expression of an RNA transcript comprising a let-7 target sequence SEQ ID NO:9.

The miRNA and RNA interference molecules according to the present invention can be produced using any known techniques such as direct chemical synthesis, through processing of longer double stranded RNAs by exposure to recombinant Dicer protein or *Drosophila* embryo lysates, through an in vitro system derived from S2 cells, using phage RNA polymerase, RNA-dependant RNA polymerase, and DNA based vectors. Use of cell lysates or in vitro processing may further involve the subsequent isolation of the short, for example, about 21-23 nucleotide, siRNAs from the lysate, etc. Chemical synthesis usually proceeds by making two single stranded RNA-oligomers followed by the annealing of the two single stranded oligomers into a double stranded RNA. Other examples include methods disclosed in WO 99/32619 and WO 01/68836 that teach chemical and enzymatic synthesis of siRNA. Moreover, numerous commercial services are available for designing and manufacturing specific siRNAs (see, e.g., QIAGEN Inc., Valencia, Calif. and AMBION Inc., Austin, Tex.).

Examples of methods of preparing such RNA interference are shown, for example in an International Patent application Nos. PCT/US03/34424 and PCT/US03/34686 the contents and references of which are herein incorporated by reference in their entirety.

Various specific siRNA and miRNA molecules have been described and additional molecules can be easily designed by one skilled in the art. For example, the miRNA Database at http://www.sanger.ac.uk/Software/Rfam/mirna/index.shtml provides a useful source to identify additional miRNAs useful according to the present invention (Griffiths-Jones S. NAR, 2004, 32, Database Issue, D109-D111; Ambros V, Bartel B, Bartel D P, Burge C B, Carrington J C, Chen X, Dreyfuss G, Eddy S R, Griffiths-Jones S, Marshall M, Matzke M, Ruvkun G, Tuschl T. RNA, 2003, 9(3), 277-279).

The miRNA and RNA interference as described herein also includes RNA molecules having one or more non-natural nucleotides, i.e. nucleotides other than adenine "A", guanine "G", uracil "U", or cytosine "C", a modified nucleotide residue or a derivative or analog of a natural nucleotide are also useful. Any modified residue, derivative or analog may be used to the extent that it does not eliminate or substantially reduce (by at least 50%) RNAi activity of the dsRNA. For example, the activity a miRNA or RNAi molecule with the modified residue can be compared with the activity of a miRNA or RNAi molecule with the same nucleic acid sequence without the modified residue in an assay for gene silencing the target gene. If the miRNA or RNAi with the modified residue(s) has an efficiency of gene silencing which is the same, greater or a least half as efficient as the miRNA or RNAi without the modification, the modified mRNA or RNAi is useful in the methods and compositions as disclosed herein. Examples of modified residues, derivatives or analogues include, but are not limited to, aminoallyl UTP, pseudo-UTP, 5-I-UTP, 5-I-CTP, 5-Br-UTP, alpha-S ATP, alpha-S CTP, alpha-S GTP, alpha-S UTP, 4-thio UTP, 2-thio-CTP, 2'NH2 UTP, 2'NH$_2$ CTP, and 2'F UTP. Such modified nucleotides include, but are not limited to, aminoallyl uridine, pseudo-uridine, 5-I-uridine, 5-I-cytidine, 5-Br-uridine, alpha-S adenosine, alpha-S cytidine, alpha-S guanosine, alpha-S uridine, 4-thio uridine, 2-thio-cytidine, 2'NH2 uridine, 2'NH2 cytidine, and 2' F uridine, including the free pho (NTP) RNA molecules as well as all other useful forms of the nucleotides.

RNA interference as referred to herein additionally includes RNA molecules which contain modifications in the ribose sugars, as well as modifications in the "phosphate backbone" of the nucleotide chain. For example, siRNA or miRNA molecules containing D-arabinofuranosyl structures in place of the naturally-occurring D-ribonucleosides found in RNA can be used in RNA interference according to the present invention (U.S. Pat. No. 5,177,196). Other examples include RNA molecules containing the o-linkage between the sugar and the heterocyclic base of the nucleoside, which confers nuclease resistance and tight complementary strand binding to the oligonucleotides and molecules similar to the oligonucleotides containing 2'-O-methyl ribose, arabinose and particularly D-arabinose (U.S. Pat. No. 5,177,196). Also, phosphorothioate linkages can be used to stabilize the siRNA and miRNA molecules (U.S. Pat. No. 5,177,196). siRNA and miRNA molecules having various "tails" covalently attached to either their 3'- or to their 5'-ends, or to both, are also been known in the art and can be used to stabilize the siRNA and miRNA molecules delivered using the methods of the present invention. Generally speaking, intercalating groups, various kinds of reporter groups and lipophilic groups attached to the 3' or 5' ends of the RNA molecules are well known to one skilled in the art and are useful according to the methods of the present invention. Descriptions of syntheses of 3'-cholesterol or 3'-acridine modified oligonucleotides applicable to preparation of modified RNA molecules useful according to the present invention can be found, for example, in the articles: Gamper, H. B., Reed, M. W., Cox, T., Virosco, J. S., Adams, A. D., Gall, A., Scholler, J. K., and Meyer, R. B. (1993) Facile Preparation and Exonuclease Stability of 3'-Modified Oligodeoxynucleotides. Nucleic Acids Res. 21 145-150; and Reed, M. W., Adams, A. D., Nelson, J. S., and Meyer, R. B., Jr. (1991) Acridine and Cholesterol-Derivatized Solid Supports for Improved Synthesis of 3'-Modified Oligonucleotides. Bioconjugate Chem. 2 217-225 (1993).

Let-7 miRNAs and Let-7 Mimetics as Therapeutics

The methods of the invention are useful for treating any type of disease or disorder in which it is desirable to increase let-7 miRNA. These include, for example, diseases where let-7 expression is reduced or lacking in the pathological tissue and the reduction contributes to the disease pathology and/or progression of the disease. An example of such a disease is cancer.

In one embodiment methods are provided to treat cancers by using agents which inhibit the gene or gene product that is regulated by let-7 miRNA. For example, also encompassed in the present invention is use of any agent that inhibits the expression of a gene or inhibits its gene product (protein) that comprises a let-7 target sequence in its mRNA. The let-7 target site may be in the 5' UTR, the 3' UTR or in the coding region of the mRNA. The target sequence of let-7 is SEQ ID NO:9 or homologues thereof. Examples of genes that comprise let-7 target sequences include, but are not limited to, RAS, HRAS, lin-42, KRAS, GRB2, hbl-1, daf-12, pha-4, or human homologues thereof, as disclosed in International Patent Application: WO06/028967, which is incorporated in its entirety herein by reference. In some embodiments, these genes encode endogenous mammalian proteins, C. elegans proteins, parasitic proteins, and viral proteins encoded by a eukaryotic cell after entry of a virus into the cell.

In some embodiments, the subject can be administered a plurality of agents to inhibit more than one gene and/or protein which are normally regulated at the level of mRNA by let-7 miRNA. The agents can be RNA interference molecules, for example miRNA, siRNA, shRNA, or proteins, small molecules, nucleic acids, nucleic acid analogues, aptamers, antibodies, peptides and variants and analogues thereof. In some embodiments, where the agent is an antibody, the antibody can be a recombinant antibody, humanized antibody, chimeric antibody, modified antibody, monoclonal antibody, polyclonal antibody, miniantibody, dimeric miniantibody, minibody, diabody or tribody or antigen-binding variants, analogues or modified versions thereof.

In some embodiments, the disease is associated with a stem cell. In some embodiments, the disease is associated with a cancer stem cell.

In one embodiment, the cancer is breast cancer. Thus in one embodiment, let-7 miRNA and let-7 mimetics of the present invention are useful in therapeutic protocols in the treatment of breast cancer. In some embodiments, the methods of the present invention are useful for treating cancers where cancer cells lack let-7 or have reduced let-7 expression, including, as non-limiting examples, colon and lung cancer. Thus in one embodiment, let-7 miRNA and let-7 mimetics of the present invention are useful in therapeutic protocols in the treatment of, e.g., colon and lung cancer.

The let-7 miRNA relationship to cancer is not limited to breast, lung, or colon cancer—rather, let-7 miRNA represents a broad-spectrum tumor suppressor. Thus, in other embodiments, the let-7 miRNA and let-7 mimetics of the present invention are useful in therapeutic protocols related to other cancers, including, but not limited to, cancer selected breast cancer, lung cancer, head and neck cancer, bladder cancer, stomach cancer, cancer of the nervous system, bone cancer, bone marrow cancer, brain cancer, colon cancer, esophageal cancer, endometrial cancer, gastrointestinal cancer, genital-urinary cancer, stomach cancer, lymphomas, melanoma, glioma, bladder cancer, pancreatic cancer, gum cancer, kidney cancer, retinal cancer, liver cancer, nasopharynx cancer, ovarian cancer, oral cancers, bladder cancer, hematological neoplasms, follicular lymphoma, cervical cancer, multiple myeloma, osteosarcomas, thyroid cancer, prostate cancer, colon cancer, prostate cancer, skin cancer, stomach cancer, testis cancer, tongue cancer, or uterine cancer.

Also encompassed is the use of other miRNAs and mimetics thereof that are downregulated in cancer stem cells for the treatment of other cancers, wherein the cancer comprises a cancer stem cell lacking or having reduced expression of the miRNA. Examples of such miRNAs include, but are not limited to miR-107, miR-10a, miR-128a, miR128b, miR-132, miR-138, miR-16, miR-17, miR-195, miR-199a, miR-20, miR-200a, miR-200b, miR-200c, miR-20b, and miR-22.

Production of Let-7 miRNA and Mimetics Thereof

MiRNA can be isolated from cells or tissues, recombinantly produced, or synthesized in vitro by a variety of techniques well known to one of ordinary skill in the art. In one approach, miRNA is isolated from cells or tissues.

Techniques for isolating miRNA from cells or tissues are well known to one of ordinary skill in the art. For example, miRNA can be isolated from total RNA using the miRNA isolation kit from Ambion, Inc. Another technique utilizes the flashPAGE Fractionator System (Ambion, Inc.) for PAGE purification of small nucleic acids.

The miRNA can be obtained by preparing a recombinant version thereof (i.e., by using the techniques of genetic engineering to produce a recombinant nucleic acid which can then be isolated or purified by techniques well known to one of ordinary skill in the art). This approach involves growing a culture of host cells in a suitable culture medium, and purifying the miRNA from the cells or the culture in which the cells are grown. For example, the methods include a process for producing a miRNA in which a host cell, containing a suitable expression vector that includes a nucleic acid encoding an miRNA, is cultured under conditions that allow expression of the encoded miRNA. In a preferred embodiment the nucleic acid encodes let-7. The miRNA can be recovered from the culture, from the culture medium or from a lysate prepared from the host cells, and further purified. The host cell can be a higher eukaryotic host cell such as a mammalian cell, a lower eukaryotic host cell such as a yeast cell, or the host cell can be a prokaryotic cell such as a bacterial cell. Introduction of a vector containing the nucleic acid encoding the miRNA into the host cell can be effected by calcium phosphate transfection, DEAE-dextran mediated transfection, or electroporation (Davis, L. et al., Basic Methods in Molecular Biology (1986)).

Any host/vector system can be used to express one or more of the miRNAs. These include, but are not limited to, eukaryotic hosts such as HeLa cells and yeast, as well as prokaryotic host such as E. coli and B. subtilis. miRNA can be expressed in mammalian cells, yeast, bacteria, or other cells where the miRNA gene is under the control of an appropriate promoter. Appropriate cloning and expression vectors for use with prokaryotic and eukaryotic hosts are described by Sambrook, et al., in Molecular Cloning: A Laboratory Manual, Second Edition, Cold Spring Harbor, N.Y. (1989). In the preferred embodiment, the miRNA is expressed in mammalian cells. Examples of mammalian expression systems include C127, monkey COS cells, Chinese Hamster Ovary (CHO) cells, human kidney 293 cells, human epidermal A43 1 cells, human Colo205 cells, 3T3 cells, CV-1 cells, other transformed primate cell lines, normal diploid cells, cell strains derived from in vitro culture of primary tissue, primary explants, HeLa cells, mouse L cells, BILK, HL-60, U937, HaK or Jurkat cells.

Mammalian expression vectors will comprise an origin of replication, a suitable promoter, polyadenylation site, transcriptional termination sequences, and 5' flanking non-transcribed sequences. DNA sequences derived from the SV40 viral genome, for example, SV40 origin, early promoter, enhancer, splice, and polyadenylation sites may be used to provide the required non-transcribed genetic elements. Potentially suitable yeast strains include *Saccharomyces cerevsiae, Schizosaccharomyces pombe, Klayveromyces strains, Candida*, or any yeast strain capable of expressing miRNA. Potentially suitable bacterial strains include *Escherichia coli, Bacillus subtilis, Salmonella typhimurium*, or any bacterial strain capable of expressing miRNA.

In another approach, genomic DNA encoding let-7 is isolated, the genomic DNA is expressed in a mammalian expression system, and RNA is purified and modified as necessary for administration to a patient. In one approach, the let-7 is in the form of a pre-miRNA, which can be modified as desired (i.e. for increased stability or cellular uptake).

Knowledge of DNA sequences of miRNA allows for modification of cells to permit or increase expression of an endogenous miRNA. Cells can be modified (e.g., by homologous recombination) to provide increased miRNA expression by replacing, in whole or in part, the naturally occurring promoter with all or part of a heterologous promoter so that the cells express the miRNA at higher levels. The heterologous promoter is inserted in such a manner that it is operatively linked to the desired miRNA encoding sequences. See, for example, PCT International Publication No. WO 94/12650 by Transkaryotic Therapies, Inc., PCT International Publication No. WO 92/20808 by Cell Genesys, Inc., and PCT International Publication No. WO 91/09955 by Applied Research Systems. Cells also may be; engineered to express an endogenous gene comprising the miRNA under the control of inducible regulatory elements, in which case the regulatory sequences of the endogenous gene may be replaced by homologous recombination. Gene activation techniques are described in U.S. Pat. No. 5,272,071 to Chappel; U.S. Pat. No. 5,578,461 to Sherwin et al.; PCT/US92/09627 (WO93/09222) by Selden et al.; and PCT/US90/06436 (WO91/06667) by Skoultchi et al. The miRNA may be prepared by culturing transformed host cells under culture conditions suitable to express the miRNA. The resulting expressed miRNA may then be purified from such culture (i.e., from culture medium or cell extracts) using known purification processes, such as gel filtration and ion exchange chromatography. The purification of the miRNA may also include an affinity column containing agents which will bind to the protein; one or more column steps over such affinity resins as concanavalin A-agarose, Heparin-toyopearl™ or Cibacrom blue 3GA Sepharose™; one or more steps involving hydrophobic interaction chromatography using such resins as phenyl ether, butyl ether, or propyl ether; immunoaffnity chromatography, or complementary cDNA affinity chromatography.

The miRNA can also be expressed as a product of transgenic animals, which are characterized by somatic or germ cells containing a nucleotide sequence encoding the miRNA. A vector containing DNA encoding miRNA and appropriate regulatory elements can be inserted in the germ line of animals using homologous recombination (Capecchi, Science t 244:1288-1292 (1989)), such that they express the miRNA. Transgenic animals, preferably non-human mammals, are produced using methods as described in U.S. Pat. No. 5,489,743 to Robinson, et al., and PCT Publication No. WO 94/28122 by Ontario Cancer Institute. miRNA can be isolated from cells or tissue isolated from transgenic animals as discussed above.

In one approach, the miRNA can be obtained synthetically, for example, by chemically synthesizing a nucleic acid by any method of synthesis known to the skilled artisan. The synthesized miRNA can then be purified by any method known in the art. Methods for chemical synthesis of nucleic acids include, but are not limited to, in vitro chemical synthesis using phosphotriester, phosphate or phosphoramidite chemistry and solid phase techniques, or via deoxynucleoside H-phosphonate intermediates (see U.S. Pat. No. 5,705,629 to Bhongle).

In some circumstances, for example, where increased nuclease stability is desired, nucleic acids having nucleic acid analogs and/or modified internucleoside linkages may be preferred. Nucleic acids containing modified internucleoside linkages can also be synthesized using reagents and methods that are well known in the art. For example, methods of synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide ($-CH_2-S-CH_2$), diinethylene-sulfoxide ($-CH_2-SO-CH_2$), dimethylene-sulfone ($-CH_2-SO_2-CH_2$), 2'-O-alkyl, and 2'-deoxy-2'-fluoro' phosphorothioate internucleoside linkages are well known in the art (see Uhlmann et al., 1990, Chem. Rev. 90:543-584; Schneider et al., 1990, Tetrahedron Lett. 31:335 and references cited therein). U.S. Pat. Nos. 5,614,617 and 5,223,618 to Cook, et al., U.S. Pat. No. 5,714,606 to Acevedo, et al, U.S. Pat. No. 5,378,825 to Cook, et al., U.S. Pat. Nos. 5,672,697 and 5,466,786 to Buhr, et al., U.S. Pat. No. 5,777,092 to Cook, et al., U.S. Pat. No. 5,602,240 to De Mesmacker, et al., U.S. Pat. No. 5,610,289 to Cook, et al. and U.S. Pat. No. 5,858,988 to Wang, also describe nucleic acid analogs for enhanced nuclease stability and cellular uptake.

Pharmaceutical Compositions

In some embodiments, miRNAs and miRNA mimetics, for example let-7 miRNAs and/or let-7 mimetics are administered to a subject in a pharmaceutical composition where the subject has a cancer stem cell. The administration may be a treatment and/or prophylaxis for cancer, where the subject has at least one cancer stem cell. The subject may have, or may not have, symptoms or manifestation of cancer, since cancer stem cells can exist in the absence of symptoms of cancer. In some embodiments, the pharmaceutical compositions comprising miRNA and miRNA mimetics, for example let-7 miRNA and/or let-7 mimetics are administered to a subject with a cancer stem cell. In some embodiments, the cancer stem cell is present in any type of cancer. In some embodiments, the cancer is breast cancer. In some embodiments, the cancer is a treatment-resistant cancer, for example but not limited to a chemotherapy-resistant breast cancer.

In another aspect of the present invention, the methods described herein encompass administering a pharmaceutical composition comprising a miRNA or mimetic thereof to a subject, where the subject comprises a cancer stem cell which is lacking or has reduced expression of an miRNA. In this aspect, the cancer stem cell is, e.g., a cancer stem cell lacking or having reduced expression of one or more of the following miRNAs; let-7, miR-107, miR-10a, miR-128a, miR128b, miR-132, miR-138, miR-16, miR-17, miR-195, miR-199a, miR-20, miR-200a, miR-200b, miR-200c, miR-20b, miR-22.

Therefore in some embodiments, the methods of the present invention relate to the treatment of cancers by targeting cancer stem cells, the method comprising upregulating let-7 microRNAs or providing analogous pharmaceutical compounds, for example pharmaceutical compositions comprising let-7 miRNA and/or let-7 mimetics to a cancer stem cell in a therapeutic effective amount for the treatment of cancer. In such embodiments, the cancer comprises a cancer stem cell and/or a cell with reduced or lacking let-7 expression.

In some embodiments, the let-7 miRNAs are nucleic acids, for example but not limited to let-7 pri miRNA, let-7 pre-miRNA, mature let-7 miRNA or fragments or variants thereof that retain the same biological activity as the mature let-7 miRNA, for example, they have a minimum biological activity of binding to (or hybridizing to) a target RNA transcript comprising a let-7 target sequence, and inhibiting expression from that transcript where the target sequence is 5'-AACTATACAACCTACTACCTCA-3' (SEQ ID NO: 9). In some embodiments, the let-7 miRNA are encoded by DNA compositions encoding a let-7 pri miRNA, let-7 pre-miRNA, mature let-7 miRNA or fragments or homologues thereof, or regulatory elements which express the let-7 miRNA.

In alternative embodiments, mimetics of let-7 miRNA are useful in the methods of the present invention. A let-7 mimetic is any entity or agent that functions as a let-7 miRNA. Examples of let-7 mimetics are, but not limited to small molecules, proteins, nucleic acids, ribosomes, aptamers, antibodies, nucleic acid analogues etc. Nucleic acids let-7 mimetics can also be, for example, but not limited to, RNA interference-inducing molecules, for example but not limited to siRNA, dsRNA, stRNA, shRNA and modified versions thereof, where the RNA interference molecule has the same function as let-7 miRNA.

In another aspect of the present invention provide methods to treat cancers by targeting the cancer stem cells, the method comprising targeting the cancer stem cell with agents that inhibit genes and/or their gene products (mRNAs or proteins) which are normally gene silenced by let-7 miRNA. Such genes are, for example, genes which comprise a let-7 target sequence within their mRNA. The let-7 target sequence can be in the 5'UTR, 3'UTR or coding sequence. Examples of such genes that comprise a let-7 target sequence, (i.e. genes which have SEQ ID NO:9 or a homologue thereof) within their mRNA are for example, but not limited to, RAS, HRAS, KRAS, lin-42, GRB2, hbl-1, daf-12 and pha-4. In some embodiments, agents inhibit the activity and/or the expression of genes comprising let-7 target sequence within their mRNA. In some embodiments, the methods of the present intervention relate to the treatment of cancers by targeting cancer stem cells, the method comprising administering a pharmaceutical composition comprising at least one agent that inhibits the activity and/or the expression of at least one gene that is gene silenced by let-7 and/or comprises a let-7 target within their mRNA to a cancer stem cell in therapeutic effective amount for the treatment of cancer. In such embodiments, the cancer comprises a cancer stem cell and/or a cell with reduced or lacking let-7 expression.

Effective, safe dosages can be experimentally determined in model organisms and in human trials by methods well known to one of ordinary skill in the art. The let-7 miRNA and let-7 mimetics in a pharmaceutical composition can be administered alone or in combination with adjuvant cancer therapy such as surgery, chemotherapy, radiotherapy, thermotherapy, immunotherapy, hormone therapy and laser therapy, to provide a beneficial effect, e.g. reduce tumor size, reduce cell proliferation of the tumor, inhibit angiogenesis, inhibit metastasis, or otherwise improve at least one symptom or manifestation of the disease.

In some embodiments, the pharmaceutical compositions comprising let-7 miRNA and/or let-7 are administered to cells in vivo and in vitro. The in vivo administration as used herein means delivery of the let-7 miRNA and let-7 mimetics into a living subject, including human. The in vitro administration as used herein means delivery of let-7 miRNA and let-7 mimetics into cells and organs outside a living subject.

Targeting Let-7 miRNA and Let-7 Mimetics

In another embodiment of the invention miRNA and/or miRNA mimetics, for example let-7 miRNA and/or let-7 mimetics are targeted to specific cells, for example cancer stem cells in order minimize or avoid any undesired potential side effects of let miRNA and/or let-7 mimetic. In such embodiments, the methods of the present invention provide means to target cancer stem cells specifically, because these cancer stem cells typically express a variety of specific proteins on their surface and thus can be targeted. In some embodiments, the miRNA and/or let-7 mimetics can be fused to a cell targeting moiety or protein, as disclosed in the International Patent Application PCT/US05/029111 which is incorporated herein in its entirety by reference.

In such embodiments, the target moiety specifically brings the delivery system to the target cell. The particular target moiety for delivering the interference RNAs, including let-7 miRNAs and let-7 mimetic, can be determined empirically based upon the present disclosure and depending upon the target cell. For example, with somatic cell therapy in vivo with readily accessible cells or tissues such as an intravascular target, immune cell target or the like, the important attributes of the target moiety are affinity and selectivity.

In some embodiments of the present invention, the miRNA and siRNA are delivered to a limited number of cells thereby limiting, for example, potential side effects of therapies using siRNA. The particular cell surface targets that are chosen for the targeting moiety will depend upon the target cell. Cells can be specifically targeted, for example, by use of antibodies against unique proteins, lipids or carbohydrates that are present on the cell surface. A skilled artisan can readily determine such molecules based on the general knowledge in the art.

The strategy for choosing the targeting moiety is very adaptable. For example, any cell-specific antigen, including proteins, carbohydrates and lipids can be used to create an antibody that can be used to target the miRNA and siRNA to a specific cell type according to the methods described herein. For example, certain tumors frequently possess a large amount of a particular cell surface receptor (e.g. neu with breast cancers), or an abnormal form of a particular protein. Therefore, a tumor antigen can serve as a specific target to deliver siRNA into the tumor cells to inhibit growth and/or proliferation of the cell or to destroy the cell. Any known tumor antigen expressed on the tumor cell surface can be used for generating an antibody to serve as a targeting moiety.

For example, tumor antigens useful according to the present invention include, but are not limited to, mini-MUC; MUC-1 (Marshall et al., J. CLin. Oncol. 18:3964-73 (2000); HER2/neu; HER2 receptor (U.S. Pat. No. 5,772,997); mammoglobulin (U.S. Pat. No. 5,922,836); labyrinthin (U.S. Pat. No. 6,166,176); SCP-1 (U.S. Pat. No. 6,140,050); NY-ESO-1 (U.S. Pat. No. 6,140,050); SSX-2 (U.S. Pat. No. 6,140,050); N-terminal blocked soluble cytokeratin (U.S. Pat. No. 4,775,620); 43 kD human cancer antigen (U.S. Pat. No. 6,077,950); human tumor associated antigen (PRAT) (U.S. Pat. No. 6,020,478); human tumor associated antigen (TUAN) (U.S. Pat. No. 5,922,566); L6 antigen (U.S. Pat. No. 5,597,707); carcinoembryonic antigen (RT-PCR analysis for breast cancer prognosis in Clin Cancer Res 6:4176-85, 2000); CA15-3 (Eur J Gynaecol Oncol 21:278-81, 2000); oncoprotein 18/stathmin (Op18) (Br J. Cancer 83:311-8, 2000); human glandular kallikrein (hK2) (Breast Cancer Res Treat 59:263-70, 2000); NY-BR antigens (Cancer Immun. March 30; 1:4, 2001), tumor protein D52 (Cancer Immun. March 30; 1:4, 2001), and prostate-specific antigen (Breast Cancer Res Treat 59:263-70, 2000); and EEA.

In some embodiments, the tumor antigens useful for targeting the let-7 miRNA and mimetics thereof are CD44, CD133, ABC7, c-kit, or SCA1.

In other embodiments, the let-7 miRNA and/or let-7 mimetics of the present invention can be targeted to other receptors of interest, for example but not limited to include those for lymphokines such as interleukins and interferons, for example, the interleukin-2 (IL-2) receptor (IL-2R). The p55, IL-2R alpha chain, also referred to as the Tac protein, is associated with Ag or mitogen-activated T-cells but not resting T-cells. It is expressed in high levels on malignant cells of lymphoid cancers such as adult T-cell leukemia, cutaneous T-cell lymphoma and Hodgkin's disease. The anti-Tac antibody will bind to this protein. Humanized version of such antibodies are known and described in Queen, C., et al., Proc. Natl. Acad. Sci. USA:10029-10039 (1989); Hakimi, J., et al., J. of Immun. 151:1075-1085 (1993) (Mik.beta.1 which is a Mab against IL-2R.beta. chain); Kreitman, R. J., et al., J. of Immun. 149:2810-2815 (1992); Hakimi, J., et al., J. of Immun 147:1352-1359 (1991). Antibodies to these various proteins are known and available. These antibodies can readily be adapted for use in this system by following the general procedures described herein, and substituting the gene coding for the desired binding site for the exemplified gene.

In another embodiment, let-7 miRNA and/or let-7 mimetics of the present invention can be targeted the using single chain antibody fragment, ML39 scFv, that recognizes the ErbB2 receptor (Li et al. "Single-chain antibody-mediated gene delivery into ErbB2-positive human breast cancer cells" Cancer Gene Ther. 2001; 8:555-65; also Song Nature Biotech 2005). ML39 scFV recognizes the ErbB2 receptor and as such is useful as a targeting moiety in the methods of the present invention for targeting and delivery to cells expressing ErbB2, for example, breast cancer cells. Methods for producing a fusion protein containing an ML39 scFv targeting moiety are described below and in Li et al. 2001 (supra). Other useful single chain antibody fragment to target the let-7 miRNA and RNA interference molecules of the present invention are a single chain antibody fragment to the transferrin receptor described in, for example, Xu et al. (Mol Cancer Ther. 2002, 1(5):337-46) and the single chain antibody fragment recognizing prostate specific membrane antigen described in, for example, Li et al. (Intl J Oncology. 2003, 23: 1329-1332). Any antibody with a known sequence can be used to prepare a similar construct as described above, and any method to prepare such a construct is commonly known in the art.

Delivery of Let-7 miRNA or Let-7 Mimetics

In one embodiment, a vector encoding let-7 miRNA and/or a let-7 mimetic is delivered into a specific target cell. Nucleic acid sequences necessary for expression in prokaryotes usually include a promoter, an operator (optional), often along with other sequences. Eukaryotic cells are known to utilize promoters, enhancers, and termination and polyadenylation signals.

One can also use localization sequences to deliver the released let-7 miRNA and/or let-7 mimetics intracellularly to a cell compartment of interest. Typically, the delivery system first binds to a specific receptor on the cell. Thereafter, the targeted cell internalizes the delivery system, which is bound to the cell. For example, membrane proteins on the cell surface, including receptors and antigens can be internalized by receptor mediated endocytosis after interaction with the ligand to the receptor or antibodies. (Dautry-Varsat, A., et al., Sci. Am. 250:52-58 (1984)). This endocytic process is exploited by the present delivery system. Because this process may damage the let-7 miRNA or let-7 RNA interference molecules, for example let-7 siRNA as it is being internalized, it may be desirable to use a segment containing multiple repeats of the RNA interference-inducing molecule of interest. One can also include sequences or moieties that disrupt endosomes and lysosomes. See, e.g., Cristiano, R. J., et al., Proc. Natl. Acad. Sci. USA 90:11548-11552 (1993); Wagner, E., et al., Proc. Natl. Acad. Sci. USA 89:6099-6103 (1992); Cotten, M., et al., Proc. Natl. Acad. Sci. USA 89:6094-6098 (1992).

In some embodiments, let-7 miRNA and/or let-7 mimetics are complexed with desired targeting moieties by mixing the let-7 miRNA or let-7 RNA interference molecules with the targeting moiety in the presence of complexing agents. Examples of such complexing agents include, but are not limited to, poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. In some embodiments, the complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g. p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DE AE-albumin and DEAE-dextran, polymethylacrylate, polyhexylacrylate, poly(D,L-lactic acid), poly(DL-lactic-co-glycolic acid (PLGA), alginate, and polyethyleneglycol (PEG), and polyethylenimine.

In alternative embodiments, let-7 miRNA and/or let-7 mimetic complexing agent is protamine or an RNA-binding domain, such as an siRNA-binding fragment or nucleic acid binding fragment of protamine. Protamine is a polycationic peptide with molecular weight about 4000-4500 Da. Protamine is a small basic nucleic acid binding protein, which serves to condense the animal's genomic DNA for packaging into the restrictive volume of a sperm head (Warrant, R. W., et al., Nature 271:130-135 (1978); Krawetz, S. A., et al., Genomics 5:639-645 (1989)). The positive charges of the protamine can strongly interact with negative charges of the phosphate backbone of nucleic acid, such as RNA, resulting in a neutral and stable interference RNA-protamine complex.

In one embodiment, the protamine fragment is encoded by a nucleic acid sequence disclosed in International Patent Application: PCT/US05/029111, which is incorporated herein in its entirety by reference. The methods, reagents and references that describe a preparation of a nucleic acid-protamine complex in detail are disclosed in the U.S. Patent Application Publication Nos. US2002/0132990 and US2004/0023902, and are herein incorporated by reference in their entirety.

In some embodiments, a binding domain is used to complex the targeting moiety to the let-7 miRNA and/or let-7 mimetic. In some embodiments, the binding domain is selected from the nucleic acid binding domains present in proteins selected from the group consisting of GCN4, Fos, Jun, TFIIS, FMRI, yeast protein HX, Vigillin, Merl, bacterial polynucleotide phosphorylase, ribosomal protein S3, and heat shock protein.

Administration

In one aspect, the invention provides methods of administering any of the let-7 miRNA and/or let-7 mimetics described herein to a subject. When administered, the let-7 miRNA and/or let-7 mimetics are applied in a therapeutically effective, pharmaceutically acceptable amount as a pharmaceutically acceptable formulation.

A therapeutically effective amount can be determined on an individual basis and will be based, at least in part, on consideration of the species of mammal, the mammal's age, sex, size, and health; the compound and/or composition used, the type of delivery system used; the time of administration relative to the severity of the disease; and whether a single, multiple, or controlled-release dose regimen is employed. A therapeutically effective amount can be determined by one of ordinary skill in the art employing such factors and using no more than routine experimentation.

In administering the systems and methods of the invention to a subject, dosing amounts, dosing schedules, routes of administration, and the like may be selected so as to affect known activities of these systems and methods. Dosage may be adjusted appropriately to achieve desired drug levels, local or systemic, depending upon the mode of administration. The doses may be given in one or several administrations per day. As one example, if daily doses are required, daily doses may be from about 0.01 mg/kg/day to about 1000 mg/kg/day, and in some embodiments, from about 0.1 to about 100 mg/kg/day or from about 1 mg/kg/day to about 10 mg/kg/day. Parenteral administration, in some cases, may be from one to several orders of magnitude lower dose per day, as compared to oral doses. For example, the dosage of an active compound when parenterally administered may be between about 0.1 micrograms/kg/day to about 10 mg/kg/day, and in some embodiments, from about 1 microgram/kg/day to about 1 mg/kg/day or from about 0.01 mg/kg/day to about 0.1 mg/kg/day. In some embodiments, the concentration of the active compound(s), if administered systemically, is at a dose of about 1.0 mg to about 2000 mg for an adult of kg body weight, per day. In other embodiments, the dose is about 10 mg to about 1000 mg/70 kg/day. In yet other embodiments, the dose is about 100 mg to about 500 mg/70 kg/day. Preferably, the concentration, if applied topically, is about 0.1 mg to about 500 mg/gm of ointment or other base, more preferably about 1.0 mg to about 100 mg/gm of base, and most preferably, about 30 mg to about 70 mg/gm of base. The specific concentration partially depends upon the particular composition used, as some are more effective than others. The dosage concentration of the composition actually administered is dependent at least in part upon the particular physiological response being treated, the final concentration of composition that is desired at the site of action, the method of administration, the efficacy of the particular composition, the longevity of the particular composition, and the timing of administration relative to the severity of the disease. Preferably, the dosage form is such that it does not substantially deleteriously affect the mammal. The dosage can be determined by one of ordinary skill in the art employing such factors and using no more than routine experimentation. In the event that the response of a particular subject is insufficient at such doses, even higher doses (or effectively higher doses by a different, more localized delivery route) may be employed to the extent that subject tolerance permits. Multiple doses per day are also contemplated in some cases to achieve appropriate systemic levels within the subject or within the active site of the subject. In some cases, dosing amounts, dosing schedules, routes of administration, and the like may be selected as described herein, whereby therapeutically effective levels for the treatment of cancer are provided.

In certain embodiments where cancers are being treated, let-7 miRNA and/or let-7 mimetics of the invention may be administered to a subject who has a family history of cancer, or to a subject who has a genetic predisposition for cancer, for example breast cancer. In other embodiments, let-7 miRNA and/or let-7 mimetics are administered to a subject who has reached a particular age, or to a subject more likely to get cancer. In yet other embodiments, the let-7 miRNA and/or let-7 mimetics are administered to subjects who exhibit symptoms of cancer (e.g., early or advanced). In still other embodiments, the composition may be administered to a subject as a preventive measure.

In some embodiments, the inventive composition may be administered to a subject based on demographics or epidemiological studies, or to a subject in a particular field or career. In some embodiments, the miRNA and/or miRNA mimetic, for example let-7 or let-7 mimetic are administered to a subject that has had a prior therapy, for example cancer therapy. Examples of such therapies include, but are not limited to, surgery, chemotherapy, radiotherapy, thermotherapy, immunotherapy, hormone therapy and laser therapy.

Administration of let-7 miRNA and/or let-7 mimetics of the invention to a subject may be accomplished by any medically acceptable method which allows the composition to reach its target. The particular mode selected will depend of course, upon factors such as those previously described, for example, the particular composition, the severity of the state of the subject being treated, the dosage required for therapeutic efficacy, etc. As used herein, a "medically acceptable" mode of treatment is a mode able to produce effective levels of the active compound(s) of the composition within the subject without causing clinically unacceptable adverse effects.

The methods to deliver let-7 miRNA and mimetics thereof to the cell or subject useful in the present invention are well known in the art, and include chemical transfection using lipid-based, amine based and polymer based techniques, viral vectors and combinations thereof (see, for example, products from Ambion Inc., Austin, Tex.; and Novagen, EMD Biosciences, Inc, an Affiliate of Merck KGaA, Darmstadt, Germany).

Other described ways to deliver miRNA and/or miRNA mimetics is from vectors, such as lentiviral constructs, and introducing siRNA molecules into cells using electroporation. However, feline FIV lentivirus vectors which are based on the feline immunodeficiency virus (FIV) retrovirus and the HIV lentivirus vector system, which is based on the human immunodeficiency virus (HIV), carry with them problems related to permanent integration. Electroporation is also useful in the present invention, although it is generally only used to deliver siRNAs into cells in vitro.

The target cell types to which miRNA and/or miRNA mimetics can be delivered using the methods of the invention include eukaryotic cells including, but not limited to hepatocytes, myocytes, neural cells, lipocytes, lymphocytes, macrophages, cardiac cells, endothelial cells, epithelial cells, and the like. In one embodiment, the target cell type is a tumor cell or a cancer cell including, but not limited to, a lung cancer cell, retinal cancer cell, breast cancer cell, ovarian cancer cell, prostate cancer cell, head and neck cancer cell, lymphoma cell, melanoma cell, glioma cell, bladder cancer cell, genital-urinary cancer cell, stomach cancer cell, pancreatic cancer cell, liver cancer cell, kidney cancer cell, gastrointestinal cancer and the like. In some embodiments, the target cells are cancer stem cells. In alternative embodiments, the target cells are selected from the group consisting of human lymphocytes, human dendritic cells, human adult stem cells and embryonic stem cells.

In one embodiment, the nucleic acid encoding a miRNA and/or miRNA mimetics, for example let-7 miRNA or mimetic thereof is present on a vector. These vectors include a sequence encoding mature let-7 microRNA and in vivo expression elements. In some embodiments, these vectors include a sequence encoding let-7 pre-miRNA and in vivo expression elements such that the let-7 pre-miRNA is expressed and processed in vivo into a mature let-7 miRNA. In another embodiment, these vectors include a sequence encoding the let-7 pri-miRNA gene and in vivo expression elements. In this embodiment, the primary transcript is first processed to produce the stem-loop precursor miRNA molecule. The stem-loop precursor is then processed to produce the mature let-7 microRNA.

In some embodiments, the miRNA and/or miRNA mimetics, for example let-7 and let-7 mimetics can be delivered in vivo and in vitro. The in vivo delivery as used herein means delivery of the miRNA and/or miRNA mimetic, for example let-7 and let-7 mimetic into a living subject, including human. The in vitro delivery as used herein means delivery of miRNA and/or miRNA mimetic, for example let-7 and let-7 mimetic into cells and organs outside a living subject.

Vectors include, but are not limited to, plasmids, cosmids, phagemids, viruses, other vehicles derived from viral or bacterial sources that have been manipulated by the insertion or incorporation of the nucleic acid sequences for producing the microRNA, and free nucleic acid fragments which can be attached to these nucleic acid sequences. Viral and retroviral vectors are a preferred type of vector and include, but are not limited to, nucleic acid sequences from the following viruses: retroviruses, such as: Moloney murine leukemia virus; Murine stem cell virus, Harvey murine sarcoma virus; marine mammary tumor virus; Rous sarcoma virus; adenovirus; adeno-associated virus; SV40-type viruses; polyoma viruses; Epstein-Barr viruses; papilloma viruses; herpes viruses; vaccinia viruses; polio viruses; and RNA viruses such as any retrovirus. One of skill in the art can readily employ other vectors known in the art.

Viral vectors are generally based on non-cytopathic eukaryotic viruses in which non-essential genes have been replaced with the nucleic acid sequence of interest. Non-cytopathic viruses include retroviruses, the life cycle of which involves reverse transcription of genomic viral RNA into DNA with subsequent proviral integration into host cellular DNA.

Retroviruses have been approved for human gene therapy trials. Genetically altered retroviral expression vectors have general utility for the high efficiency transduction of nucleic acids in viva. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W.H. Freeman Co., New York (1990) and Murry, E. J. Ed. "Methods in Molecular L Biology," vol. 7, Humana Press, Inc., Cliffton, N.J. (1991).

In some embodiments the "in vivo expression elements" are any regulatory nucleotide sequence, such as a promoter sequence or promoter-enhancer combination, which facilitates the efficient expression of the nucleic acid to produce the microRNA. The in vivo expression element may, for example, be a mammalian or viral promoter, such as a constitutive or inducible promoter and/or a tissue specific promoter. Examples of which are well known to one of ordinary skill in the art. Constitutive mammalian promoters include, but are not limited to, polymerase promoters as well as the promoters for the following genes: hypoxanthine phosphoribosyl transferase (HPTR), adenosine deaminase, pyruvate kinase, and beta.-actin. Exemplary viral promoters which function constitutively in eukaryotic cells include, but are not limited to, promoters from the simian virus, papilloma virus, adenovirus, human immunodeficiency virus (HIV), Rous sarcoma virus, cytomegalovirus, the long terminal repeats (LTR) of moloney leukemia virus and other retroviruses, and the thymidine kinase promoter of herpes simplex virus. Other constitutive promoters are known to those of ordinary skill in the art. Inducible promoters are expressed in the presence of an inducing agent and include, but are not limited to, metal-inducible promoters and steroid-regulated promoters. For example, the metallothionein promoter is induced to promote transcription in the presence of certain metal ions. Other inducible promoters are known to those of ordinary skill in the art.

Examples of tissue-specific promoters include, but are not limited to, the promoter for creatine kinase, which has been used to direct expression in muscle and cardiac tissue and immunoglobulin heavy or light chain promoters for expression in B cells. Other tissue specific promoters include the human smooth muscle alpha-actin promoter. Exemplary tissue-specific expression elements for the liver include but are not limited to HMG-COA reductase promoter, sterol regulatory element 1, phosphoenol pyruvate carboxy kinase (PEPCK) promoter, human C-reactive protein (CRP) promoter, human glucokinase promoter, cholesterol L 7-alpha hydroylase (CYP-7) promoter, beta-galactosidase alpha-2,6 sialylkansferase promoter, insulin-like growth factor binding protein (IGFBP-1) promoter, aldolase B promoter, human transferrin promoter, and collagen type I promoter. Exemplary tissue-specific expression elements for the prostate include but are not limited to the prostatic acid phosphatase (PAP) promoter, prostatic secretory protein of 94 (PSP 94) promoter, prostate specific antigen complex promoter, and human glandular kallikrein gene promoter (hgt-1). Exemplary tissue-specific expression elements for gastric tissue include but are not limited to the human H+/K+-ATPase alpha subunit promoter. Exemplary tissue-specific expression elements for the pancreas include but are not limited to pancreatitis associated protein promoter (PAP), elastase 1 transcriptional enhancer, pancreas specific amylase and elastase enhancer promoter, and pancreatic cholesterol esterase gene promoter. Exemplary tissue-specific expression elements for the endometrium include, but are not limited to, the uteroglobin promoter. Exemplary tissue-specific expression elements for adrenal cells include, but are not limited to, cholesterol side-chain cleavage (SCC) promoter. Exemplary tissue-specific expression elements for the general nervous system include, but are not limited to, gamma-gamma enolase (neuron-specific enolase, NSE) promoter. Exemplary tissue-specific expression elements for the brain include, but are not limited to, the neurofilament heavy chain (NF-H) promoter. Exemplary tissue-specific expression elements for lymphocytes include, but are not limited to, the human CGL-1/granzyme B promoter, the terminal deoxy transferase (TdT), lambda 5, VpreB, and Ick (lymphocyte specific tyrosine protein kinase p561ck) promoter, the humans CD2 promoter and its 3' transcriptional enhancer, and the human NK and T cell specific activation (NKGS) promoter. Exemplary tissue-specific expression elements for the colon include, but are not limited to, pp60c-src tyrosine kinase promoter, organ-specific neoantigens (OSNs) promoter, and colon specific antigen-P promoter.

In some embodiments, tissue-specific expression elements for breast cells include, but are not limited to, the human alpha-lactalbumin promoter. Exemplary tissue-specific expression elements for the lung include, but are not limited to, the cystic fibrosis transmembrane conductance regulator (CFTR) gene promoter.

Other elements aiding specificity of expression in a tissue of interest can include secretion leader sequences, enhancers, nuclear localization signals, endosmolytic peptides, etc. Preferably, these elements are derived from the tissue of interest to aid specificity. In general, the in vivo expression element shall include, as necessary, 5' non-transcribing and 5' non-translating sequences involved with the initiation of transcription. They optionally include enhancer sequences or upstream activator sequences.

let-7 miRNA or let-7 mimetics, either alone, expressed as a viral vector or complexed to targeting moieties can be delivered using any delivery system such as topical administration, subcutaneous, intramuscular, intraperitoneal, intrathecal and intravenous injections, catheters for delivering the miRNA and miRNA mimetic, for example let-7 and/or let-7 mimetic into, for example, a specific organ, such as breast, brain, liver, heart or kidneys, or into, for example, a specific location having a cancer stem cell, and/or affected with malignant growth or cancer. The let-7 miRNA or let-7 mimetics, either alone or complexed to targeting moieties can also be administered vaginally.

A pharmaceutically acceptable carrier as used herein means any pharmaceutically acceptable means to mix and/or deliver let-7 miRNA and/or let-7 mimetics, either alone or complexed to targeting moieties to a subject, or in combination with one or more pharmaceutically acceptable ingredients.

In the preparation of pharmaceutical formulations containing let-7 miRNA and/or let-7 mimetics, either alone or complexed to targeting moieties of the present invention in the form of dosage units for oral administration the compound selected may be mixed with solid, powdered ingredients, such as lactose, saccharose, sorbitol, mannitol, starch, arnylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture is then processed into granules or pressed into tablets.

Soft gelatin capsules may be prepared with capsules containing a mixture of the active compound or compounds of the invention in vegetable oil, fat, or other suitable vehicle for soft gelatin capsules. Hard gelatin capsules may contain granules of the active compound. Hard gelatin capsules may also contain let-7 miRNA and/or let-7 mimetics, either alone or complexed to targeting moieties in combination with solid powdered ingredients such as lactose, saccharose, sorbitol, mannitol, potato starch, corn starch, arnylopectin, cellulose derivatives or gelatin.

Dosage units for rectal or vaginal administration may be prepared (i) in the form of suppositories which contain the active substance, i.e. let-7 miRNA and/or let-7 mimetics, either alone or complexed to targeting moieties, mixed with a neutral fat base; (ii) in the form of a gelatin rectal capsule which contains the active substance in a mixture with a vegetable oil, paraffin oil or other suitable vehicle for gelatin rectal capsules; (iii) in the form of a ready-made micro enema; or (iv) in the form of a dry micro enema formulation to be reconstituted in a suitable solvent just prior to administration.

Liquid preparations for oral administration may be prepared in the form of syrups or suspensions, e.g. solutions or suspensions containing from 0.2% to 20% by weight of the active ingredient and the remainder consisting of sugar or sugar alcohols and a mixture of ethanol, water, glycerol, propylene glycol and polyethylene glycol. If desired, such liquid preparations may contain coloring agents, flavoring agents, saccharin and carboxymethyl cellulose or other thickening agents. Liquid preparations for oral administration may also be prepared in the form of a dry powder to be reconstituted with a suitable solvent prior to use.

Solutions for parenteral administration may be prepared as a solution of a compound of the invention in a pharmaceutically acceptable solvent, preferably in a concentration from 0.1% to 10% by weight. These solutions may also contain stabilizing ingredients and/or buffering ingredients and are dispensed into unit doses in the form of ampoules or vials. Solutions for parenteral administration may also be prepared as a dry preparation to be reconstituted with a suitable solvent extemporaneously before use.

The methods of the present invention to also encompass delivery of let-7 miRNA and/or let-7 mimetics, either alone or complexed to targeting moieties orally in granular form including sprayed dried particles, or complexed to form micro or nanoparticles.

The subject or individual as referred to herein and throughout the specification includes mammals, such as murine, specifically mice and rats, bovine, and primates, such as human.

Other oral let-7 miRNA and/or let-7 mimetics for use with the invention include solutions or suspensions in aqueous or non-aqueous liquids such as a syrup, an elixir, or an emulsion. In another set of embodiments, the let-7 miRNA and/or let-7 mimetics may be used to fortify a food or a beverage.

Injections can be e.g., intravenous, intratumoral, intradermal, subcutaneous, intramuscular, or interperitoneal. The composition can be injected interdermally for treatment or prevention of infectious disease, for example. In some embodiments, the injections can be given at multiple locations. Implantation includes inserting implantable drug delivery systems, e.g., microspheres, hydrogels, polymeric reservoirs, cholesterol matrixes, polymeric systems, e.g., matrix erosion and/or diffusion systems and non-polymeric systems, e.g., compressed, fused, or partially-fused pellets. Inhalation includes administering the composition with an aerosol in an inhaler, either alone or attached to a carrier that can be absorbed. For systemic administration, it may be preferred that the composition is encapsulated in liposomes.

In some embodiments, the miRNA or let-7 mimetic and/or nucleic acid encoding such, for example vectors are provided in a manner which enables tissue-specific uptake of the agent and/or nucleic acid delivery system. Techniques include using tissue or organ localizing devices, such as wound dressings or transdermal delivery systems, using invasive devices such as vascular or urinary catheters, and using interventional devices such as stents having drug delivery capability and configured as expansive devices or stent grafts.

let-7 miRNA and/or let-7 mimetics of the invention may also be delivered using a bioerodible or bioresorbable implant by way of diffusion, or more preferably, by degradation of the polymeric matrix. Exemplary synthetic polymers which can be used to form the biodegradable delivery system include: polyamides, polycarbonates, polyalkylenes, s polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, lo hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), i poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene, polyvinylpyrrolidone, and polymers of lactic; acid and glycolic acid, polyanhydrides, poly(ortho)esters, poly (butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifcations routinely made by those skilled in the art), albumin and other hydrophilic proteins, zein and other prolamines and 2s hydrophobic proteins, copolymers and mixtures thereof. In general, these materials degrade either by enzymatic hydrolysis or exposure to water in vivo, by surface or bulk erosion. Examples of non-biodegradable polymers include ethylene vinyl acetate, poly(meth)acrylic acid, polyamides, copolymers and mixtures thereof.

Bioadhesive polymers of particular interest include bioerodible hydrogels described by H. S. Sawhney, C. P. Pathak and J. A. Hubell in Macromolecules, (1993) i 26:581-587, the teachings of which are incorporated herein, polyhyaluronic acids, casein, gelatin, glutin, polyanhydrides, polyacrylic acid, alginate, chitosan, poly(methyl I methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

In certain embodiments of the invention, the administration of the let-7 miRNA and/or let-7 mimetics of the invention may be designed so as to result in sequential exposures to the composition over a certain time period, for example, hours, days, weeks, months or years. This may be accomplished, for example, by repeated administrations of let-7 miRNAs and/or let-7 mimetics of the invention by one of the methods described above, or by a sustained or controlled release delivery system in which the let-7 miRNA and/or let-7 mimetics are delivered over a prolonged period without repeated administrations. Administration of the let-7 miRNA and/or let-7 mimetics using such a delivery system may be, for example, by oral dosage forms, bolus injections, transdermal patches or subcutaneous implants. Maintaining a substantially constant concentration of the composition may be preferred in some cases.

Other delivery systems suitable for use with the present invention include time release, delayed release, sustained release, or controlled release delivery systems. Such systems may avoid repeated administrations in many cases, increasing convenience to; the subject and the physician. Many types of release delivery systems are available and known to those of ordinary skill in the art. They include, for example, polymer-based systems such as polylactic and/or polyglycolic acids, polyanhydrides, polycaprolactones, copolyoxalates, polyesteramides, polyorthoesters, polyhydroxybutyric acid, and/or combinations of these. Microcapsules of the foregoing polymers containing drugs are described in, for example, U.S. Pat. No. 5,075,109. Other examples include nonpolymer systems that are lipid-based including sterols such as cholesterol, cholesterol esters, and fatty acids or neukal fats such as mono-, di- and triglycerides; hydrogel release systems; liposome-based systems; phospholipid based-systems; silastic systems; peptide based systems; wax coatings; compressed tablets using conventional binders and excipients; or partially fused implants. Specific examples include, but are not limited to, erosional systems in which the composition is contained in a form within a matrix (for example, as described in U.S. Pat. Nos. 4,452,775, 4,675, 189, 5,736,152, 4,667,014, 4,748,034 and—29 5,239,660), or diffusional systems in which an active component controls the release rate I (for example, as described in U.S. Pat. Nos. 3,832,253, 3,854,480, 5,133,974 and 5,407,686). The formulation may be as, for example, microspheres, hydrogels, polymeric reservoirs, cholesterol matrices, or polymeric systems. In some embodiments, s the system may allow sustained or controlled release of the composition to occur, for example, through control of the diffusion or erosion/degradation rate of the formulation containing the composition. In addition, a pump-based hardware delivery system may be used to deliver one or more embodiments of the invention.

Examples of systems in which release occurs in bursts includes, e. g., systems in which the composition is entrapped in liposomes which are encapsulated in a polymer matrix, the liposomes being sensitive to specific stimuli, e.g., temperature, pH, light or a degrading enzyme and systems in which the composition is encapsulated by a tonically-coated microcapsule with a microcapsule core degrading enzyme. Examples of systems in which release of the inhibitor is gradual and continuous include, e.g., erosional Is systems in which the composition is contained in a forth within a matrix and effusional systems in which the composition permeates at a controlled rate, e.g., through a polymer. Such sustained release systems can be e.g., in the form of pellets, or capsules.

Examples of systems in which release occurs in bursts includes, e. g., systems in which the composition is entrapped in liposomes which are encapsulated in a polymer matrix, the liposomes being sensitive to specific stimuli, e.g., temperature, pH, light or a degrading enzyme and systems in which the composition is encapsulated by an tonically-coated microcapsule with a microcapsule core degrading enzyme. Examples of systems in which release of the inhibitor is gradual and continuous include, e.g., erosional systems in which the composition is contained in a form within a matrix and effusional systems in which the composition permeates at a controlled rate, e.g., through a polymer. Such sustained release systems can be e.g., in the form of pellets, or capsules.

Use of a long-term release implant may be particularly suitable in some; embodiments of the invention. "Long-term release," as used herein, means that the implant containing let-7 miRNA and/or let-7 mimetics are constructed and arranged to deliver therapeutically effective levels of the composition for at least 30 or 45 days, and preferably at least 60 or days, or even longer in some cases. Long-term release implants are well known to those of ordinary skill in the art, and include some of the release systems described above.

In some embodiments, the let-7 miRNA and/or let-7 mimetics of the invention may include pharmaceutically acceptable carriers with formulation ingredients such as salts, carriers, buffering agents, emulsifiers, diluents, excipients, chelating agents, fillers, drying agents, antioxidants, antimicrobials, preservatives, binding agents, bulking agents, silicas, solubilizers, or stabilizers that may be used with the active compound. For example, if the formulation is a liquid, the carrier may be a solvent, partial solvent, or non-solvent, and may be aqueous or organically based. Examples of suitable formulation ingredients—30 include diluents such as calcium carbonate, sodium carbonate, lactose, kaolin, calcium I phosphate, or sodium phosphate; granulating and disintegrating agents such as corn starch or algenic acid; binding agents such as starch, gelatin or acacia; lubricating agents such as magnesium stearate, stearic acid, or talc; time-delay materials such as glycerol monostearate or glycerol distearate; suspending agents such as sodium carboxymethylcellulose, methylcellulose, hydroxypropylmethylcellulose, sodium alginate, polyvinylpyrrolidone; dispersing or wetting agents such as lecithin or other naturally-occurring phosphatides; thickening agents such as cetyl alcohol or beeswax; buffering agents such as acetic acid and salts thereof, citric acid and salts thereof, boric lo acid and salts thereof, or phosphoric acid and salts thereof; or preservatives such as benzalkonium chloride, chlorobutanol, parabens, or thimerosal. Suitable carrier concentrations can be determined by those of ordinary skill in the art, using no more than routine experimentation. The compositions of the invention may be formulated into i preparations in solid, semi-solid, liquid or gaseous forms such as tablets, capsules, elixirs, powders, granules, ointments, solutions, depositories, inhalants or injectables. Those of ordinary skill in the art will know of other suitable formulation ingredients, or will be able to ascertain such, using only routine experimentation.

Preparations include sterile aqueous or nonaqueous solutions, suspensions and; emulsions, which can be isotonic with the blood of the subject in certain embodiments. Examples of nonaqueous solvents are polypropylene glycol, polyethylene glycol, vegetable oil such as olive oil, sesame oil, coconut oil, *arachis* oil, peanut oil, mineral oil, injectable organic esters such as ethyl oleate, or fixed oils including synthetic mono or all-glycerides. Aqueous carriers include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents and inert gases and the like. In addition, so sterile, fixed oils are conventionally employed as a solvent or suspending medium. For i this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc administrations can be found in Remington's Pharmaceutical Sciences, Mack Publishing Co., Easton, Pa. Those of skill in the art can readily determine the various parameters for preparing and formulating the compositions of the invention without resort to undue experimentation.

In some embodiments, the present invention encompasses let-7 miRNA and/or let-7 mimetics of the invention in association or contact with a suitable carrier, which may constitute one or more accessory ingredients. The final compositions may be prepared by any suitable technique, for example, by uniformly and intimately bringing the composition into association with a liquid carrier, a finely divided solid carrier or both, optionally with one or more formulation ingredients as previously described, and then, if necessary, shaping the product. In some embodiments, the compositions of the present invention may be present as pharmaceutically acceptable salts. The term "pharmaceutically acceptable salts" includes salts of the composition, prepared in combination with, for example, acids or bases, depending on the particular compounds found within the composition and the treatment modality desired. Pharmaceutically acceptable salts can be prepared as; alkaline metal salts, such as lithium, sodium, or potassium salts, or as alkaline earth salts, such as beryllium, magnesium or calcium salts. Examples of suitable bases that may be used to form salts include ammonium, or mineral bases such as sodium hydroxide, lithium hydroxide, potassium hydroxide, calcium hydroxide, magnesium hydroxide, and the like. Examples of suitable acids that may be used to form salts include inorganic or mineral acids such as hydrochloric, hydrobromic, hydroiodic, hydrofluoric, nitric, carbonic, monohydrogencarbonic, phosphoric, monohydrogenphosphoric, dihydrogenphosphoric, sulfuric, monohydrogensulfuric, phosphorous acids and the like.

Other suitable acids include organic acids, for example, acetic, propionic, isobutyric, maleic, malonic, benzoic, succinic, suberic, fumaric, mandelic, phthalic, benzenesulfonic, p-tolylsulfonic, citric, tartaric, methanesulfonic, glucuronic, galacturonic, salicylic, formic, naphthalene-2-sulfonic, and the like. Still other suitable i acids include amino acids such as arginate, aspartate, glutamate, and the like.

Dosages for a particular patient can be determined by one of ordinary skill in the art using conventional considerations, (e.g. by means of an appropriate, conventional pharmacological protocol). A physician may, for example, prescribe a relatively low dose at first, subsequently increasing the dose until an appropriate response is obtained. The dose administered to a patient is sufficient to effect a beneficial therapeutic response in the patient over time, or, e.g., to reduce symptoms, or other appropriate activity, depending on the application. The dose is determined by the efficacy of the particular formulation, and the activity, stability or serum half-life of the miRNA employed and the condition of the patient, as well as the body weight or surface area of the patient to be treated. The size of the dose is also determined by the existence, nature, and extent of any adverse side-effects that accompany the administration of a particular vector, formulation, or the like in a particular subject. Therapeutic compositions comprising one or more nucleic acids are optionally tested in one or more appropriate in vitro and/or in viva animal models of disease, to confirm efficacy, tissue metabolism, and to estimate dosages, according to methods well known in the art. In particular, dosages can be initially determined by activity, stability or other suitable measures of treatment vs. non-treatment (e.g., comparison of treated vs. untreated cells or animal models), in a relevant assay. Formulations are administered at a rate determined by the LD50 of the relevant formulation, and/or observation of any side-effects of the nucleic acids at various concentrations, e.g., as applied to the mass and overall health of the patient. Administration can be accomplished via single or divided doses.

In vitro models can be used to determine the effective doses of the nucleic acids as a potential cancer treatment. Suitable in vitro models include, but are not limited to, proliferation assays of cultured tumor cells, growth of cultured tumor cells in soft agar (see Freshney, (1987) Culture of Animal Cells: A Manual of Basic Technique, Wily-Liss, New York, N.Y. Ch 18 and Ch 21), tumor systems in nude mice as described in Giovanella et al., I J. Natl. Can. Inst., 52: 921-30 (1974), mobility and invasive potential of tumor cells in Boyden Chamber assays as described in Pilkington et al., Anticancer Res., 17: 4107-9 (1997), and angiogenesis assays such as induction of vascularization of the chick chorioallantoic membrane or induction of vascular endothelial cell migration as described in Ribatta et al., Intl. J. Dev. Biol., 40: 1189-97 (1999) and Li et al., Clin. Exp. Metastasis, 17:423-9 (1999), respectively. Suitable tumor cells lines are available, e.g. from American Type Tissue Culture Collection catalogs.

In vivo models are the preferred models to determine the effective doses of nucleic acids described above as potential cancer treatments. Suitable in vivo models include, but are not limited to, mice that carry a mutation in the KRAS oncogene (Lox-Stop-Lox K-RasGi2D mutants, Kras24TYj) available from the National Cancer Institute (NCI) Frederick Mouse Repository. Other mouse models known in the art and that are available include but are not limited to models for breast cancer, gastrointestinal cancer, hematopoietic cancer, lung cancer, mammary gland cancer, nervous system cancer, ovarian cancer, prostate cancer, skin cancer, cervical cancer, oral cancer, and sarcoma cancer (see http://emice.nci.nih. gov/mouse_models/).

In determining the effective amount of the miRNA and mimetic thereof, for example let-7 and let-7 mimetic to be administered in the treatment or prophylaxis of disease the physician evaluates circulating plasma levels, formulation toxicities, and progression of the disease.

The dose administered to a 70 kilogram subject is typically in the range equivalent to dosages of currently-used therapeutic antisense oligonucleotides such as Vikavene (fomivirsen sodium injection) which is approved by the FDA for treatment of cytomegaloviral RNA, adjusted for the altered activity or serum half-life of the relevant composition.

In some embodiments, the miRNA and miRNA mimetic, for example let-7 miRNA and/or mimetics thereof of the present invention described herein can supplement the treatment of any known additional therapy, including, but not limited to, antibody administration, vaccine administration, administration of cytotoxic agents, natural amino acid polypeptides, nucleic acids, nucleotide analogues, and biologic response modifiers. In some embodiments, additional therapy is, for example, surgery, chemotherapy, radiotherapy, thermotherapy, immunotherapy, hormone therapy and laser therapy. In some embodiments, the additional therapy is chemotherapy. Two or more combined compounds may be used together or sequentially with miRNAs or miRNA mimetics, for example the let-7 miRNA and/or let-7 mimetics of the present invention. The let-7 miRNA and/or let-7 mimetics can be administered before the additional therapy, after the additional therapy or at the same time as the additional therapy. In some embodiments, the let-7 miRNA and let-7 mimetics are administered a plurality of times, and in other embodiments, the additional therapies are also administered a plurality of times.

In some embodiments of the invention miRNA and/or miRNA mimetics, for example, nucleic acids encoding the let-7 miRNA and let-7 mimetics can also be administered in therapeutically effective amounts as a portion of an anti-cancer cocktail. An anti-cancer cocktail is a mixture, for example of a least one let-7 miRNA and/or let-7 mimetic of the present invention with one or more additional anti-cancer agents in addition to a pharmaceutically acceptable carrier for delivery. The use of anti-cancer cocktails as a cancer treatment is routine. Anti-cancer agents that are well known in the art and can be used as a treatment in combination with the let-7 miRNA and mimetics thereof as described herein include, but are not limited to: Actinomycin D, Aminoglutethimide, Asparaginase, Bleomycin, Busulfan, Carboplatin, Carmustine, Chlorambucil, Cisplatin (cis-DDP), Cyclophosphamide, Cytarabine HCl (Cytosine arabinoside), Dacarbazine, Dactinomycin, Daunorubicin HCl, Doxorubicin HCl, Estramustine phosphate sodium, Etoposide (V16-213), Flosuridine, S-Fluorouracil (5-Fu), Flutamide, Hydroxyurea (hydroxycarb amide), Ifosfamide, Interferon Alpha-2 a, Interferon Alpha-2b, Leuprolide acetate (LHRH-releasing factor analog), Lomustine, Mechlorethamine HCl (nitrogen mustard), Melphalan, Mercaptopurine, Mesna, Methotrexate (MTX), Mitomycin, Mitoxantrone HCl, Ockeotide, Paclitaxel; Plicamycin, Procarbazine HCl, Streptozocin, Tamoxifen citrate, Thioguanine, Thiotepa, Vinblastine sulfate, Vincristine sulfate, Amsacrine, Azacitidine, Hexamethylmelamine, Interleukin-2, Mitoguazone, Pentostatin, Semustine, Teniposide, and Vindesine sulfate, and analogues thereof.

In certain embodiments, the pharmaceutical compositions comprising miRNA and/or miRNA mimetics, for example, pharmaceutical compositions comprising let-7 miRNA and/or let-7 mimetics can optionally further comprise one or more additional therapies or agents. In certain embodiments, the additional agent or agents are anti-cancer agents. In some embodiments, the therapeutic agents are chemotherapeutic agents, for example cisplatin, paxicital etc. In some embodiments, the therapeutic agents are radiotherapeutic agents. Examples of chemotherapeutic agents in the pharmaceutical compositions of this invention are, for example nitrogen mustards such as cyclophosphamide, ifosfamide, and melphalan; ethylenimines and methylmelamines such as hexamethylmelamine and thiotepa; pyrimidine analogs such as fluorouracil and fluorodeoxyuridine; *vinca* alkaloids such as vinblastine; epipodophyllotoxins such as etoposide and teniposide; antibiotics such as actinomycin D, doxorubicin, bleomycin, and mithramycin; biological response modifiers such as interferon, platinum coordination complexes such as cisplatin and carboplatin; estrogens such as diethylstilbestrol and ethinyl estradiol; antiandrogens such as flutamine; and gonadotropin releasing hormone analogs such as leuprolide. Other compounds such as decarbazine, nitrosoureas, methotrexate, diticene, and procarbazine are also effective. Of course, other chemotherapeutic agents which are known to those of ordinary skill in the art can readily be substituted as this list should not be considered exhaustive or limiting.

In some embodiments, the let-7 miRNA is administered to a subject with other anti-cancer therapies, for example cancer therapies to which the cancer was previously resistant or refractory.

Diseases to be Treated with Let-7 miRNA and Let-7 Mimetics

The invention provides methods for the treatment of any disease or disorder characterized by lack or reduced expression of let-7. In some embodiments, the disease is cancer. In some embodiments, the cancer comprises cancer stem cells. Cancer treatments promote tumor regression by inhibiting tumor cell proliferation, inhibiting angiogenesis (growth of new blood vessels that is necessary to support tumor growth) and/or prohibiting metastasis by reducing tumor cell motility or invasiveness. The effect of let-7 miRNA and let-7 mimetics on inhibiting cancer as disclosed herein and in the Examples is expected to be a general effect on cancer stem cells. That is, where a tumor of any type has a cancer stem cell, one would expect the approach as disclosed herein for using let-7 miRNA or let-7 mimetics thereof for the treatment and/or prevention of cancer to work. In particular, the methods and compositions as disclosed herein are likely to work in a subject that has any form of cancer where the cancer comprises cancer stem cells with a reduced level of let-7 miRNA as compared to non-stem cancer cells.

The therapeutic formulations described herein comprising let-7 miRNA and let-7 mimetics may be effective in adult and pediatric oncology including in solid phase tumors/malignancies, locally advanced tumors, human soft tissue sarcomas, metastatic cancer, including lymphatic metastases, blood cell malignancies including multiple myeloma, acute and chronic leukemias, and lymphomas, head and neck cancers including mouth cancer, larynx cancer and thyroid cancer, lung cancers including small cell carcinoma and non-small cell cancers, breast cancers including small cell carcinoma and ductal carcinoma, gastrointestinal cancers including esophageal cancer, stomach cancer, colon cancer, colorectal cancer and polyps associated with colorectal neoplasia, pancreatic cancers, liver cancer, urologic cancers including bladder cancer and prostate cancer, malignancies of the female genital tract including ovarian carcinoma, uterine (including endometrial) cancers, and solid tumor in the ovarian follicle, kidney cancers including renal cell carcinoma, brain cancers including intrinsic brain tumors, neuroblastoma, askocytic brain tumors, gliomas, metastatic tumor cell invasion in the central nervous system, bone cancers including osteomas, skin cancers including malignant melanoma, tumor progression of human skin keratinocytes, squamous cell carcinoma, basal cell carcinoma, hemangiopericytoma and Kaposi's sarcoma.

Therapeutic formulations can be administered in therapeutically effective dosages alone or in combination with adjuvant cancer therapy such as surgery, chemotherapy, radiotherapy, thermotherapy, immunotherapy, hormone therapy and laser therapy, to provide a beneficial effect, e.g. reducing tumor size, slowing rate of tumor growth, reducing cell proliferation of the tumor, promoting cancer cell death, inhibiting angiogenesis, inhibiting metastasis, or otherwise improving overall clinical condition, without necessarily eradicating the cancer.

Examples of cancers which can be treated by the methods and compositions as disclosed herein include, but are not limited to, bladder cancer; breast cancer; brain cancer including glioblastomas and medulloblastomas; cervical cancer; choriocarcinoma; colon cancer including colorectal carcinomas; endometrial cancer; esophageal cancer; gastric cancer; head and neck cancer; hematological neoplasms including acute lymphocytic and myelogenous leukemia, multiple myeloma, AIDS associated leukemias and adult T-cell leukemia lymphoma; intraepithelial neoplasms including Bowen's disease and Paget's disease, liver cancer; lung cancer including small cell lung cancer and non-small cell lung cancer; lymphomas including Hodgkin's disease and lymphocytic lymphomas; neuroblastomas; oral cancer including squamous cell carcinoma; osteosarcomas; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, synovial sarcoma and osteosarcoma; skin cancer including melanomas, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; transitional cancer and renal cancer including adenocarcinoma and Wilm's tumor. In one embodiment, the formulations comprising let-7 miRNA and let-7 mimetics are administered for treatment or prevention of breast cancer. In another embodiment, the formulations comprising let-7 miRNA and/or let-7 mimetics are administered for treatment or prevention of breast cancer.

In some embodiments, the formulations comprising let-7 miRNA and let-7 mimetics are administered for treatment or prevention of cancers which comprise at least one or a population stem cell cancer cells. Methods to identify a cancer stem cell are well known in the art, and include, for example the methods disclosed in U.S Patent Applications; 2008/0020407, 2007/0254319, 2007/0244046, 2007/0238127, 2007/0238137, 2007/0248628, 2007/0231325, 2007/0134794, and International Patent Applications WO2007147165, WO2007145901, WO2007145840, WO2007142711, WO2007124125, WO2007133250, WO2007118242, WO2007112097, WO2007118238, WO2007053648, WO2003102215, WO2003102215, WO2003050502, and Eurpoean Patent Applications, EP1726208, EP1697715 and EP1461023, which are all incorporated herein in their entirety by reference. Cancer stem cells were first detected in the blood cancer, acute myeloid leukemia (AML) (Lapidot et al, Nature 77:645-648 (1994)). More recently it has been demonstrated that malignant human breast tumors similarly harbor a small, distinct population of cancer stem cells enriched for the ability to form tumors in immunodeficient mice. An ESA+, CD44+, CD24−/low, Lin− cell population was found to be 50-fold enriched for tumorigenic cells compared to unfractionated tumor cells (Al-Hajj et al, PNAS 700:3983-3988 (2003)).

In addition, therapeutic let-7 miRNA and let-7 mimetics may be used for prophylactic treatment of cancer. There are hereditary conditions and/or environmental situations (e.g. exposure to carcinogens) known in the art that predispose an individual to developing cancers. Under these circumstances, it may be beneficial to treat these individuals with therapeutically effective doses of the nucleic acids encoding let-7 miRNA and let-7 mimetics to reduce the risk of developing cancers.

In one embodiment, the pharmaceutical compositions comprising let-7 miRNA and/or let-7 mimetics of the present invention are useful to be administered to a subject who has cancer regression. In another embodiment, the pharmaceutical compositions comprising let-7 miRNA and/or let-7 mimetics of the present invention are useful to be administered to a subject who has a therapy-resistant cancer, for example a chemotherapy resistant cancer. In some embodiments, the pharmaceutical compositions comprising let-7 miRNA and/or let-7 mimetics are useful to be administered to a subject who has cancer and has been exposed to adjuvant cancer therapies.

In another embodiment, the pharmaceutical compositions comprising let-7 miRNA and/or let-7 mimetics are useful to be administered to a subject with a malignant cancer. In some embodiments, the let-7 miRNA and/or let-7 mimetics of the present invention can be administered to a subject with a cancer or tumor comprising a cancer stem cell.

In one embodiment, the subject is assessed if they are at risk of having a metastasis or malignant cancer, the method comprising assessing a level of let-7 in a biological sample, and if the levels of let-7 are below a reference level, the subject is at risk of having a metastasis or a malignant cancer. In some embodiments, the biological sample is obtained from a biopsy tissue sample, and in some embodiments, the sample is from a tumor or cancer tissue sample. The level of let-7 can be determined by methods known by the skilled artisan, for example by northern blot analysis or RT-PCR as disclosed in the Examples. In some embodiments, the reference level is the level of let-7 that does not result in malignancy or a malignant cancer. In some embodiments, the reference level the based on the level of let-7 expression in a normal tissue sample, where in the tissue sample is a biological tissue sample from a tissue matched, species matched and age matched biological sample. In some embodiments, the reference level is based on a reference sample is from a non-malignant matched tissue sample. In some embodiments, the reference level is based on a reference sample from a non-stem cell cancer tissue sample.

In one embodiment, let-7 miRNA and/or let-7 mimetics in a suitable formulation may be administered to a subject who has a family history of cancer, or to a subject who has a genetic predisposition for cancer. In other embodiments, the nucleic acid in a suitable formulation is administered to a subject who has reached a particular age, or to a subject more likely to get cancer. In yet other embodiments, the nucleic acid in a suitable formulation is administered to subjects who exhibit symptoms of cancer (e. g., early or advanced). In still other embodiments, the nucleic acid in a suitable formulation may be administered to a subject as a preventive measure. In some embodiments, let-7 miRNA and let-7 mimetics in a suitable formulation may be administered to a subject based on demographics or epidemiological studies, or to a subject in a particular field or career.

Methods to Enrich for Cancer Stem Cells

One aspect of the present invention provides methods for the enrichment of cancer stem cells. Such methods can provide populations of cancer stem cells for the study of anti-tumor therapies or tumor development or for screening anti-tumor agents. Such cells can also be useful to identify miRNAs or other gene products that correlate with or confer "stemness" to such cells (see below). In such an embodiment, the methods comprise repeated selection for cancer stem cells by sequential transplantation of cancer cells and tumor formation under the selective pressure of low dose cancer therapy. The term "low dose" means a dose of chemotherapy that is used below the dose which is typically clinically administered as a treatment to eradicate a tumor in a subject. The term low dose also refers to a dose of the chemotherapy agent which is used to keep a cancer from reappearing or reoccurring, which is often referred in the clinic as a maintenance dose. In some embodiments, the term low dose is about half, or less than half, (i.e., <50%, e.g., ≤45%, ≤40%, ≤35%, ≤30%, or lower, but generally greater than 1%) (i.e., 50%) the dose which is normally administered clinically to treat or eradicate a tumor in a subject. In some embodiments, the method comprises obtaining cancer cells and transplanting the cancer cells into a mammal, and administering a low dose cancer therapy to the mammal for a period of time and sufficient for the cancer cells to develop into a tumor of a desired diameter. In some embodiments, the desired diameter of the tumor is about 2 cm in diameter. Once the desired diameter of the tumor is reached, the tumor is removed from the mammal and dissociated into single cells and re-transplanting into another mammal which is also administered a low dose cancer therapy during the formation of the tumor of a desired diameter. The process of tumor formation under low dose cancer therapy and re-transplantation is repeated a plurality of times. In some embodiments, the process is repeated 2,3, 4, 5 up to 10 times, and in some embodiments the process is repeated more than 10 times. In some embodiments, on the final removal of the tumor from the mammal, the tumor is dissociated into single cells and cultured as embryoid bodies (EBs), herein termed "mammospheres" in the Examples, which comprise a population of cells enriched for cancer stem cells.

In some embodiments, the cancer cells are any cancer cells, for example cancer cell lines or primary cancer cells obtained from a subject. In some embodiments, the cancer cells are human cancer cells. In alternative embodiments, the cancer cells are mammalian, for example rodent. In some embodiments, the cancer cell is a breast cancer cell, and in other embodiments the cancer cells can be from breast cancer, lung cancer, head and neck cancer, bladder cancer, stomach cancer, cancer of the nervous system, bone cancer, bone marrow cancer, brain cancer, colon cancer, esophageal cancer, endometrial cancer, gastrointestinal cancer, genitalurinary cancer, stomach cancer, lymphomas, melanoma, glioma, bladder cancer, pancreatic cancer, gum cancer, kidney cancer, retinal cancer, liver cancer, nasopharynx cancer, ovarian cancer, oral cancers, bladder cancer, hematological neoplasms, follicular lymphoma, cervical cancer, multiple myeloma, osteosarcomas, thyroid cancer, prostate cancer, colon cancer, prostate cancer, skin cancer, stomach cancer, testis cancer, tongue cancer, or uterine cancer.

In some embodiments, the cancer cells are transplanted into the mammal at the location most suitable for the specific cancer cell. For example, breast cancer cells are implanted in the mammary fat pad. In alternative embodiments, the cancer cells are implanted into brain where the cancer cells are obtained from brain cancer.

In some embodiments, the mammal used in the transplantation is a rodent, and in some embodiments the rodent is a genetically modified rodent, and in some embodiments the rodent is an immunocompromised rodent, for example but not limited to a NOD/SCID mouse.

In some embodiments the cancer therapy is chemotherapy, radiotherapy, thermotherapy, immunotherapy, hormone therapy and laser therapy. In some embodiments, more than one cancer therapy can be administered, and in some embodiments the cancer therapies can be administered at the same time or sequentially. In some embodiments, the cancer therapies can be of different types, for example one cancer therapy can be a chemotherapeutic agent and one cancer therapy is a immunotherapy, and in alternative embodiments the cancer therapies can be of the same types, for example two or more different chemotherapeutic agents. In some embodiments, the cancer therapies can be administered to the same mammal and in anther embodiment they can be administered to different mammals.

In some embodiments, administration is performed by any means and at any frequency intervals for sustained cancer therapy. For example, in some embodiments, the administration is continuous administration, and in some embodiments administration is, for example but not limited to twice a day, every day, every other day, twice a week, once a week, every other week or once a month. In some embodiments, administration is intravenous, intradermal, intramuscular, intraarterial, interlesional, percutaneous, subcutaneous, intraperitoneal or by aerosol.

The in vivo delivery as used herein means delivery of the miRNA and/or miRNA mimetic, for example let-7 and let-7 mimetic into a living subject, including human. The in vitro delivery as used herein means delivery of miRNA and/or miRNA mimetic, for example let-7 and let-7 mimetic into cells and organs outside a living subject.

In another embodiment, the present invention provides methods to identify miRNA that contribute to the self-proliferative capacity and/or tumorogenicity of cancer stem cells. The method comprises comparing the miRNA expression profile of a cancer stem cell, for example a cancer stem cell which has been enriched by the methods described herein, with the miRNA expression profile of a reference sample. In some embodiments, a reference is any biological sample. A difference in the level of expression of a miRNA in the cancer stem cell sample as compared with the level of expression of the same miRNA in a reference sample identifies that the miRNA contributes to, in whole or in part, to the self-proliferative capacity and/or tumorogenicity of the cancer stem cell. In this embodiment, the difference in the level of expression of the miRNA in the cancer stem cell as compared with the reference level is a statistically significant change, but generally is at least about 10%, for example, at least about 20%, or at least about 30%, or at least about 40%, or at least about 50%, or at least about 60%, or at least about 70%, or at least about 80% or at least about 90%, or at least about 100%, or at least about 2-fold, or at least about 2.5-fold, or at least about 3 fold, or at least about 5-fold, or at least about 10-fold or more, or any integer in between a 10% difference and a 10-fold difference or more.

In some embodiments, the reference sample is a plurality of cancer cells, and in some embodiments the cancer cell is a cancer cell from which the cancer stem cells was derived using the methods of the present invention or from a cell derived from the cancer stem cell, for example a differentiated cancer stem cell. A number of miRNA profiles from reference samples can be compared to the miRNA profile of the cancer stem cell.

In further embodiments, the present invention provides methods to assess the level of contribution of the miRNA identified to contribute to the cancer stem cell self-proliferative capability, the method comprising either introducing or inhibiting the miRNA in the cancer stem cell, depending if the miRNA being assessed is downregulated or upregulated respectively, in the cancer stem cell as compared with the reference sample.

In some embodiments, a cancer stem cell's self-proliferative capacity is determined by the ability of the cancer stem cell to form embryoid bodies (EBs) (or mammospheres) in culture. To assess the effect of the miRNA on the self-proliferative ability of the cancer stem cell, if the miRNA is downregulated in the cancer stem cell compared to the reference sample, and the miRNA or mimetic thereof is introduced back into the cancer stem cell and the ability of the cancer stem cell to form mammospheres or EBs in culture is reduced, the miRNA contributes to the self-proliferative ability and/or tumorogeneicity of the cancer stem cell. Similarly, if the miRNA is upregulated in the cancer stem cell as compared to the reference sample, and the expression and/or activity of the miRNA is inhibited in cancer stem cell and the ability of the cancer stem cell to form mammospheres or EBs in culture is reduced, the miRNA contributes to the self-proliferative ability and/or tumorogeneicity of the cancer stem cell.

EXAMPLES

Throughout this application, various publications are referenced. The disclosures of all of the publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods which occur to the skilled artisan are intended to fall within the scope of the present invention.

Methods

Primary Tumor Specimens.

Tumors were obtained following a protocol approved by the ethics committee of the No. 2 Affiliated Hospital of Sun-Yat-Sen University in China from 11 consented female patients (median age 52 years) with biopsy-diagnosed poorly differentiated invasive ductal carcinomas of the breast. Five patients received 4 cycles of neoadjuvant chemotherapy with 5-fluorouracil 500 mg/m$^2$, epirubicin 100 mg/m$^2$ and cyclophosphamide 500 mg/m$^2$ followed by modified radical resection of the breasts. Modified radical resection was performed in 6 cases without neoadjuvant chemotherapy. The average tumor size was 3.4 cm (range, 2.5-4.3 cm), and all patients had axillary lymph node metastasis. Surgical specimens were received in the laboratory within 20 min of surgery, and were immediate mechanically disaggregated and digested with collagenase as described[10]. Single cancer cells were obtained by filtration through a 30μ filter.

In-Vivo Enrichment of Breast Tumor-Initiating Cells.

Female NOD/LtSz-scid/scid (NOD/SCID) mice were bred and maintained under defined conditions at the Animal Experiment Center of Sun-Yat-Sen University, and all animal experiments were approved by the Animal Care and Use Committee of the Sun-Yat-Sen University. SKBR3 cells (ATCC) were passaged in NOD/SCID mice by injecting 2×10⁶ cells into the mammary fat pad of 5-week-old mice. To select for chemoresistant breast tumor-initiating cells, Epirubicin (8 mg/kg, Pharmacia and Upjohn) was injected into the tail vein weekly. Single cell suspensions were obtained by collagenase digestion as described[10] of tumor xenografts, removed when tumors reached ~2 cm in diameter. The dissociated cells were repetitively passaged in Epirubicin-treated NOD/SCID mice as above for 3 generations. Freshly isolated single tumor cells obtained from the $3^{rd}$-generation xenografts (SK-3rd) were used to generate mammosphere cultures.

Mammosphere Culture.

SK-3rd and SKBR3 cells were cultured in suspension at a clonal density of 1,000 cells/mL in serum-free DMEM-F12 (BioWhittaker), supplemented with B27 (1:50, Invitrogen), 20 ng/mL EGF (BD Biosciences), 0.4% bovine serum albumin (Sigma) and 4 μg/mL insulin (Sigma)[25]. Alternatively, single-cell suspension culture was obtained by suspending a single SK-3rd or SKBR3 cell in 200 μL of the above medium in 96-well plates. To propagate mammospheres in vitro, the spheres were collected by gentle centrifugation and were dissociated to obtain single cells enzymatically and mechanically as described[25]. Single cells were then cultured in suspension to generate mammospheres of the next generation. The percentage of wells with mammospheres was analyzed at indicated times, and the size of mammospheres (cells/sphere) was determined by dissociating and counting the cells in the spheres.

Generation of microRNA and shRNA-Expressing Lentiviruses.

Oligonucleotides encoding let-7a1 pre-miRNA[33] (SEQ ID NO: 7) or shRNA targeting H-RAS1[46] or eGFP were synthesized according to previously published sequences and cloned under the control of the U6 promoter in the lentiviral vector lentilox pLL3.7 as previously reported[47]. Generation of lentivirus vectors was performed as described[47] by co-transfecting pLL3.7 carrying the miRNA or shRNA expression cassette with helper plasmid pCMV-VSV-G and pHR'8.9ΔVPR in 293 T cells using FuGENE 6 (Roche). The viral supernatant was collected 48 hrs after transfection, and viral titers determined by transducing HeLa cells at serial dilutions and analyzing GFP expression by flow cytometry.

Transduction with Lentivirus Vectors.

SK-3rd cells dissociated from the primary mammospheres were spin-infected with 1 mL of lentiviral supernatant containing 8 μg/mL polybrene for 2 hr at a multiplicity of infection (MOI) of 1:5, followed by incubation for 2 hours at 37° C. Transduction efficiency, evaluated by GFP expression, was >90%.

Transfection with Let-7a ASO.

After washing in D-MEM medium without serum, SKBR3 cells were transfected in 24-well plates with 30 pmol of let-7 ASO or 30 pmol of a control lin-4 ASO (Ambion) using Lipofectamine 2000 overnight. Cells were harvested for further experiments 48 hr post-transfection.

miRNA Microarray Analysis.

Total RNA enriched for small RNAs was isolated using the mirVana RNA Isolation Kit (Ambion), and miRNAs were then excised from RNA electrophoresed through polyacrylamide gels. A poly(A) tail was appended to the 3'-end of miRNAs from all the above samples with a mixture of unmodified and amine-modified nucleotides (Ambion). The tailed samples were fluorescently labeled using an amine-reactive Cy3 dye (Amersham), and the unincorporated dyes were removed with glass fiber filters. The samples were hybridized for 14 hr onto slides arrayed with miRNA probes from the NCode™ miRNA Microarray Probe Set (Invitrogen). Slides were then washed 3×2 min in 2×SSC and scanned using a Generation β array scanner (Amersham Pharmacia). Fluorescence intensities for the Cy3-labeled samples were normalized by the median total Cy3 signal on the arrays. The signal intensity of each element was analyzed using ArrayVision (Imaging Research Ltd), and images were created with DMVS 2.0 software (Chipscreen Biosciences Ltd).

Northern Blot.

Northern blot for let-7 miRNA was performed as previously reported[33]. Briefly, 10 μg of RNA were fractionated on a 15% denaturing polyacrylamide gel. The RNA was then electrotransferred to Nytran Plus (Schleicher & Schuell, Inc., Keene, N. H.) at 200 mA for 2.5 hr, UV cross-linked at 1,200 μF, and prehybridized for 30 min at 40° C. in UltraHyb buffer (Ambion). The let-7 probe (5'-TACTATACAACC-TACTACCTCAATTTGCC; SEQ ID NO:12) was radiolabeled as described[33] and blots were hybridized in 10 mL of UltraHyb buffer (Ambion). After washing 2×5 min at room temperature in 2×SSC, 0.1% SDS and 3×10 min in 1×SSC, 0.1% SDS, the blots were analyzed on a phosphorimager (Molecular Dynamics). The process was repeated using a radiolabeled probe for U6 snRNA (5'-GCAGGGGC-CATGCTAATCTTCTCTGTATCG; SEQ ID NO:13)[42].

Quantitative RT-PCR.

Real-time reverse transcription PCR was performed using an ABI Prism 7900 Sequence Detection System (Perkin-Elmer Applied Biosystems). SYBR green (Molecular Probes) was used to detect PCR products. All reactions were done in a 25-μl reaction volume in triplicate. Primers for mature let-7a miRNA (Probe 1: SEQ ID NO:14 and SEQ ID NO:15) and U6 snRNA were from Ambion. PCR amplification consisted of 10 min of an initial denaturation step at 95° C., followed by 55 cycles of PCR at 95° C. for 30 s, 56° C. for 30 s and 72° C. for 15 s. Standard curves were generated and the relative amount of target gene mRNA was normalized to U6 snRNA. Specificity was verified by melt curve analysis and agarose gel electrophoresis. To quantify cancer metastasis in mouse lungs and livers, qRT-PCR for human hypoxanthine-guanine-phosphoribosyltransferase (hHPRT), was performed on Trizol (Life Technologies, Gaithersburg, Md.)-isolated total RNA using described primers for human HPRT (hHPRT) and mouse GAPDH (mGAPDH)[48]. Following reverse transcription for 30 min at 48° C. and Taq activation for 10 min at 95° C., 40 cycles of PCR at 95° C. for 20 sec, 55° C. for 30 sec, and 72° C. for 30 sec were performed.

Let-7 Luciferase Assay.

To evaluate the miRNA function of let-7, a pMIR-REPORT™ luciferase reporter vector with a let-7 target sequence (SEQ ID NO: 9) (as well as SEQ ID NO:10 and SEQ ID NO:11) was cloned into its 3'UTR (luc-let-7-ts) (Ambion) was used. The reporter vector plasmid was transfected using Lipofectamine 2000 according to the manufacturer's instruction. To correct for transfection efficiency, a luciferase reporter vector without a let-7 target was transfected in parallel. Luciferase activity was assayed by luciferase assay kit (Promega). let-7 miRNA function was expressed as percentage reduction in the luciferase activity of cells transfected with the reporter vector containing the let-7 target sequence compared to cells transfected with the vector without the let-7 target.

Western Blot.

Protein extracts were resolved through 12% SDS-PAGE, transferred to nitrocellulose membranes, probed with rabbit polyclonal antibodies against human H-RAS (Upstate) or human Oct-4 (Chemicon Int), and then with peroxidase-conjugated goat anti-rabbit Ig secondary antibody (Oncogene Research Product), and then visualized by chemiluminescence (Amersham).

Flow Cytometry.

For cell surface staining, unfixed cells were incubated with FITC-labeled anti-CD44 and PE-labeled anti-CD24 (PharMingen) at 4° C. For staining cytoplasmic antigens, cells were permeabilized with the Caltag Laboratories (Burlingame) Fix and Perm kit and stained with FITC-labeled CK14 and PE-labeled CK18 (Neomarkers). Cells were analyzed by flow cytometry on a FACScalibur instrument with CellQuest software (BD).

Cell Proliferation.

$^3$H-thymidine (1 µCi) was added for 6 h to $2\times10^4$ cells in octuplicate microtiter wells, before harvesting and analysis by scintillation counting using a Top Count microplate reader (Packard).

Tumor Implantation.

Indicated numbers of SKBR3 or SK-3rd cells dissociated from mammospheres were injected subcutaneously into the mammary fat pads of 5-week-old NOD/SCID mice. Mice were examined by palpation for tumor formation for up to 60 d. After tumors were detected, tumor size was measured every 3 d by calipers, and tumor volumes calculated as Volume $(mm^3)=L\times W^2\times 0.4$. Mice were sacrificed by cervical dislocation and the presence of tumors was confirmed by necropsy. Tumor xenografts as well as whole lung and liver tissues were harvested, weighed and snap-frozen in liquid nitrogen. Portions of the lung and liver tissues were used for real-time RT-PCR for human HPRT to evaluate metastasis. Cryosections (4 µm) were stained with hematoxylin and eosin and used for immunohistochemistry.

Immunohistochemistry.

Cryosections were stained using anti-human RAS (Upstate) or anti-human PCNA (BD Biosciences) mAb. Briefly, endogenous peroxidase activity was quenched by incubation with 3% hydrogen peroxide in methanol for 5 min. Sections were washed in phosphate buffered saline (PBS) and blocked for 1 h in a washing buffer containing 5% normal goat serum (Sigma Chemical Co. St Louis, Mo.). The primary antibody was added for incubation overnight at 4° C. After washing in PBS, slides were incubated with biotinylated goat anti-mouse Ig and then with streptavidin conjugated with horseradish peroxidase. After further washing in PBS, slides were developed with diaminobenzidine (DAB; Dako Corp. Carpinteria, Calif.) lightly counterstained with hematoxylin. Negative control slides were stained with isotype mouse immunoglobulin to replace primary antibodies. The percentage of H-RAS and PCNA-positive tumor cells was calculated by counting 1,000 tumor cells.

Statistics.

All in vitro experiments were performed either in triplicate or in pentuplicate. The results are described as mean±SD. Statistical analysis was performed by one-way analysis of variance (ANOVA) and comparisons among groups were performed by independent sample t-test or Bonferroni's multiple-comparison t-test.

Example 1

Low-Dose Chemotherapy Selects for Tumor-Initiating Breast Cancer Cells.

Figure 1B:
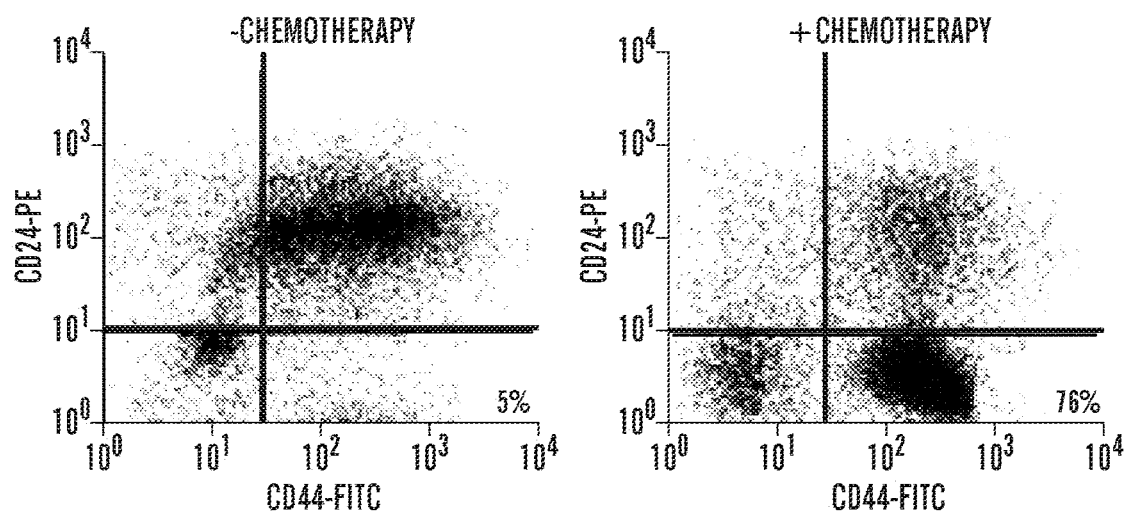

Resistance to chemotherapy distinguishes tumor-initiating cells from other cancer cells[1,2,17]. Accordingly, treatment with chemotherapy should enrich for tumor stem cells compared to more differentiated progeny. To examine this, the inventors compared the proportion of self-renewing cancer cells in primary breast cancer tissues surgically removed from patients with poorly differentiated invasive breast cancer who received four cycles of preoperative chemotherapy with tumors from matched untreated patients. Freshly isolated cells were cultured in suspension in medium supplemented with epidermal growth factor (EGF), B27 and insulin to generate mammospheres (or emboid bodies), a previously described method for culturing both mammary gland progenitor cells[25] and breast tumor-initiating cells[10]. The self-renewal potential of breast tumor-initiating cells can be gauged by their capacity to give rise to mammospheres[10]. From 5 patients who received neoadjuvant chemotherapy, 5.8±2.6% of tumor cells formed mammospheres after 15 d as compared with 0.4±0.3% from 6 chemotherapy-naïve patients, a 14-fold increase (P<0.001, FIG. 1a). Furthermore, the primary mammospheres from neoadjuvant chemotherapy patients could be passaged for at least 8-10 generations (end point of the study), while those from patients without chemotherapy vanished within 2-3 generations. Self-renewing breast cancer cells have been shown to be $CD44^+CD24^{-9,10,15}$; 70±8% of freshly examined primary tumor cells from chemotherapy-treated patients had this phenotype, while only 9±3% of cells from untreated patients did (P<0.001, FIG. 1b). These data demonstrate that neoadjuvant chemotherapies selectively enhance the proportionate survival of breast tumor-initiating cells in primary cancer tissues.

Figure 1C:
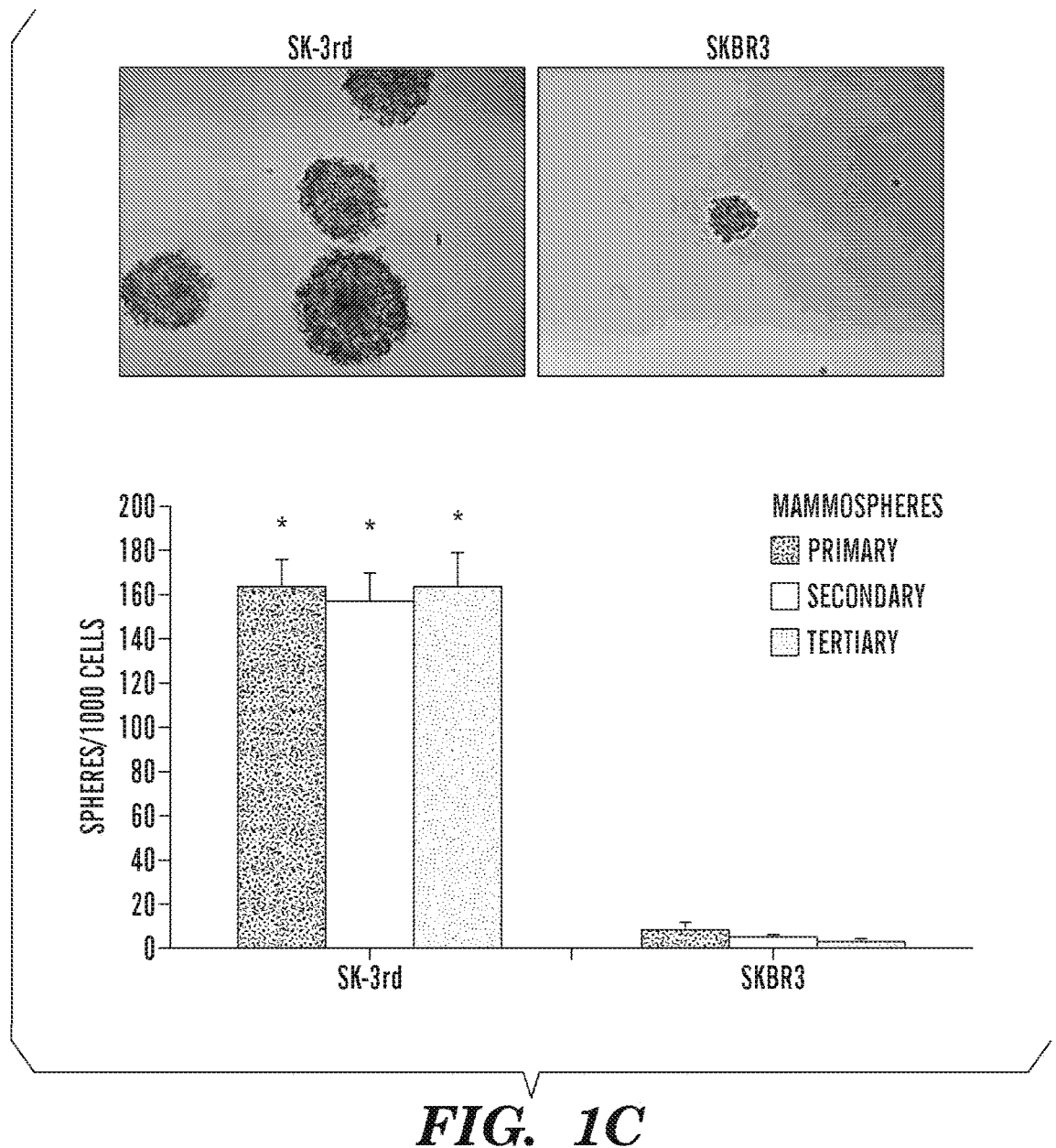
Figure 1D:
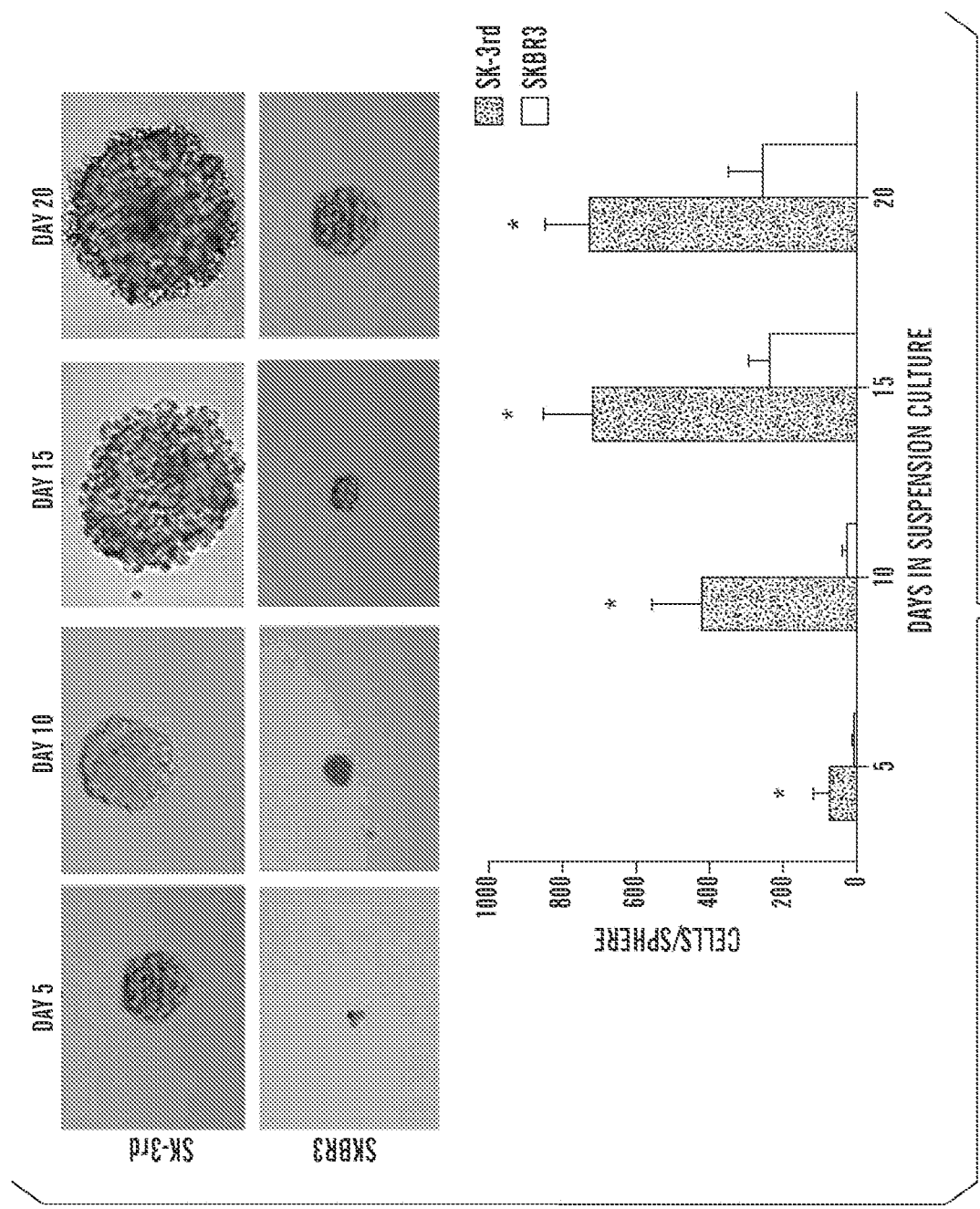
Figure 6:
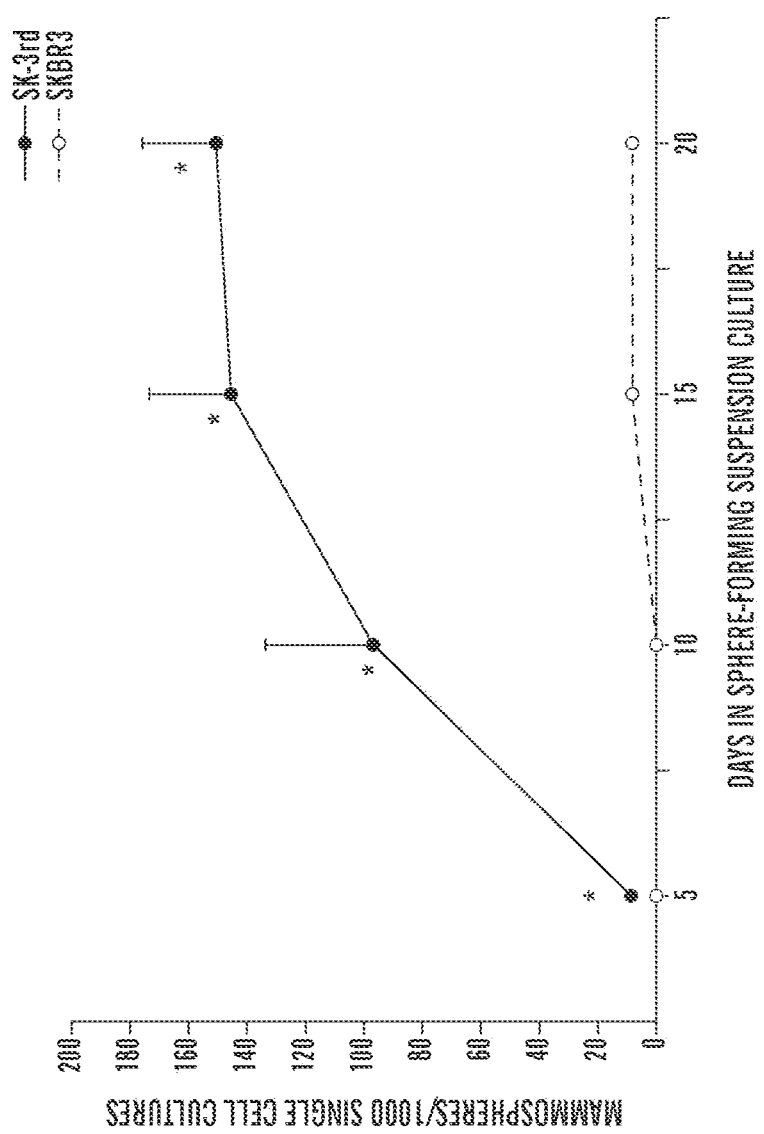
FIG. 6 shows that SK-3rd cells in single cell suspension cultures have enhanced capability to form mammospheres. Nonadherent mammospheres generated from single-cell suspension cultures of SK-3rd and SKBR3 cells were counted for 20 d of culture. *, P<0.001 SK-3rd compared with SKBR3 cells at the same time point.
Figure 8A:
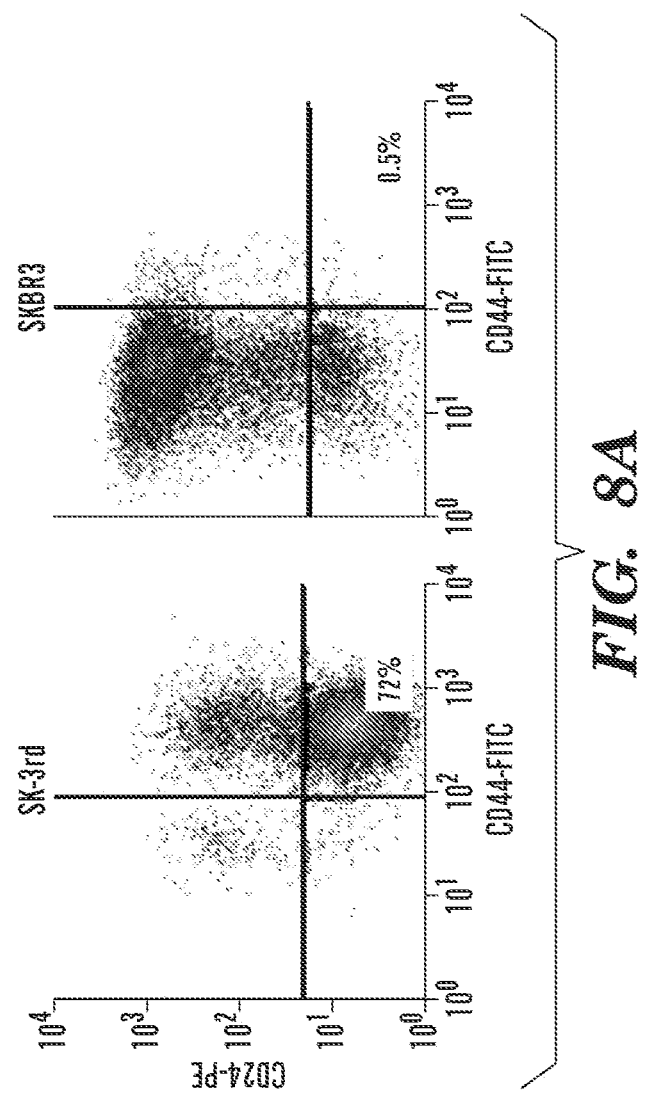
FIGS. 8A-C show that breast cancer cells under pressure of chemotherapy are enriched for tumor initiating breast cancer cells (BT-IC).
Figure 8B:
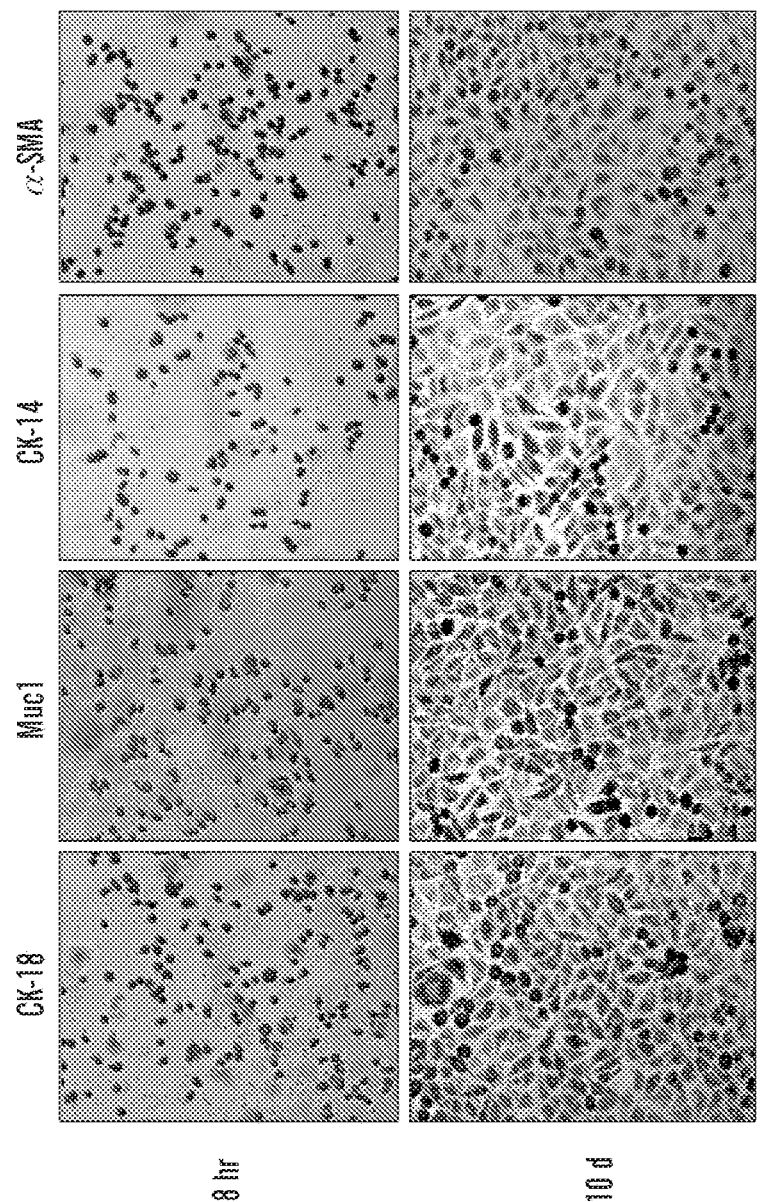
Figure 8C:
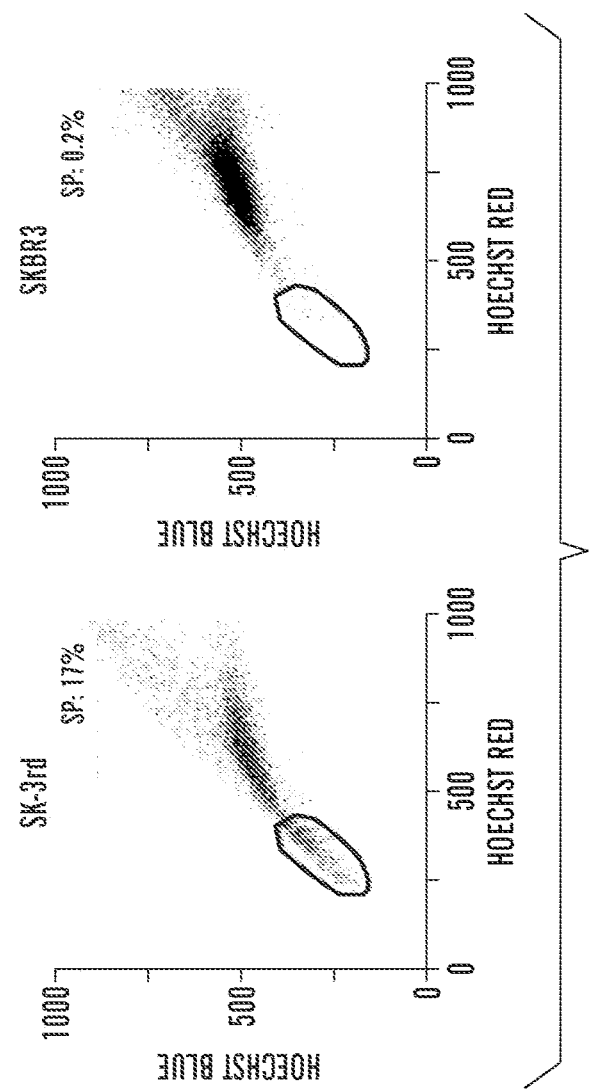
Figure 9A:
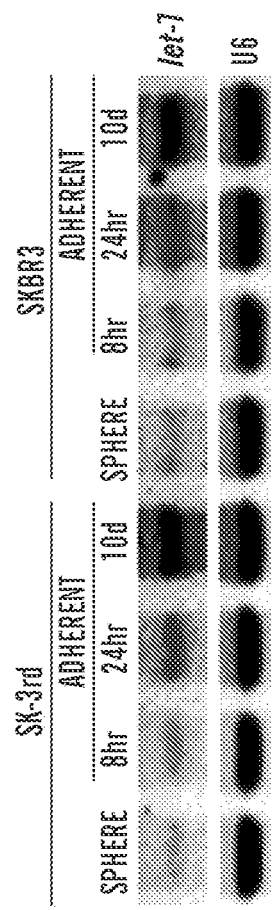
FIGS. 9A-9F show that let-7 miRNA is reduced in mamospheric SK-3$^{rd}$ cells in primary tumor initiating breast cancer cells (BT-IC).
Figure 9B:
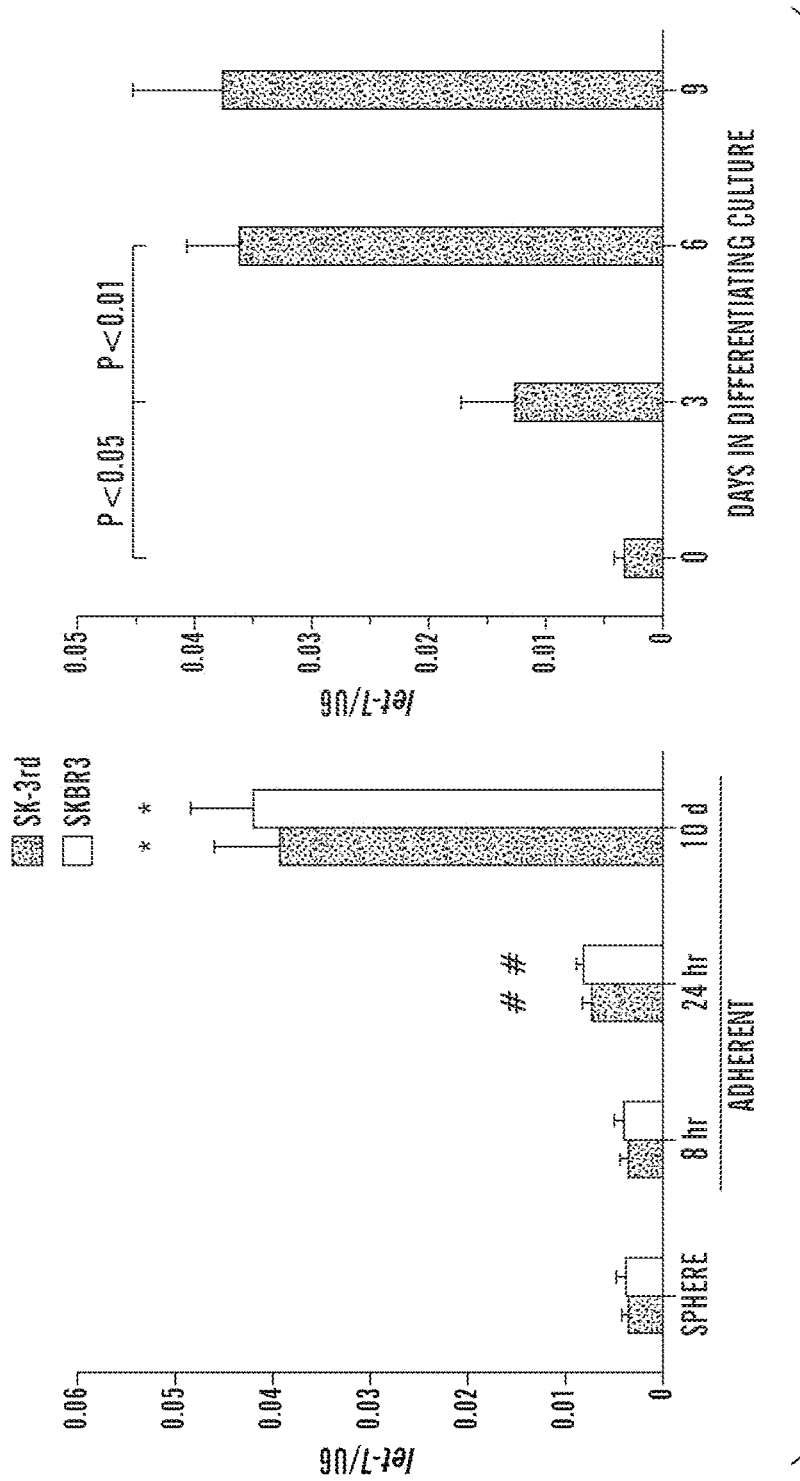
Figure 9C:
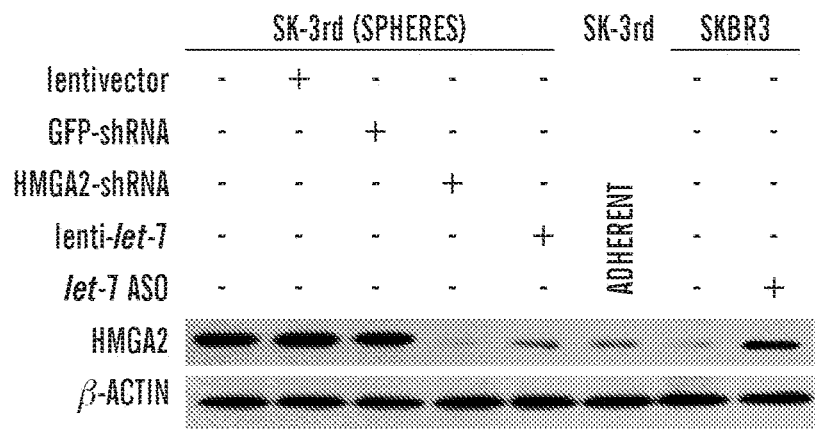
Figure 9D:
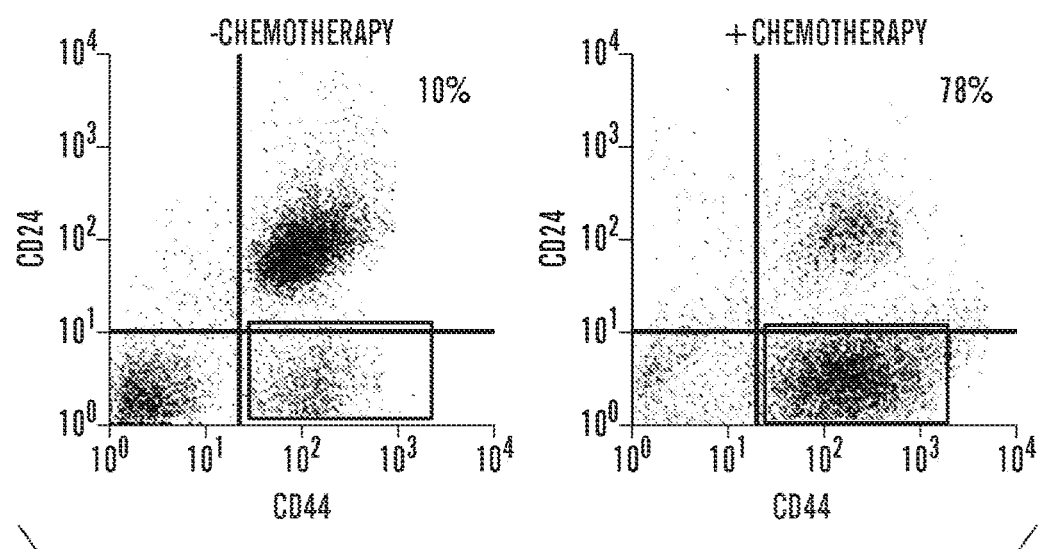
Figure 9E:
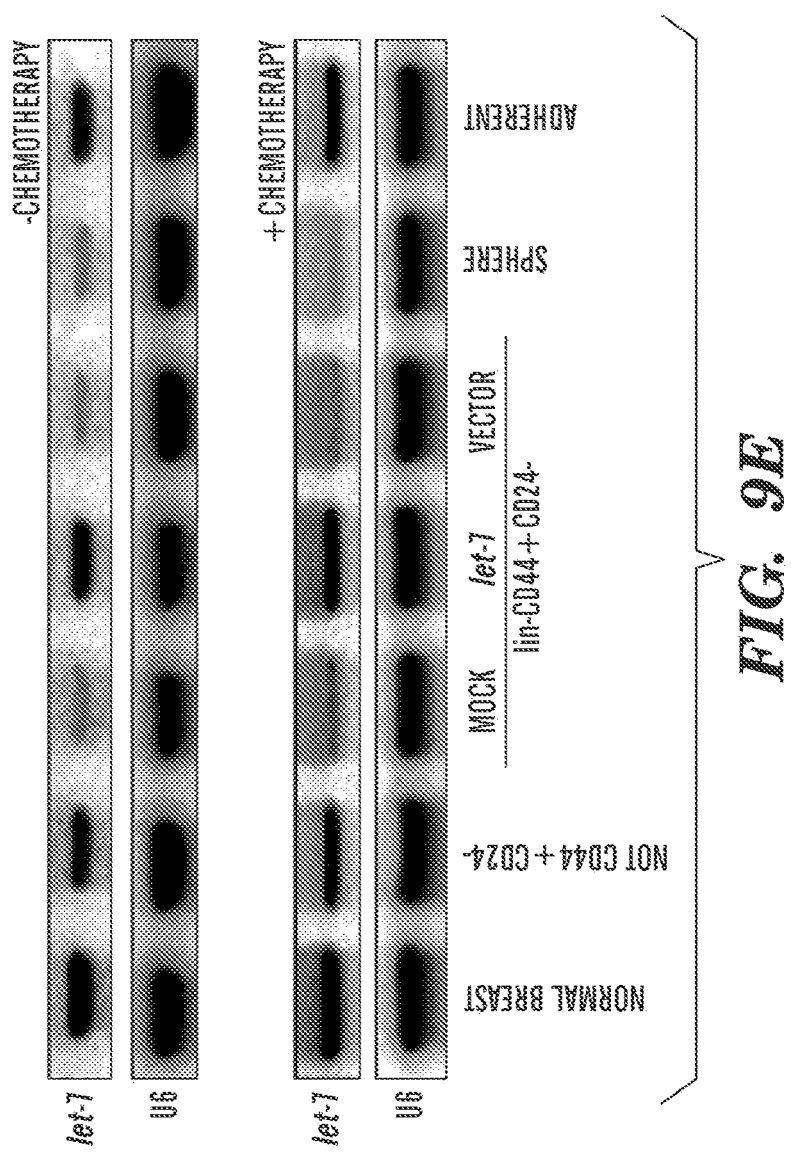
Figure 9F:
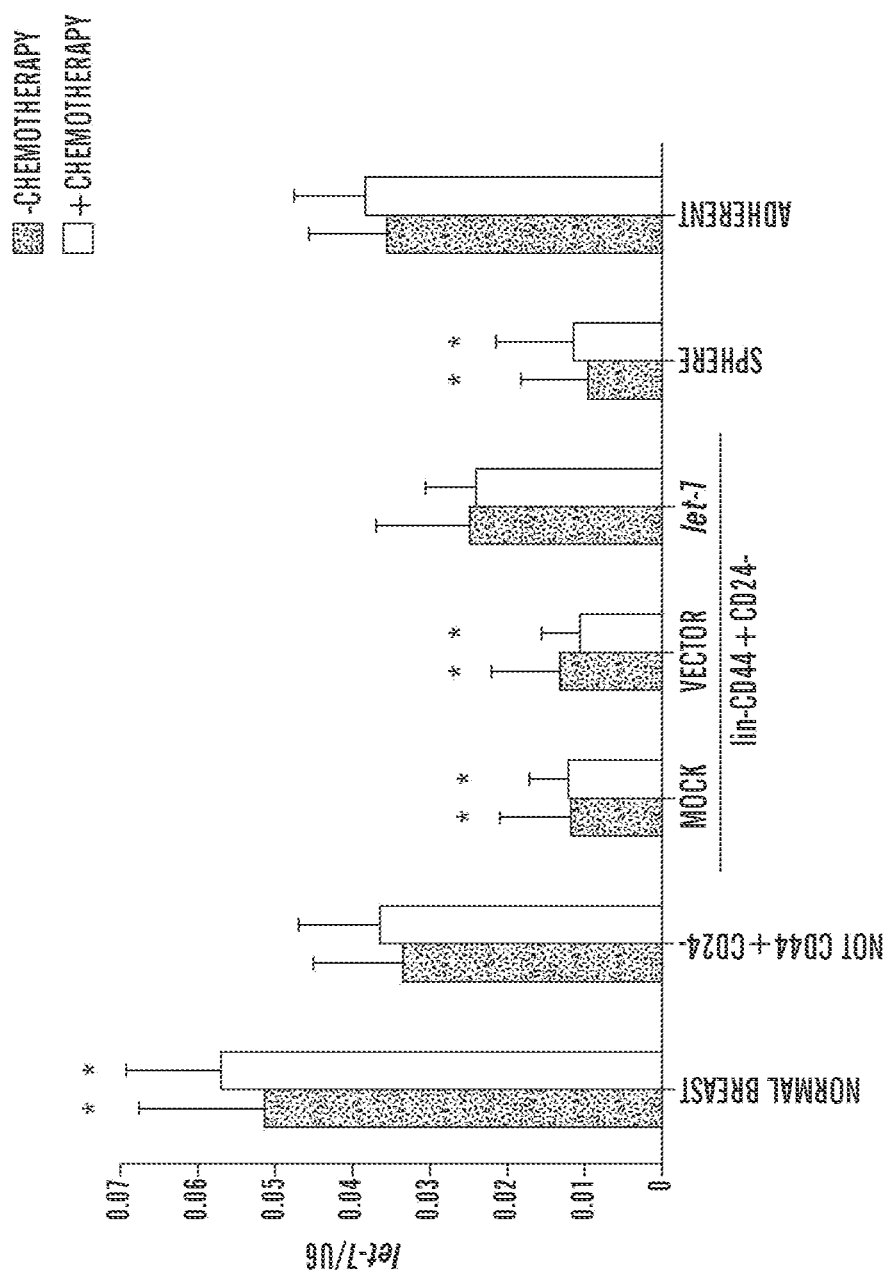
Figure 10A:
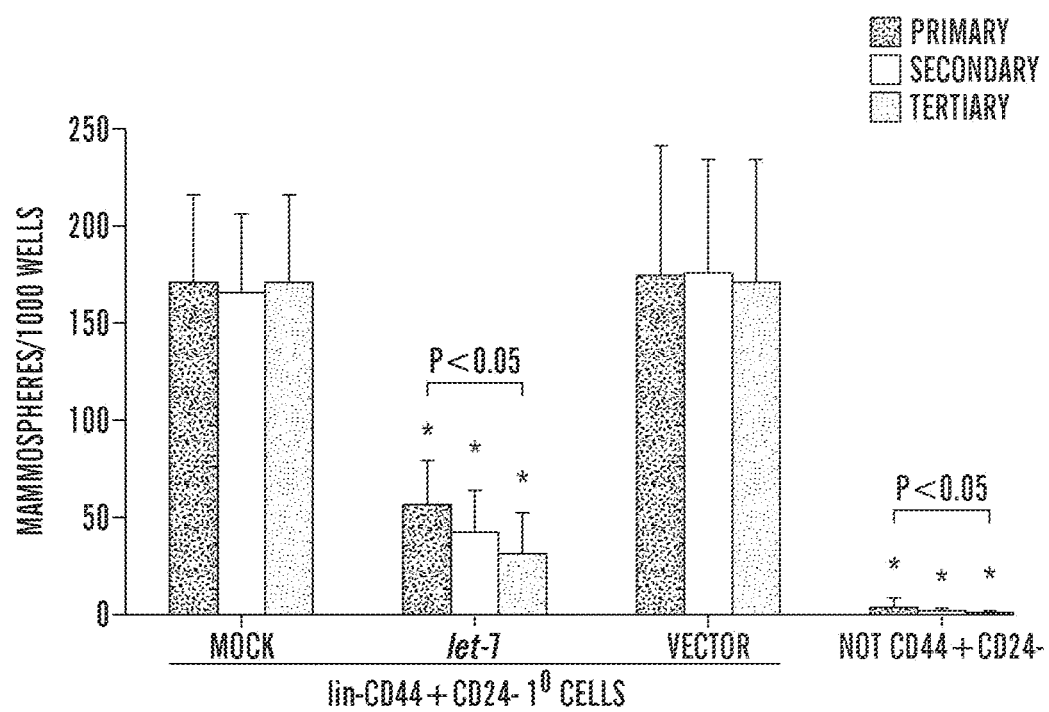
FIG. 10A-10D show that silencing HMGA2 reduces the undifferentiated subpopulation and proliferation of SK-3rd cells but does not significantly alter mammosphere formation.
Figure 10B:
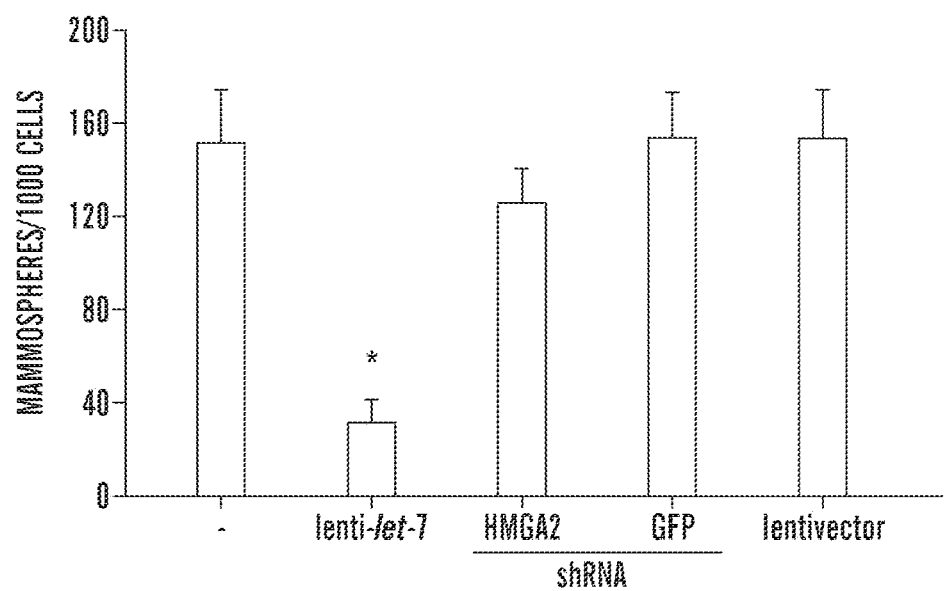
Figure 10C:
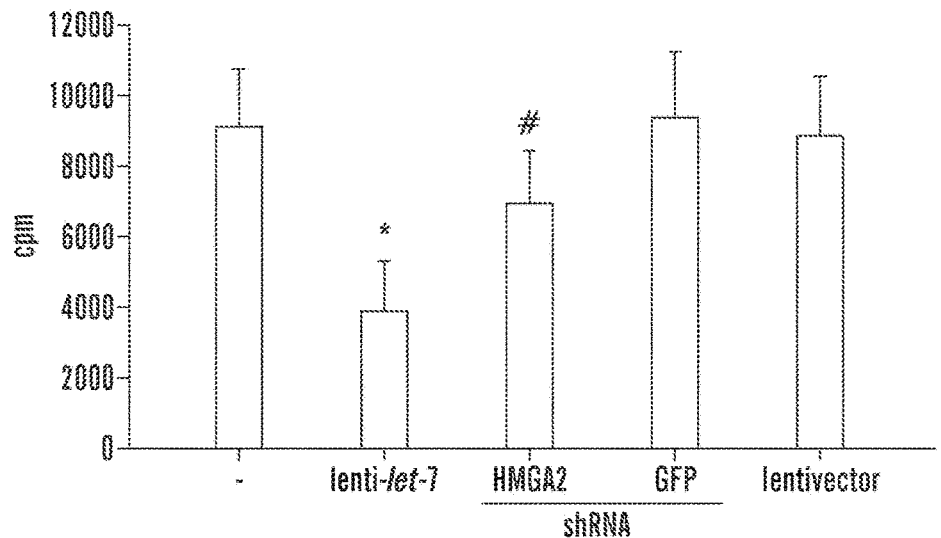
Figure 10D:
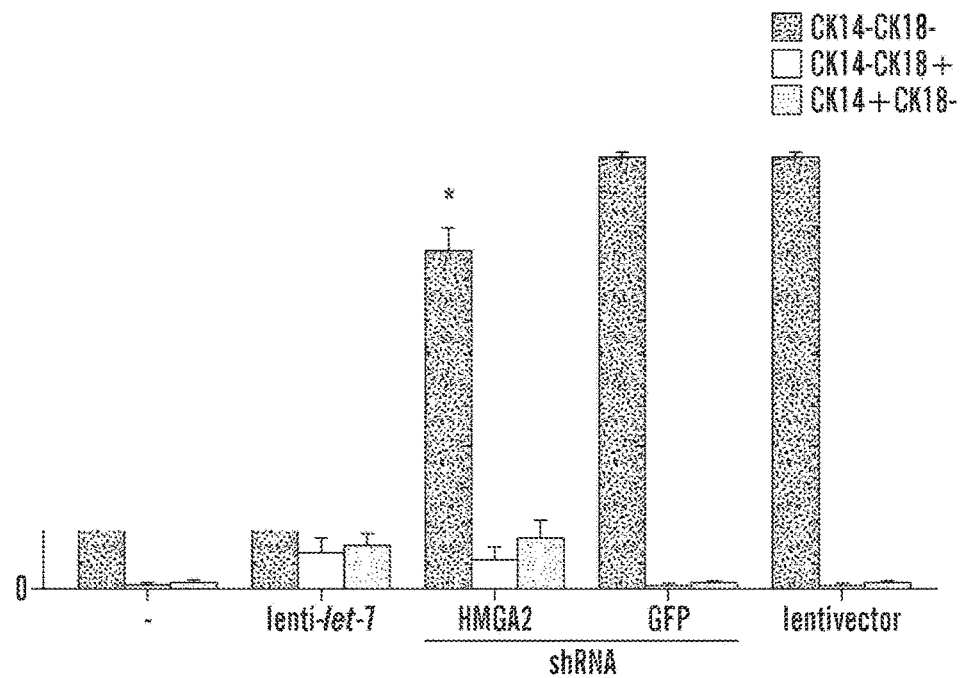

The inventors took advantage of this finding to demonstrate the ability to enrich for tumor-initiating cells by consecutively passaging breast cancer cells in NOD/SCID mice treated with low dose chemotherapy. Mice injected in the mammary fat pad with SKBR3 tumor cells were treated with Epirubicin weekly for 10-12 weeks until xenografts reached a diameter of ~2 cm. Cells from the $3^{rd}$ passaged xenograft (SK-3rd) were cultured in suspension to generate mammospheres. The number of mammospheres reflects the quantity of stem cells with self-renewal potential, while the number of cells per mammosphere measures the self-renewal capacity of each cell[25,26]. The inventors assessed the percentage of mammospheres formed by SK-3rd and their parental SKBR3 counterparts after 15 d in suspension culture. Mammosphere formation in SK-3rd was approximately 20-fold higher than SKBR3 (16.3% vs. 0.8%, P<0.001, FIG. 1c). Moreover, dissociated SK-3rd cells from primary mammospheres generated an equivalent proportion of secondary spheres and subsequently tertiary spheres (FIG. 1c), demonstrating their self-renewing potential in vitro. Long-term SK-3rd mammosphere cultures could be maintained for >50 passages, while within 3-4 passages, mammospheres from SKBR3 failed to generate secondary spheres and became adherent and differentiated. These findings were confirmed by single cell cloning (FIG. 6). SK-3rd mammospheres were observed beginning at day 5 and increased in size and cell number until day 15 (FIG. 1d). Secondary mammospheres could be passaged >40 times from single cell SK-$3^{rd}$ clones.

However, mammospheres did not appear until d 15 in parental SKBR3 cells and were about 18-fold fewer in number and much smaller (FIG. 1d).

Figure 1E:
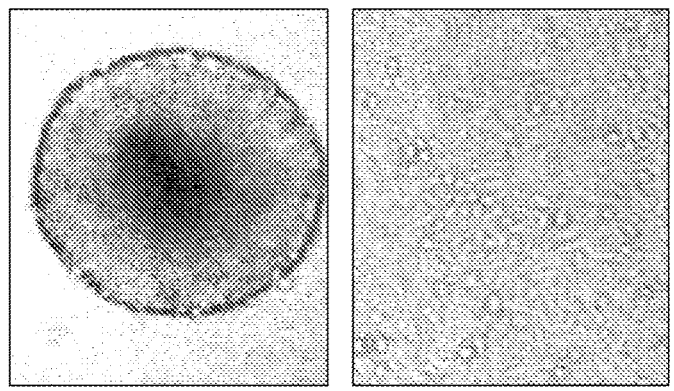
Figure 1F:
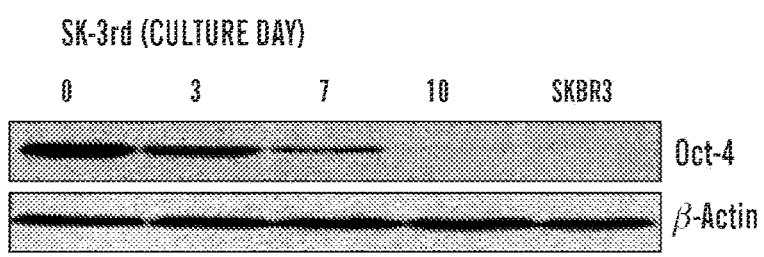
Figure 1G:
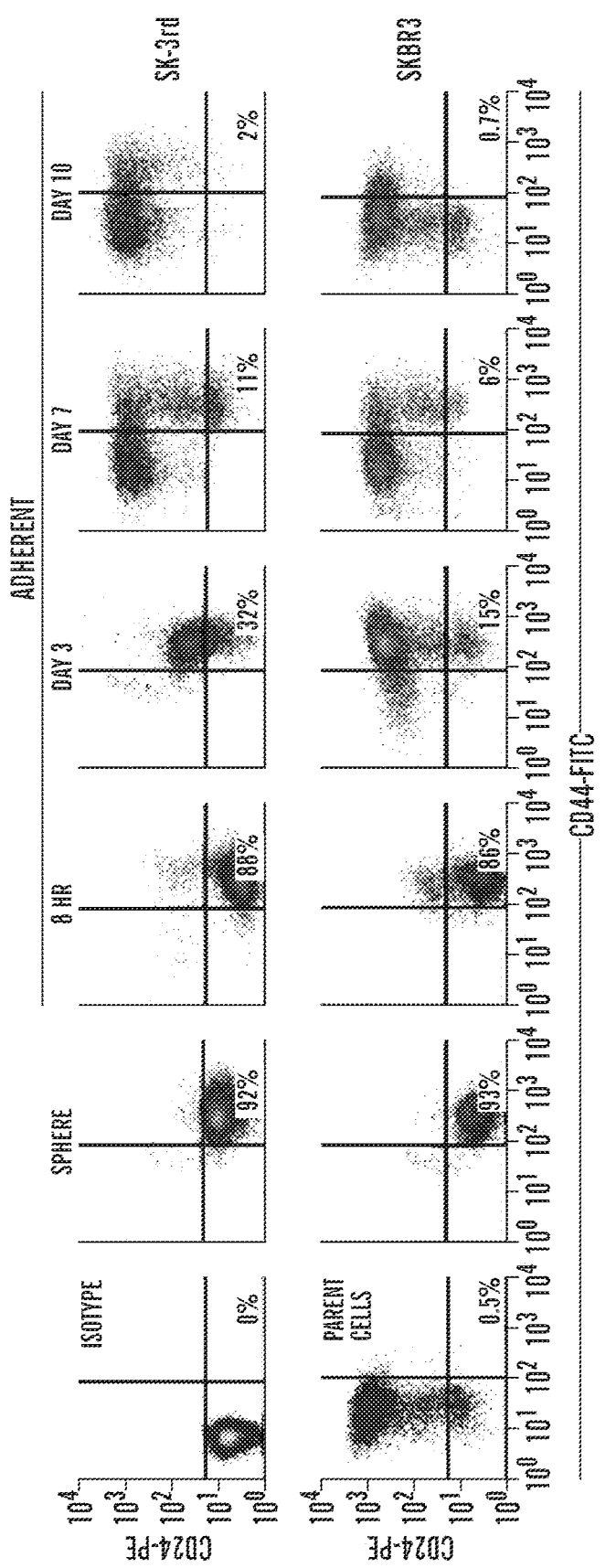

Dissociated SK-3rd mammospheres could be differentiated in vitro by plating on collagen in serum-containing medium lacking exogenous growth factors. Within 24 hr, the suspended cells began to adhere and spread and could thereafter be maintained and expanded as differentiated cells (FIG. 1e). Moreover, 93% of mammosphere-derived SK-3rd, but fewer than 0.5% of parental SKBR3, were CD44$^+$CD24$^-$, the phenotype of tumor-initiating breast cancer cells[9,10,15] (FIG. 1g). During in vitro differentiation of SK-3rd, the percentage of CD44$^+$CD24$^{-/low}$ cells decreased steadily to ~32% on d 3, 11% on d 7 and 2% on d 10. Furthermore, SK-3rd, but not SKBR3, cells highly expressed the stem cell-associated transcription factor Oct-4, which declined upon in vitro differentiation (FIG. 10. Therefore SK-3rd mammospheric cells have the self-renewing and differentiating capability and phenotypic properties expected of breast cancer stem cells.

Example 2

Breast Tumor-Initiating Cells have Reduced Expression of Let-7 miRNAs and Let-7 Homologues or Let-7 Mimetics.

Figure 2A:
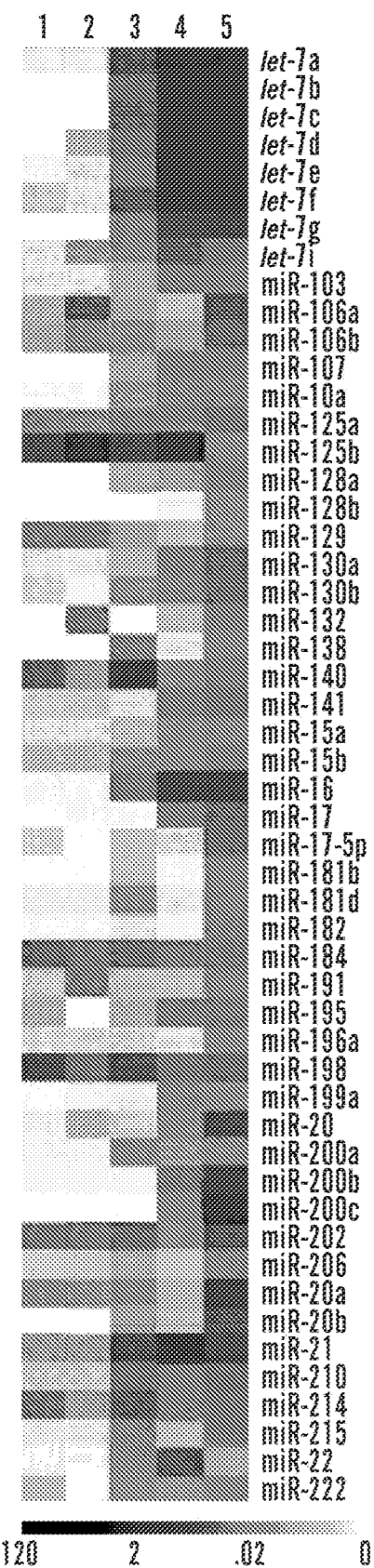
FIGS. 2A-2G show that SK-3rd cells and primary breast cancer cells from chemotherapy-treated patients have low expression of let-7 family miRNAs.
Figure 2B:
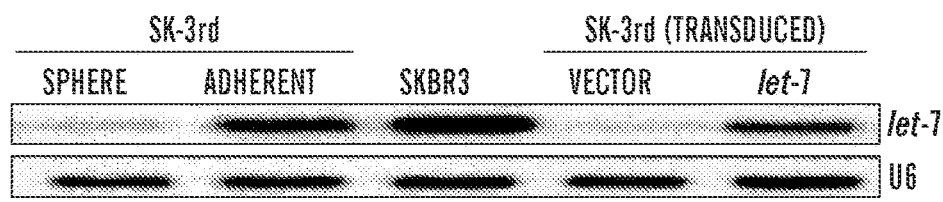
Figure 2C:
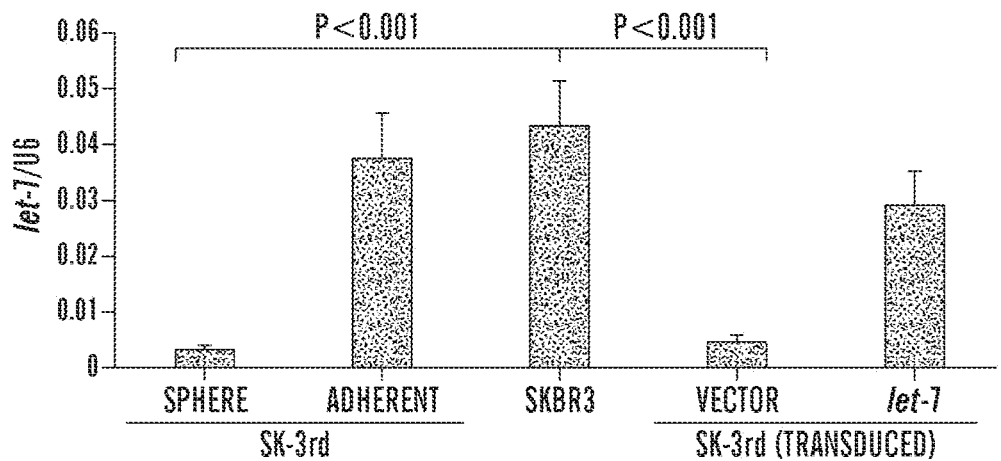

The inventors used miRNA microarrays to compare miRNA expression in mammosphere-derived SK-3rd with their in vitro differentiated progeny and the parental SKBR3 cells. As has been reported for ES cells[22,27], most of the 52 miRNAs that were reproducibly expressed above background in any of the 3 cell lines had reduced expression in SK-3rd compared with either the differentiated SK-3rd cells or SKBR3 (FIG. 2a). Cluster analysis of multiple samples showed a clear distinction between mammospheric cells and the other two adherent lines (data not shown). Using ANOVA analysis on the normalized chip data, we identified a number of human miRNAs whose expression in mammospheric cells was significantly different from the differentiated and parent cells. Among them, the let-7 family emerged as the most consistently and significantly reduced miRNAs. let-7 was initially identified as a miRNA that regulates development in C. elegans[28], where it was shown to target key genes include lin-41, hbl, daf-12, ha-4 and let-60 (a RAS homolog)[29-31]. In humans, 11 homologues of let-7 miRNAs exists, which are differentially expressed in different tissues, but are believed to have redundant targets and functions[29,32]. Human let-7, which is down-regulated in some cancers and associated with poor prognosis in lung cancer[33], targets the RAS oncogene and thereby acts as a tumor suppressor[31]. To verify the reduction of let-7 miRNAs in SK-3rd, the inventors performed Northern blot using a probe that recognizes a variety of let-7 family members or homologues[31] (FIG. 2b). let-7 was barely detected in SK-3rd, but increased with differentiation and was abundant in the parent SKBR3 cells. This result was verified using a let-7a-specific primer for quantitative reverse transcription-PCR (qRT-PCR). let-7a was 10-fold lower in SK-3rd than differentiated SK-3rd, and the level in the differentiated cells was comparable to SKBR3 (FIG. 2c).

Example 3

Let-7 Activity is Low in Breast Cancer Stem Cells and Increases During Differentiation.

Figure 2D:
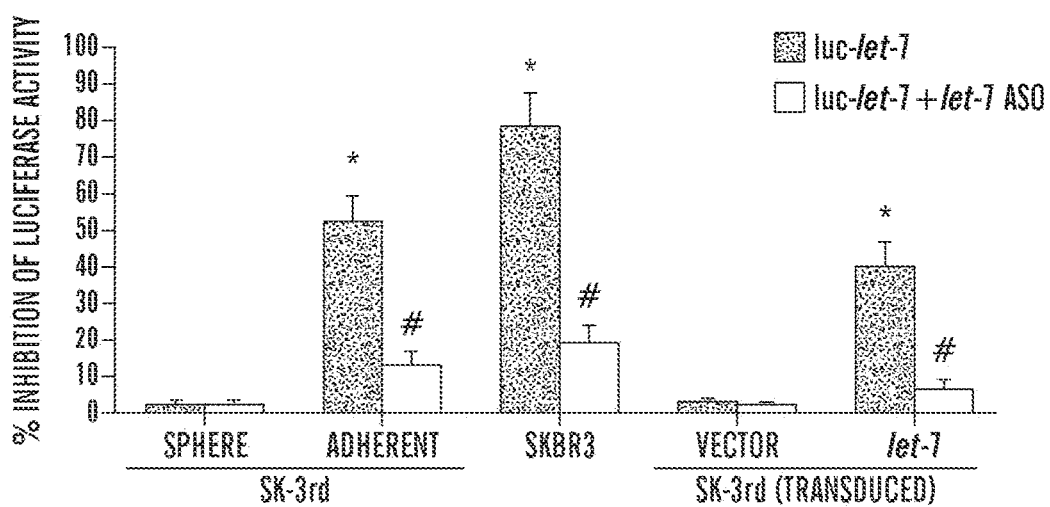

To investigate let-7 function, the inventors transfected a luciferase reporter vector containing a let-7 target sequence in its 3'UTR into SK-3rd, differentiated SK-3rd and SKBR3. Luciferase activity was suppressed by 52% in differentiated SK-3rd cells (P<0.001) and by 78% in SKBR3 (P<0.001), while there was no suppression in SK-3rd (FIG. 2d). Infection of SK-3rd with a lentivirus expressing let-7a pre-miRNA enhanced miRNA expression and function comparably to that of the differentiated progeny cells (FIG. 2b-d). Co-transfection of differentiated SK-3rd cells, SKBR3 or let-7a lentivirus-infected SK-3rd with a let-7 antisense oligonucleotide (ASO) significantly reduced the suppression in luciferase activity mediated by endogenous or exogenous let-7 (P<0.01; FIG. 2d).

Figure 2E:
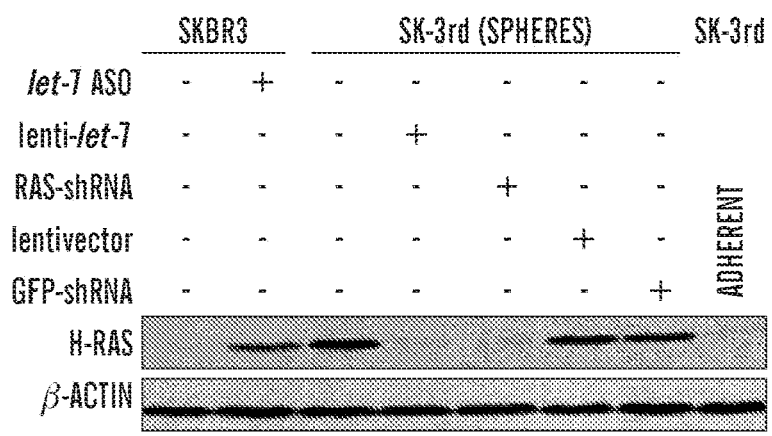

Since RAS is a major target of let-7 miRNAs[31], the inventors next compared HRAS1 mRNA and protein expression in the 3 cell lines. H-RAS protein was highly expressed in SK-3rd stem cells, but was greatly reduced in differentiated SK-3rd cells and SKBR3. (Other RAS proteins were not detected in any of these cells (data not shown). As expected, introduction of let-7a or RAS-shRNA by lentiviruses into SK-3rd reduced H-RAS protein to the level found in the differentiated cells, while inhibiting let-7 with a specific ASO in the parent SKBR3 cells up-regulated H-RAS expression substantially (FIG. 2e). However, HRAS1 mRNA, measured by qRT-PCR, did not differ significantly amongst the 3 sources of cells (data not shown). Therefore, let-7 silences RAS expression by inhibiting translation, and reduced let-7 in breast cancer stem cells leads to RAS over-expression.

Example 4

Let-7 is Reduced in Breast Tumor-Initiating Cells from Primary Cancers.

Figure 2F:
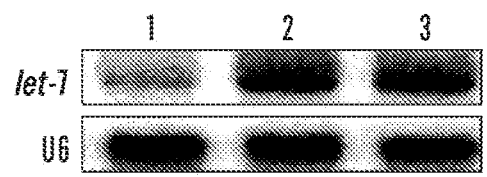
Figure 2G:
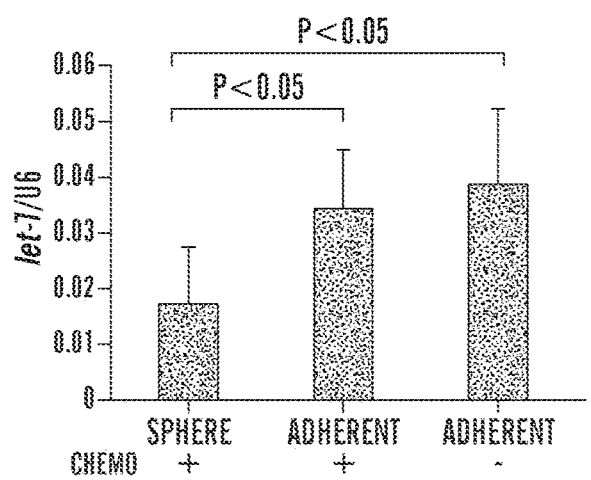

To confirm that the results with the breast cancer cell line are physiologically relevant to primary breast cancers, the inventors examined let-7 family expression in the breast tumor-initiating cells from primary cancers by Northern blot and quantified it by qRT-PCR using a let-7a-specific primer (FIG. 2f,g). In agreement with the data from SK-3rd cells, the tumor-initiating cells from primary mammospheres from primary cancers from chemotherapy-treated patients had reduced let-7 (Fog 20, for example at least about, 20%, or at least about 30% or at least about 50% lower level, as compared with the primary cancer cells freshly isolated from tissue samples of untreated patients. When the tumor-initiating mammospheric cells were differentiated for 14 d in adherent cultures, let-7 expression returned to the level in untreated-patient cells.

Example 5

Reduced Let-7 is Required to Maintain Self-Renewal of Tumor-Initiating Cells.

Figure 3A:
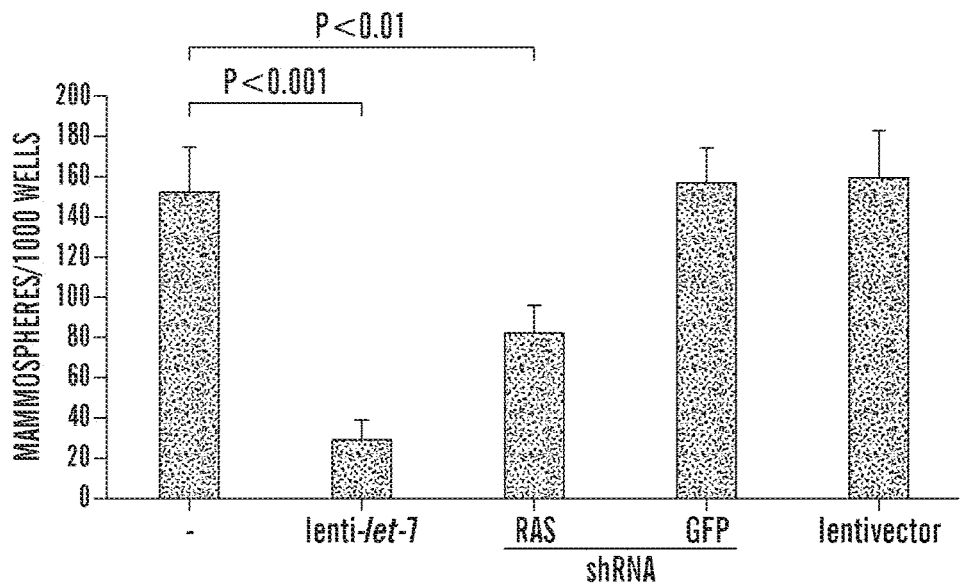
FIGS. 3A-3F shows that SK-3rd cells engineered to express let-7a lose "stemness".
Figure 3B:
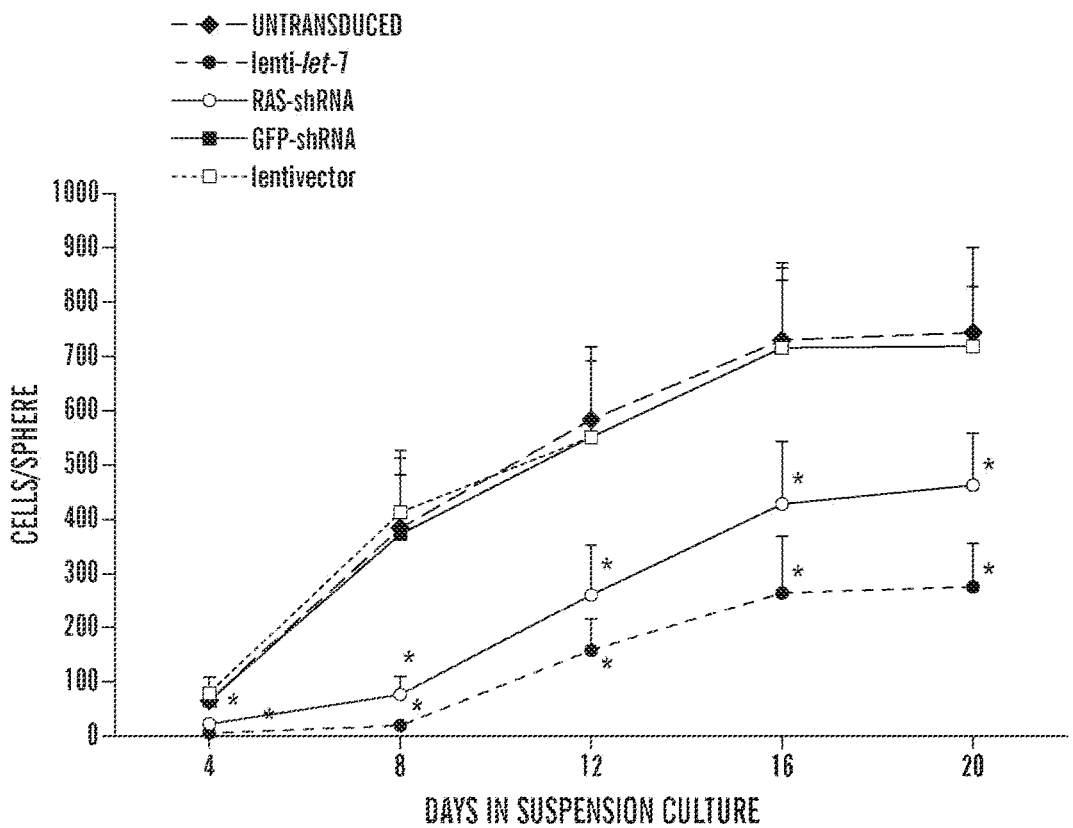
Figure 3C:
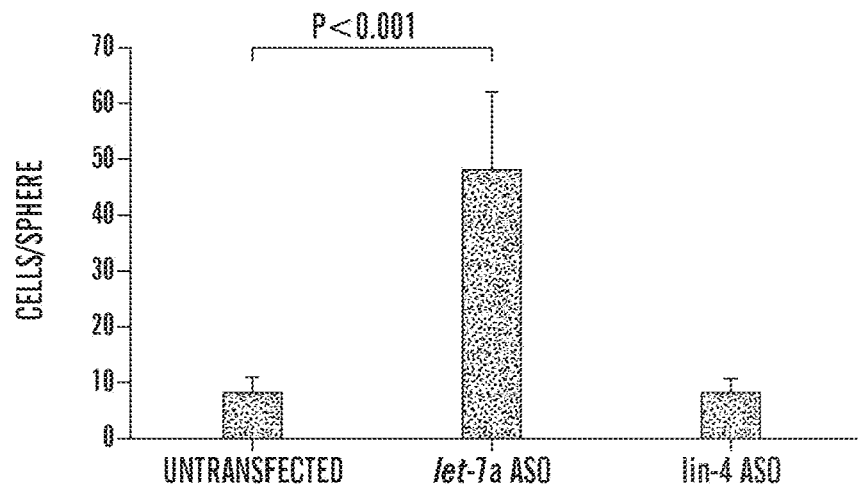

To test the importance of low let-7 expression in breast cancer stem cells, the inventors first studied the effect of enforced let-7a expression in SK-3rd on self-renewal using the mammosphere-forming assay. As disclosed above, the ability of a cell to form a mammosphere (i.e. an embryoid body) indicates the self-renewal capacity of the cell. SK-3rd cells infected with let-7a lentivirus formed 5.3-fold fewer secondary mammospheres than uninfected SK-3rd or SK-3rd cells infected with lentiviral vectors that were empty or expressed an eGFP-shRNA (FIG. 3a). Mammosphere formation was also delayed and the mammospheres that formed were 2-3-fold smaller in let-7a-expressing SK-3rd cells compared with control SK-3rd cells (FIG. 3b). Importantly, the let-7a-transduced mammospheric cells could only be passaged for 8-10 generations. Therefore let-7a transduction not only reduced the number of tumor-initiating cells, but also weakened their self-renewing capacity. Conversely, transfecting let-7 ASO into parental SKBR3 cells enhanced their ability to form mammospheres by ~6-fold (FIG. 3c).

Example 6

Reduced Let-7 Maintains Tumor-Initiating Cell Proliferation, but Inhibits their Differentiation.

Figure 3D:
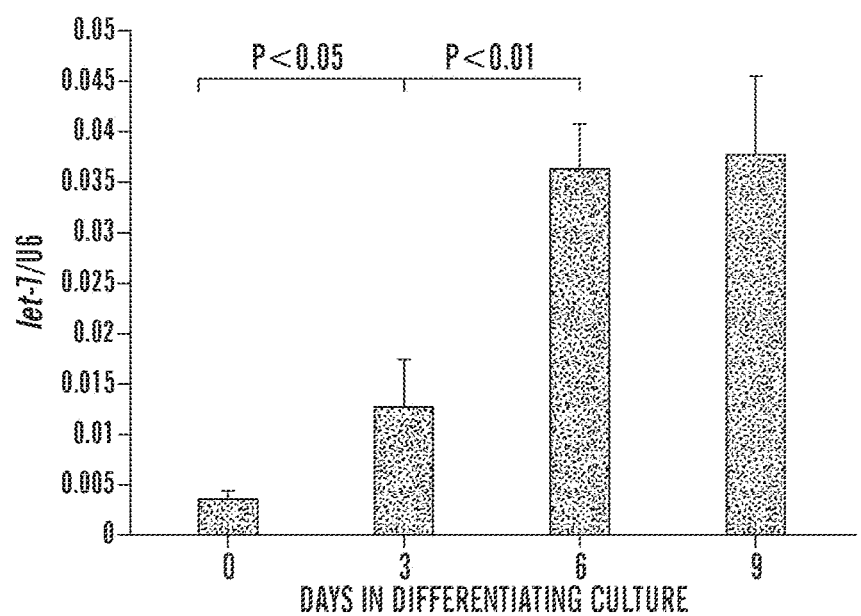
Figure 3E:
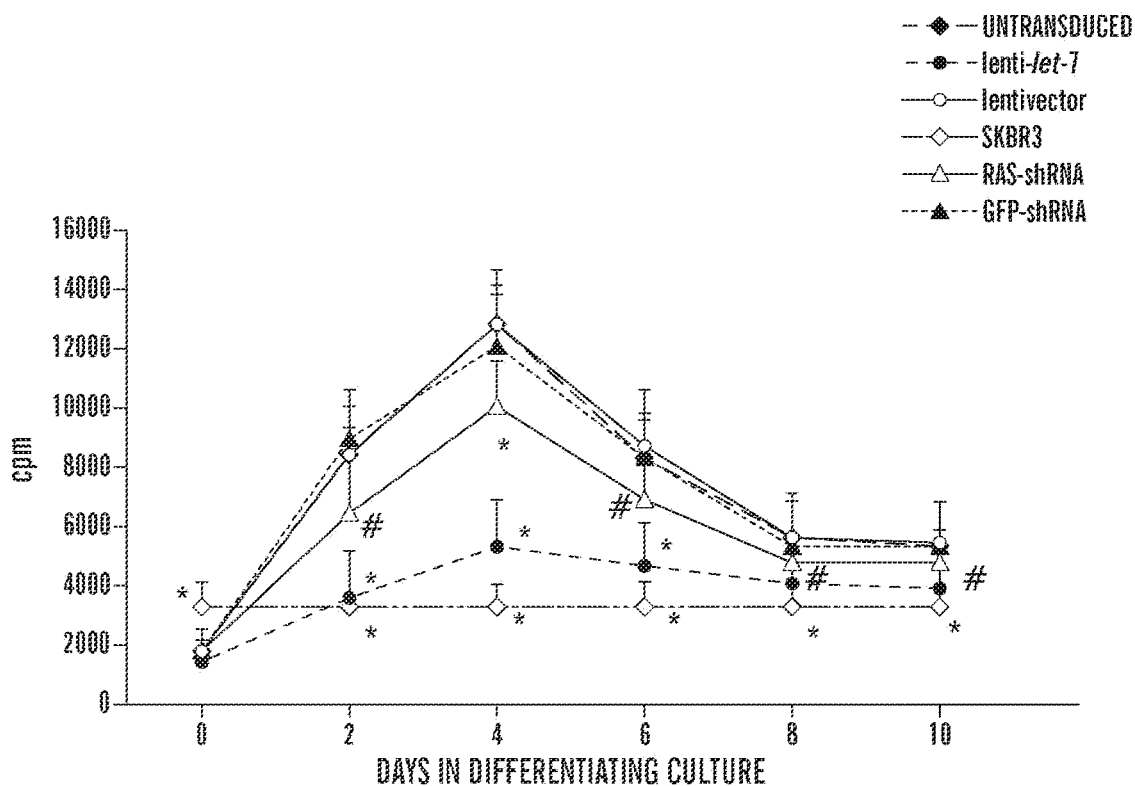
Figure 3F:
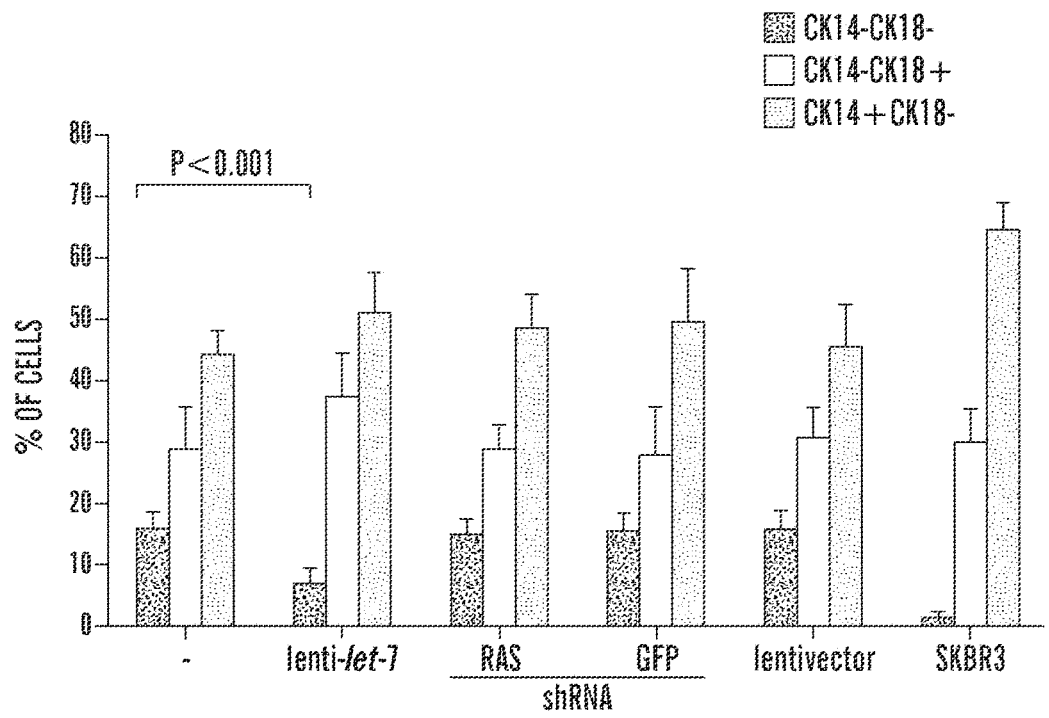

Another important stem cell property is the potential to proliferate during differentiation. When mammospheric SK-3rd cells were plated for differentiation, let-7 expression measured by qRT-PCR, increased gradually and plateaued on d 6 (FIG. 3d). Resting SK-3rd cells proliferated at half the rate of parental SBR3 cells as measured by [$^3$H] incorporation (FIG. 3e). During differentiation, SK-3rd proliferation increased about 7-fold from baseline to a peak on d 4 and then fell by d 8 to a level somewhat higher than that of the parental cell line (P<0.01). To investigate the effect of let-7 on proliferation, the inventors measured proliferation during differentiation of SK-3rd cells transduced with pre-let-7a. Enhancing let-7a expression reduced peak [$^3$H]-incorporation by 58%, demonstrating that reduced let-7 enhances the proliferative potential of differentiating stem cells.

Another hallmark of stem cells is their undifferentiated state and potential to differentiate into multiple lineages. Mammospheric SK-3rd cells expressed neither myoepithelial (CK14) nor luminal epithelial (CK18) cytokeratins (data not shown), while the parental SKBR3 cells were 70% myoepithelial and 30% luminal epithelial (FIG. 30. However, after 10 days of differentiation, most of the SK-3rd cells expressed differentiation markers (44±4% CK14+ CK18−, 28±7% CK14−CK18+), but 15±3% were lin⁻. let-7a over-expression significantly (P<0.001) reduced the proportion of lin⁻ cells to 6±2%, but control lentiviruses, including a lentivirus expressing RAS-shRNA (see below), had no effect on in vitro differentiation. Taken together, these data demonstrate that low let-7 expression helps to maintain the undifferentiated status and proliferative potential of breast tumor-initiating cells.

Example 7

Let-7 Expression Silences RAS and Other Genes: Silencing RAS Only Partly Recapitulates the Effects of Let-7 Expression.

Since RAS is a well-documented target of let-7[31], the inventors investigated whether the effects of reduced let-7 in maintaining tumor-initiating properties of SK-3$^{rd}$ could be attributed to RAS oncogene expression. A lentivirus expressing RAS-shRNA reduced H-RAS protein in SK-3rd to the level in SKBR3 or differentiated SK-3rd and comparably to that of the let-7a-lentivirus (FIG. 2e). SK-3rd cells with silenced H-RAS formed mammospheres at a level that was about half that of untransduced or control vector transduced SK-3$^{rd}$ cells, but about 3-fold greater than cells transfected with let-7a-lentivirus (FIG. 3a); moreover the mammospheres that formed were intermediary in size (465±94 cells vs. 745±155 cells for untransduced SK-3rd and 277±82 cells for let-7a-transduced SK-3rd on d 20; FIG. 3b). Silencing RAS also somewhat reduced SK-3$^{rd}$ proliferation under differentiating conditions, but much less than expressing let-7a (FIG. 3e, P<0.001, on d 4 of differentiation, the peak of proliferation). As noted above, silencing RAS, unlike over-expressing let-7a, in SK-3rd did not reduce the residual proportion of undifferentiated cells lacking cytokeratin expression after in vitro differentiation (FIG. 30. Therefore, let-7 silencing of RAS explains some, but not all, of the role of let-7 in converting breast cancer stem cells to more differentiated progeny. These data demonstrate that expression of let-7 targets other RNA transcripts in addition to RAS in breast cancer stem cells which contribute to the "stemness" or self-renewal capacity of cancer stem cells, such as breast cancer stem cells.

Example 8

Lack of Let-7 Facilitates Tumorigenesis of Breast Tumor-Initiating Cells.

Figure 4A:
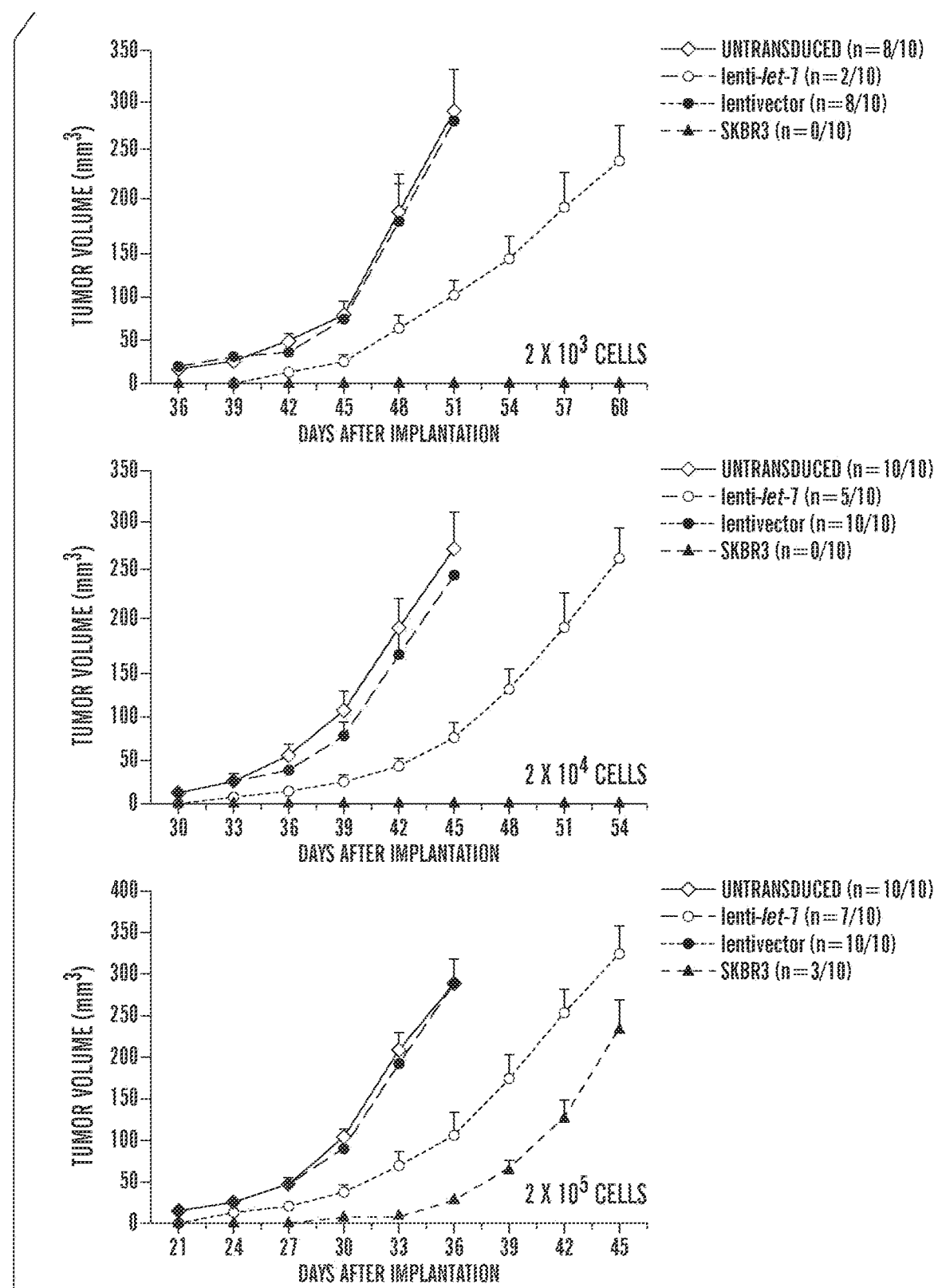
FIGS. 4A-4D shows that expression of pre-let-7a by SK-3rd cells suppresses tumor xenograft growth in NOD/SCID mice.

Cancer stem cells establish tumor xenografts much more readily than differentiated tumor cells[1,2]. When mammospheric SK-3rd cells were inoculated subcutaneously into NOD/SCID mice, eight of ten mice engrafted with 2×10$^3$ cells generated tumors that were first detected 36-45 d later (Table 1, FIG. 4a). All animals injected with 10 or 100-fold more cells developed tumors within 30 and 21 days, respectively. Within 14 days after tumors were identified, their sizes reached 1.8±0.7 cm in diameter. By contrast, no mice inoculated with 2×10$^3$ or 2×10$^4$ SKBR3 cells developed tumors by day 60, while tumors developed by day 45 in only 3 of 10 animals inoculated with 2×10$^5$ SKBR3 cells. Therefore, SK-3rd cells are at least 100-fold more tumorigenic than the parental cell line. When let-7a expression was enforced in mammospheric SK-3rd cells, tumors developed in only 20%, 50% and 70% of mice inoculated with 2×10$^3$, 2×10$^4$ and 2×10$^5$ cells, respectively. Moreover, the let-7a-expressing tumors grew more slowly than the untransduced or control vector-transduced SK-3rd tumors; it took 25-33 days for the tumors after they became palpable to reach 2.0 cm in diameter, while the control SK-3rd cells reached that size in ~12 d (FIG. 4a).

TABLE 1

Incidence of tumors and metastasis in mammospheric SK-3$^{rd}$ cells and SKBR3 cells in NOD/SCID mice.
\* = p < 0.05; ∞ = p < 0.01, # = p < 0.001 compared with untransduced mammospheric SK-3$^{rd}$ cells.

| | | 1 × 10$^3$ | | | 1 × 10$^4$ | | | 1 × 10$^5$ | | |
|---|---|---|---|---|---|---|---|---|---|---|
| Number of cells inoculated | | Tumors | Lung metastasis | Liver metastasis | Tumors | Lung metastasis | Liver metastasis | Tumors | Lung metastasis | Liver metastasis |
| Mammo-spheric SK-3rd cells | Untransduced | 8/10 | 6/10 | 3/10 | 10/10 | 7/10 | 4/10 | 10/10 | 8/10 | 6/10 |
| | Lentivirus | 8/10 | 5/10 | 3/10 | 10/10 | 8/10 | 5/10 | 10/10 | 8/10 | 5/10 |
| | Lenti-let-7 | 2/10* | 1/10 | 0/10 | 5/10* | 3/10 | 1/10 | 7/10 | 4/10 | 3/10 |
| | RAS-shRNA | 3/10* | 2/10 | 1/10 | 7/10 | 5/10 | 3/10 | 10/10 | 7/10 | 4/10 |
| SKBR3 | | 0/10∞ | 0/10* | 0/10 | 0/10# | 0/10∞ | 0/10 | 3/10 | 0/10 | 0/10 |

Furthermore, primary mammospheres from chemotherapy patients could be passaged for at least eight to ten generations (endpoint of the study), while those from patients without chemotherapy vanished within two to three generations. In the primary breast cancers; 74%±7% of tumor cells from chemotherapy-treated patients, but only 9%±4% of cells from untreated patients, were $CD44^+CD24^-$/low, the phenotype ascribed to BT-IC (Al-Hajj et al., 2003; Ponti et al., 2005) (p<0.001, FIG. 1B). Enrichment of BT-IC by chemotherapy was confirmed by studying paired specimens from seven patients obtained by biopsy prior to chemotherapy and at surgery following neoadjuvant chemotherapy. Only 0.5%±0.3% of tumor cells before chemotherapy, but 5.9%±1.7% of cells obtained after chemotherapy, formed mammospheres after 15 days of suspension culture (p<0.001, data not shown).

Figure 5A:
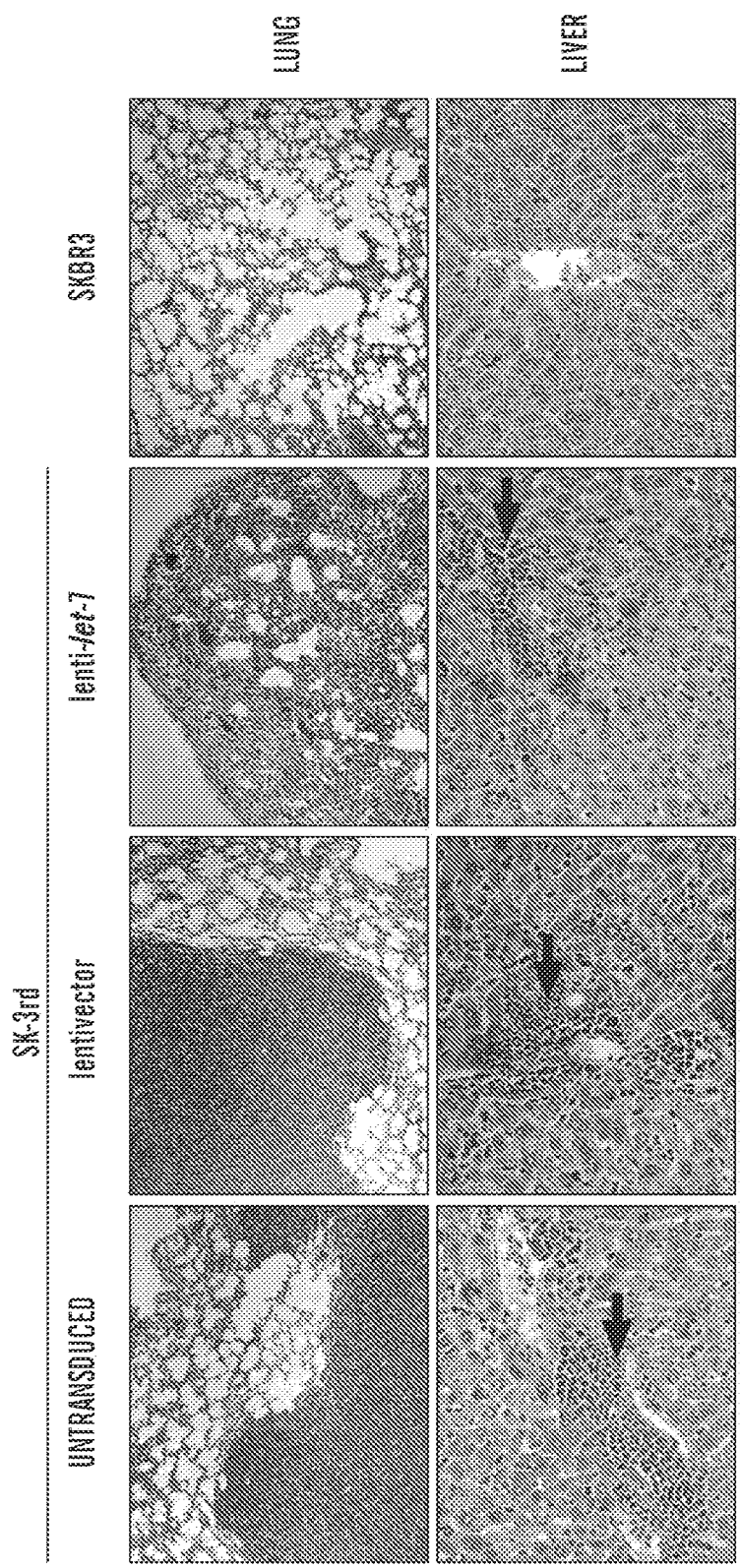
FIGS. 5A-5C show that SK-3rd cells transduced with pre-let-7a are less likely to metastasize.
Figure 5B:
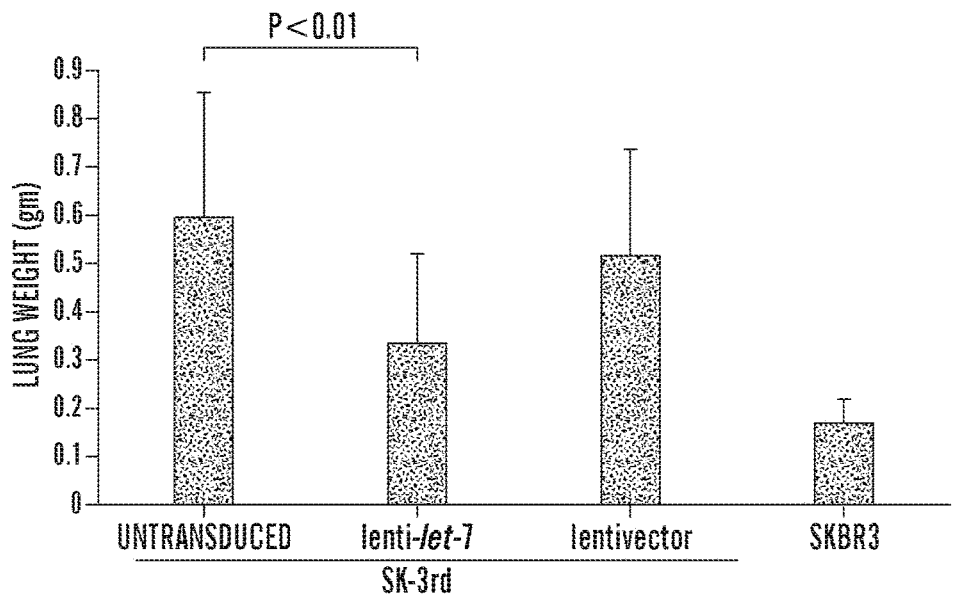
Figure 5C:
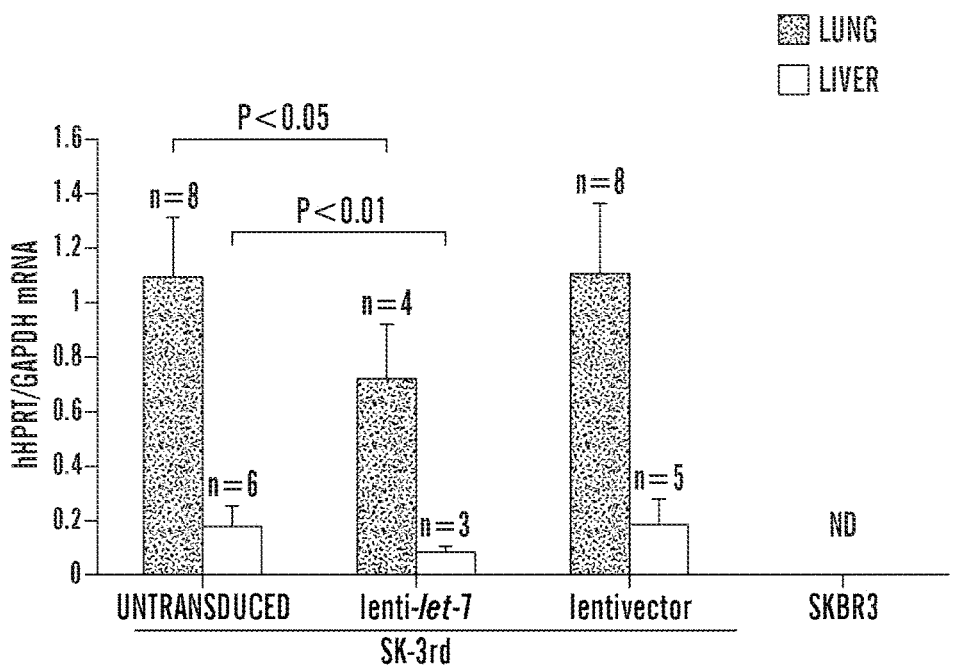

Similarly, the proportion of $CD44^+CD24^-$/low cells was 9.5-fold higher in samples after chemotherapy (p<0.001, Table 2). In another patient group with metastatic pleural effusions who had received chemotherapy 2-6 years before, pleural cancer cells were highly enriched (31%±10%) for $CD44^+CD24^-$/low cells (data not shown). These data from three cohorts suggest that chemotherapy selectively enhances the proportionate survival of BT-IC.

ness"[14,15,34]. The inventors compared lung and liver metastases of the xenografts generated from SK-3rd cells, expressing let-7a or not, and SKBR3 cells. Five weeks after inoculation with $2\times10^5$ mammospheric SK-3rd cells, massive lung metastases were visualized by microscopy in 8 of 10 mice, but none of the mice injected with the same number of SKBR3 cells developed microscopic lung metastases within 9 weeks of inoculation (FIG. 5a). As an indicator of metastases, the wet lung weight of mice engrafted with SK-3rd was significantly higher (~3-fold) than those injected with parental cells (P<0.01; FIG. 5b). Transduction of SK-3rd with lenti-let-7 reduced both the numbers of mice with lung metastases from 8 to 5 of 10 animals and the average lung weight by 44% (P<0.01). The metastases were not only smaller, but also dispersed among alveoli (FIG. 5a), suggesting reduced clinical severity. The number of tumor cells in the lung, quantified by qRT-PCR for human HPRT, was also 30% less in the animals injected with let-7a-expressing SK-3rd compared with those inoculated with cells transduced with the empty vector (P<0.05; FIG. 5c).

Similarly, mammospheric SK-3rd cells developed micrometastases in the livers of 6 of 10 mice inoculated with $2\times10^5$ cells, but SKBR3 cells did not (Table 1, FIG. 5a).

TABLE 2

Incidence of tumors from primary breast cancer cells serially transplanted in NOD/SCID mice.
* = p <0.05; $\infty$ = p < 0.01, # = p < 0.001 compared with untransduced lin$^-$CD44$^+$CD24$^{-/low}$ cells.
For the initial inoculation, each mouse was inoculated with sorted cells, transduced or nor, from a different chemotherapy naïve human patient. For subsequent passages, cells were isolated, sorted, and transduced forms from mice injected with tumor cells from the two pateients whos lenti-let7 transduced cells established xenographs.

| Number of cells inoculated | | $2 \times 10^3$ cells | | | $5 \times 10^3$ cells | | |
|---|---|---|---|---|---|---|---|
| | | Primary Tumors | Passage 1 | Passage 2 | Primary Tumors | Passage 1 | Passage 2 |
| lin$^-$CD44$^+$CD24$^{-/low}$ | Untransduced | 6/8 | 8/8 | 8/8 | 8/8 | 8/8 | 8/8 |
| | Lentivirus | 6/8 | 8/8 | 8/8 | 7/8 | 8/8 | 8/8 |
| | Lenti-let-7 | 2/8* | 2/8$^\infty$ | 2/8$^\infty$ | 2/8$^\infty$ | 2/8$^\infty$ | 5/8* |
| lin$^-$NotCD44$^+$CD24$^{-/low}$ | | 0/8 | 0/8$^\#$ | 0/8$^\#$ | 0/8$^\#$ | 0/8 | 0/8$^\#$ |

Figure 4B:
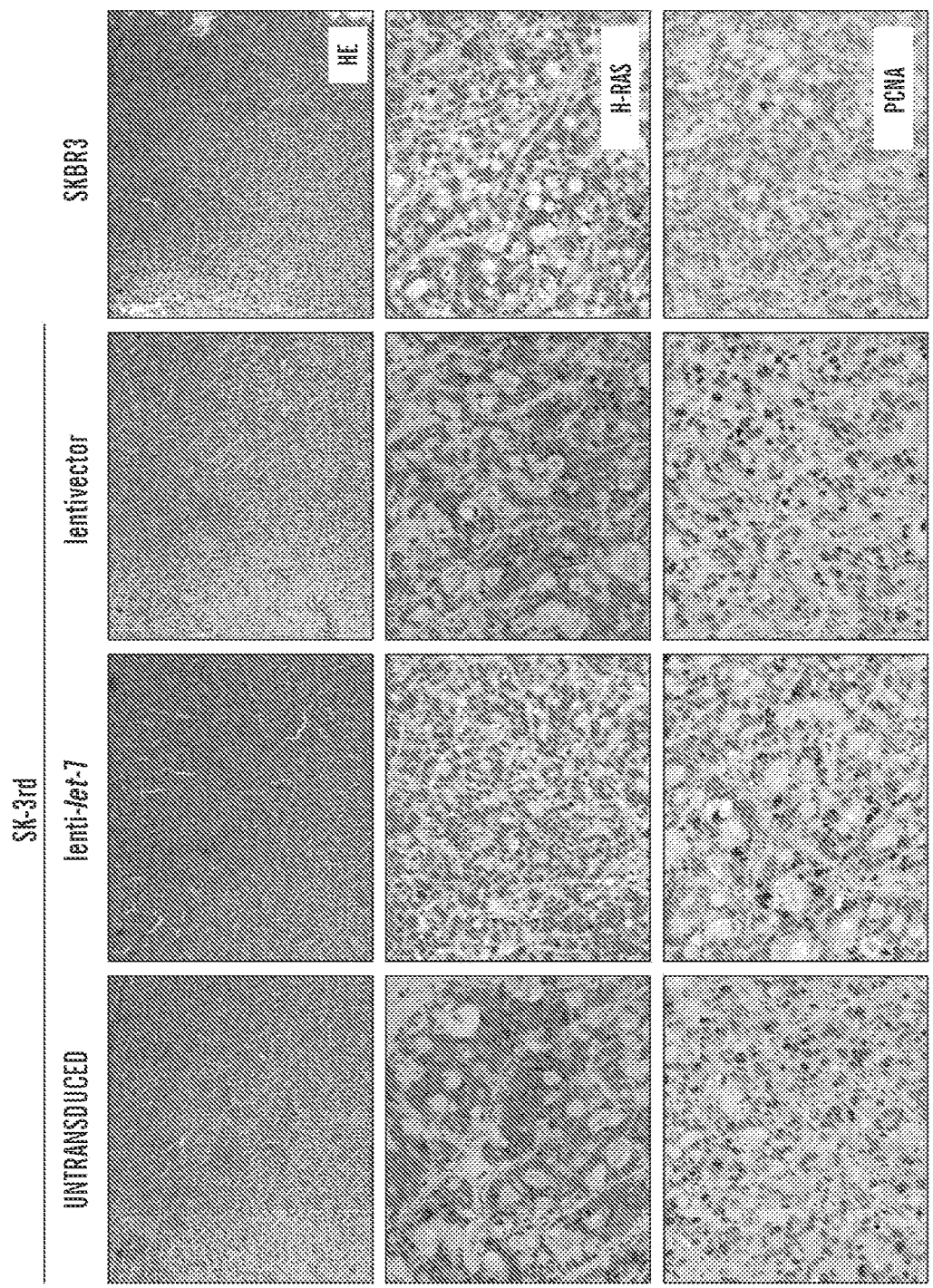
Figure 4C:
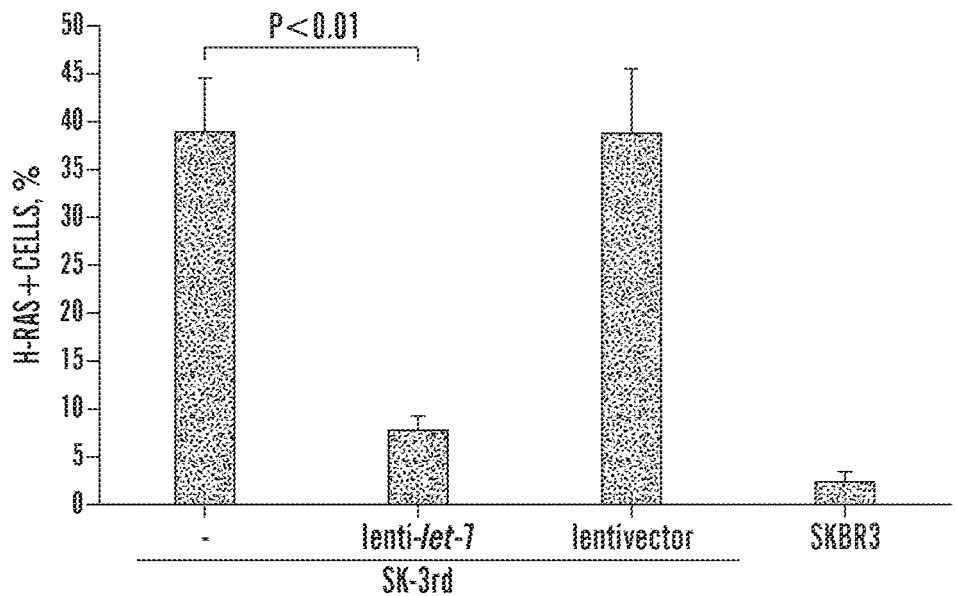
Figure 4D:
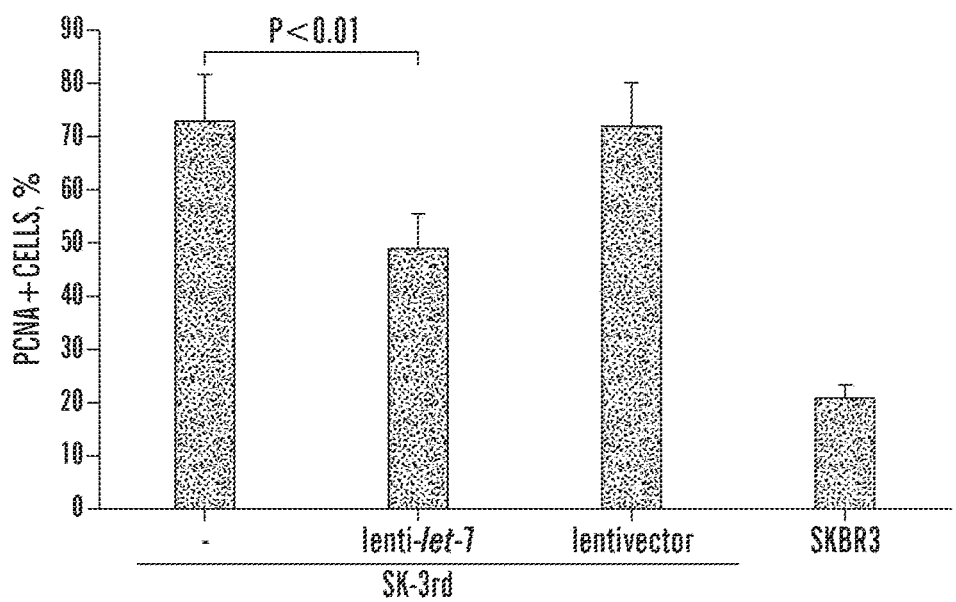

By hematoxylin and eosin staining, the tissue structure and cell morphology of the tumors generated from SKBR3, mammospheric SK-3rd or SK-3rd cells expressing let-7a were not grossly different (FIG. 4b). However, H-RAS expression by immunohistochemistry was much higher in xenografts generated from mammosphere-derived SK-3rd cells as compared to those from the parent SKBR3 cells. Transduction of SK-3rd with let-7a-lentivirus, but not control lentivirus, significantly reduced H-RAS in the tumors, almost to the level of SKBR3-derived tumors (FIG. 4b,c). In keeping with the faster growth of the SK-3rd tumors, a higher proportion of SK-3rd-derived tumor cells than SKBR3-derived tumor cells stained for the proliferating cell-associated antigen PCNA (FIG. 4b,d). Transduction of SK-3rd with let7 a-lentivirus also significantly reduced PCNA staining in the xenografted tumors, although not to that of the SKBR3-derived tumor. Therefore the inventors have demonstrated that the lack of let-7 plays an important role in the enhanced tumorigenicity and proliferation of tumor-initiating SK-3rd cells.

Example 9

Lack of Let-7 in Breast Tumor-Initiating Cells Promotes Lung and Liver Metastasis.

It has been hypothesized that cancer cells migrate to distal sites to initiate metastases only when they possess "stemlet-7a expression in SK-3$^{rd}$ reduced both the occurrence of liver metastasis by ~50% as well as their size. This was confirmed by measuring a 58% reduction in human HPRT mRNA in the livers of animals inoculated with lenti-let-7-transduced cells (n=3) as compared with those implanted with cells transduced with the control lentivirus (n=5, P<0.01; FIG. 5c). Therefore, the lack of let-7 in breast tumor-initiating cells contributes to their ability to metastasize to both the lung and liver.

The inventors have discovered breast tumors removed from patients treated with preoperative chemotherapy are enriched for tumor-initiating cells, also known as cancer stem cells. By taking advantage of the chemotherapeutic resistance of tumor-initiating cells, the inventors generated a human breast cancer stem cell line (SK-3rd) by sequential in vivo passage of a breast cancer cell line in immunodeficient mice treated with a low dose of a chemotherapeutic drug. The inventors discovered that their generated cancer stem cell line, SK-3$^{rd}$, has many of the hallmarks characteristic of stem cells, for instance, Sk-3$^{rd}$ cells have the ability for self-renewal, multipotent differentiation and vigorous proliferative capacity, as well as the ability to form mammospheres (or embryoid bodies), and are also positive for breast cancer stem cell phenotype (Oct4$^+$CD44$^+$CD24$^-$lineage)[1].

Moreover, the inventors also discovered SK-3rd was much more malignant in immunodeficient mice than the parental line—it required 100-fold fewer cells to produce tumors, and surprisingly the tumors from the SK-3$^{rd}$ metastasized, which did not occur at the same frequency in the parental line. Although there is a growing consensus that cancer stem cells are important in generating tumors and for resistance to therapy and metastasis, a major obstacle to their study is getting enough cells because of their very low frequency in tumors[9,10,12,37]. Herein, the inventors have discovered a method for enriching for cancer stem cells, to enable unlimited numbers of cancer stem cells to be obtained. The methods of the invention are useful for enriching for and obtaining unlimited numbers of cancer stem cells from any cancer type, for example breast cancer.

In vitro culture may produce epigenetic changes that might alter the properties of tumor-initiating cells in subtle, not easily detectable ways. Therefore, the inventors did as many of the studies as possible with freshly isolated in vivo passaged cells. Nonetheless, the self-renewing properties of the in vitro passaged mammospheres were highly stable (FIG. 1c), demonstrating that even with in vitro passage, mammospheres isolated from SK-3rd maintain "stemness" and their self-renewal capacity. The inventors were careful to compare their results generated with an in vivo passaged cell line with those obtained in freshly isolated primary breast cancer cells. The primary tumors resected from adjuvant chemotherapy-treated patients had a surprisingly high frequency (~6%) of mammospheric cells with expected properties of tumor-initiating cells, a frequency that was only a third that of the mouse-passaged stem cell line (16%) and 14 times that of untreated-patient tumors. Therefore, the inventors have discovered that enriched primary breast tumor-initiating cells, or cancer stem cells, obtained from chemotherapy-treated patients are good source for studying primary tumor-initiating cells, particularly cancer stem cells from human subject.

The inventors also discovered that the expression of let-7 miRNA and let-7 homologues are significantly reduced or lacking in tumor-initiating SK-3$^{rd}$ cells, distinguishing SK-3$^{rd}$ tumor-initiating cells from both their differentiated progeny and the parental cell line. Moreover, the inventors discovered that lack of let-7 is required to maintain "stemness" and cancer stem cells self-renewal capacity. By over-expressing let-7a in SK-3$^{rd}$ cells, the inventors discovered that let-7 reduces self-renewal and proliferative capability and converts highly malignant and metastasizing tumor-initiating into less malignant cells, similar to the parental cells. Conversely, by antagonizing let-7 with antisense oligonucleotides (ASO) in the parental line, the inventors discovered that reduction of let-7 in the parental line had the effect of enhancing its self-renewal potential.

let-7 genes map to sites with frequent chromosomal instability during oncogenesis[40], and let-7 is poorly expressed in lung[24,33] and colon cancer[41]. Down-regulation of let-7 has not been reported in breast cancer[42] let-7 has been postulated to work as a tumor suppressor gene by silencing the expression of the RAS oncogenes[31]. The inventors also discovered that in the SK-3$^{rd}$ cancer stem cells which only express HRAS, that the H-RAS protein, but not mRNA, was inversely correlated with let-7; H-RAS was high in tumor-initiating SK-3rd, but low in differentiated SK-3rd and SKBR3. Moreover, the inventors discovered that exogenous let-7a significantly knocked-down H-RAS. H-RAS is increased in up to 60% of human breast cancers[43,44], but mutations are rare[44,45]. In additional experiments, the inventors discovered that silencing RAS to a level similar to that mediated by let-7 had much less of an effect on cancer stem cell self-renewal and in vitro differentiation than over-expressing let-7, leading to the discovery that RAS is not the only target of let-7 that contributes to maintaining "sternness" of cancer stem cells.

REFERENCES

The references cited herein and throughout the application are incorporated herein in their entirety by reference.
1. Jordan, C. T., Guzman, M. L. & Noble, M. Cancer stem cells. *N Engl J Med* 355, 1253-61 (2006).
2. Polyak, K. & Hahn, W. C. Roots and stems: stem cells in cancer. *Nat Med* 12, 296-300 (2006).
3. Wang, J. C. & Dick, J. E. Cancer stem cells: lessons from leukemia. *Trends Cell Biol* 15, 494-501 (2005).
4. Jordan, C. T. & Guzman, M. L. Mechanisms controlling pathogenesis and survival of leukemic stem cells. *Oncogene* 23, 7178-87 (2004).
5. Dick, J. E. Acute myeloid leukemia stem cells. *Ann N Y Acad Sci* 1044, 1-5 (2005).
6. Vescovi, A. L., Galli, R. & Reynolds, B. A. Brain tumour stem cells. *Nat Rev Cancer* 6, 425-36 (2006).
7. Galli, R. et al. Isolation and characterization of tumorigenic, stem-like neural precursors from human glioblastoma. *Cancer Res* 64, 7011-21 (2004).
8. Singh, S. K. et al. Identification of human brain tumour initiating cells. *Nature* 432, 396-401 (2004).
9. Al-Hajj, M., Wicha, M. S., Benito-Hernandez, A., Morrison, S. J. & Clarke, M. F. Prospective identification of tumorigenic breast cancer cells. *Proc Natl Acad Sci USA* 100, 3983-8 (2003).
10. Ponti, D. et al. Isolation and in vitro propagation of tumorigenic breast cancer cells with stem/progenitor cell properties. *Cancer Res* 65, 5506-11 (2005).
11. Patrawala, L. et al. Highly purified CD44+ prostate cancer cells from xenograft human tumors are enriched in tumorigenic and metastatic progenitor cells. *Oncogene* 25, 1696-708 (2006).
12. O'Brien C, A., Pollett, A., Gallinger, S. & Dick, J. E. A human colon cancer cell capable of initiating tumour growth in immunodeficient mice. *Nature* (2006).
13. Dalerba, P., Cho, R. W. & Clarke, M. F. Cancer Stem Cells: Models and Concepts. *Annu Rev Med* (2006).
14. Wicha, M. S. Cancer stem cells and metastasis: lethal seeds. *Clin Cancer Res* 12, 5606-7 (2006).
15. Sheridan, C. et al. CD44+/CD24− breast cancer cells exhibit enhanced invasive properties: an early step necessary for metastasis. *Breast Cancer Res* 8, R59 (2006).
16. Eramo, A. et al. Chemotherapy resistance of glioblastoma stem cells. *Cell Death Differ* 13, 1238-41 (2006).
17. Dean, M., Fojo, T. & Bates, S. Tumour stem cells and drug resistance. *Nat Rev Cancer* 5, 275-84 (2005).
18. Lu, J. et al. MicroRNA expression profiles classify human cancers. *Nature* 435, 834-8 (2005).
19. Chen, C. Z. MicroRNAs as oncogenes and tumor suppressors. *N Engl J Med* 353, 1768-71 (2005).
20. Hatfield, S. D. et al. Stem cell division is regulated by the microRNA pathway. *Nature* 435, 974-8 (2005).
21. Croce, C. M. & Calin, G. A. miRNAs, cancer, and stem cell division. *Cell* 122, 6-7 (2005).
22. Shcherbata, H. R. et al. The MicroRNA pathway plays a regulatory role in stem cell division. *Cell Cycle* 5, 172-5 (2006).
23. Murdie, P. MicroRNA signature predicts prognosis and progression of chronic lymphocytic leukemia. *Nat Clin Pract Oncol* 3, 67 (2006).

24. Yanaihara, N. et al. Unique microRNA molecular profiles in lung cancer diagnosis and prognosis. *Cancer Cell* 9, 189-98 (2006).
25. Dontu, G. et al. In vitro propagation and transcriptional profiling of human mammary stem/progenitor cells. *Genes Dev* 17, 1253-70 (2003).
26. Dontu, G. et al. Role of Notch signaling in cell-fate determination of human mammary stem/progenitor cells. *Breast Cancer Res* 6, R605-15 (2004).
27. Tang, F., Hajkova, P., Barton, S. C., Lao, K. & Surani, M. A. MicroRNA expression profiling of single whole embryonic stem cells. *Nucleic Acids Res* 34, e9 (2006).
28. Reinhart, B. J. et al. The 21-nucleotide let-7 RNA regulates developmental timing in *Caenorhabditis elegans*. *Nature* 403, 901-6 (2000).
29. Abbott, A. L. et al. The let-7 MicroRNA family members mir-48, mir-84, and mir-241 function together to regulate developmental timing in *Caenorhabditis elegans*. *Dev Cell* 9, 403-14 (2005).
30. Grosshans, H., Johnson, T., Reinert, K. L., Gerstein, M. & Slack, F. J. The temporal patterning microRNA let-7 regulates several transcription factors at the larval to adult transition in *C. elegans*. *Dev Cell* 8, 321-30 (2005).
31. Johnson, S. M. et al. RAS is regulated by the let-7 microRNA family. *Cell* 120, 635-47 (2005).
32. Banerjee, D. & Slack, F. Control of developmental timing by small temporal RNAs: a paradigm for RNA-mediated regulation of gene expression. *Bioessays* 24, 119-29 (2002).
33. Takamizawa, J. et al. Reduced expression of the let-7 microRNAs in human lung cancers in association with shortened postoperative survival. *Cancer Res* 64, 3753-6 (2004).
34. Townson, J. L. & Chambers, A. F. Dormancy of solitary metastatic cells. *Cell Cycle* 5, 1744-50 (2006).
35. Liu, G. et al. Analysis of gene expression and chemoresistance of CD133+ cancer stem cells in glioblastoma. *Mol Cancer* 5, 67 (2006).
36. Vander Borght, S. et al. Breast cancer resistance protein (BCRP/ABCG2) is expressed by progenitor cells/reactive ductules and hepatocytes and its expression pattern is influenced by disease etiology and species type: possible functional consequences. *J Histochem Cytochem* 54, 1051-9 (2006).
37. Youn, B. S., Sen, A., Behie, L. A., Girgis-Gabardo, A. & Hassell, J. A. Scale-up of breast cancer stem cell aggregate cultures to suspension bioreactors. *Biotechnol Prog* 22, 801-10 (2006).
38. Soutschek, J. et al. Therapeutic silencing of an endogenous gene by systemic administration of modified siRNAs. *Nature* 432, 173-8 (2004).
39. Song, E. et al. Antibody mediated in vivo delivery of small interfering RNAs via cell-surface receptors. *Nat Biotechnol* 23, 709-17 (2005).
40. Calin, G. A. et al. Human microRNA genes are frequently located at fragile sites and genomic regions involved in cancers. *Proc Natl Acad Sci USA* 101, 2999-3004 (2004).
41. Akao, Y., Nakagawa, Y. & Naoe, T. let-7 microRNA functions as a potential growth suppressor in human colon cancer cells. *Biol Pharm Bull* 29, 903-6 (2006).
42. Iorio, M. V. et al. MicroRNA gene expression deregulation in human breast cancer. *Cancer Res* 65, 7065-70 (2005).
43. Hanahan, D. & Weinberg, R. A. The hallmarks of cancer. *Cell* 100, 57-70 (2000).
44. Downward, J. Targeting RAS signalling pathways in cancer therapy. *Nat Rev Cancer* 3, 11-22 (2003).
45. Bos, J. L. ras oncogenes in human cancer: a review. *Cancer Res* 49, 4682-9 (1989).
46. Kawasaki, H., Suyama, E., Iyo, M. & Taira, K. siRNAs generated by recombinant human Dicer induce specific and significant but target site-independent gene silencing in human cells. *Nucleic Acids Res* 31, 981-7. (2003).
47. Lee, S. K. et al. Lentiviral delivery of short hairpin RNAs protects CD4 T cells from multiple clades and primary isolates of HIV. *Blood* 106, 818-26 (2005).
48. Muller, A. et al. Involvement of chemokine receptors in breast cancer metastasis. *Nature* 410, 50-6 (2001).

What is claimed:

1. A method to inhibit the proliferation of a human breast cancer stem cell expressing having a phenotype of lin$^-$/ CD44$^+$/ CD24$^{-/low}$, comprising:
   (i) contacting a breast cancer stem cell with a composition comprising a let-7 miRNA, a binding moiety and a targeting moiety, wherein the binding moiety connects the let-7 miRNA to the targeting moiety and wherein the targeting moiety binds to CD44+on the surface of the breast cancer stem cell,
   (ii) inhibiting the proliferation of the human breast cancer stem cell having a phenotype of lin$^-$/ CD44$^+$/ CD24$^{-/low}$ when the let-7 miRNA binds to and inhibits a RNA transcript comprising a let-7 target sequence in the breast cancer stem cell.

2. The method of claim 1, wherein the let-7 target sequence comprises SEQ ID NO: 9 or SEQ ID NO: 10 or SEQ ID NO:11.

3. The method of claim 1, wherein the let-7 miRNA is selected from the group consisting of let-7a, let-7a1, let-7b, let-7c, let-7d, let-7e and let-7f.

4. The method of claim 1, wherein the miRNA is a pri-miRNA, pre-miRNA, mature miRNA effective in gene silencing.

5. The method of claim 1, wherein the let-7 miRNA comprises SEQ ID NO:1-8.

6. The method of claim 1, wherein the breast cancer is selected from at least one of the group consisting of a pre-cancer, malignant breast cancer, therapy resistant breast cancer.

7. The method of claim 1, wherein the targeting moiety is selected from the group consisting of: an antibody, a single chain antibody, a Fab portion of an antibody and a (Fab')2 segment.

8. The method of claim 1, wherein the binding moiety is a protein or a nucleic acid binding domain of a protein, and the binding moiety is fused to the carboxyl terminus of the targeting moiety.

9. The method of claim 1, wherein the binding moiety is the protein protamine or nucleic acid binding fragment of protamine.

10. The method of claim 1, wherein the breast cancer stem cells are also express at least one of Oct-4 or HRAS.

11. The method of claim 1, wherein the breast cancer stem cells are also express proliferating cell-associated antigen (PCNA).

12. The method of claim 1, wherein the breast cancer stem cells do not express CK14 or CK18.

\* \* \* \* \*

SEQUENCE LISTING

<160> NUMBER OF SEQ ID NOS: 15

<210> SEQ ID NO 1
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
ugagguagua gguuguauag uu                                              22

<210> SEQ ID NO 2
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
ugagguagua gguugugugg uu                                              22

<210> SEQ ID NO 3
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
ugagguagua gguuguaugg uu                                              22

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
agagguagua gguugcauag u                                               21

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
ugagguagga gguuguauag u                                               21

<210> SEQ ID NO 6
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
ugagguagua gauuguauag uu                                              22

<210> SEQ ID NO 7
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
ugggaugagg uaguagguug uauaguuuua ggucacacc caccacuggg agauaacuau       60
acaaucuacu gucuuuccua                                                 80

<210> SEQ ID NO 8
<211> LENGTH: 80
<212> TYPE: RNA
<213> ORGANISM: Homo sapiens

<400> SEQUENCE: 8
ugggaugagg uaguagguug uauaguuuua gggucacacc caccacuggg agauaacuau      60
acaaucuacu gucuuuccua                                                 80

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
aactatacaa cctactacct ca                                              22

<210> SEQ ID NO 10
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
aatgcactag taactataca acctactacc tcagctcagc aagcttaatg c               51

<210> SEQ ID NO 11
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gcattaagct tgctgagctg aggtagtagg ttgtatagtt actagtgcat t               51

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
tactatacaa cctactacct caatttgcc                                       29

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
gcagggccca tgctaatctt ctctgtatcg                                      30

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
aactatacaa tctactgtct t                                               21

```
<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
aactatacaa cctactacct                                                  20
```